(12) United States Patent
Prakash et al.

(10) Patent No.: US 8,036,867 B2
(45) Date of Patent: Oct. 11, 2011

(54) METHOD AND APPARATUS FOR ANALYSIS OF MOLECULAR CONFIGURATIONS AND COMBINATIONS

(75) Inventors: Adityo Prakash, Fremont, CA (US); David Kita, Milpitas, CA (US); Eniko Fodor, Fremont, CA (US)

(73) Assignee: Verseon, Milpitas, CA (US)

(*) Notice: Subject to any disclaimer, the term of this patent is extended or adjusted under 35 U.S.C. 154(b) by 781 days.

(21) Appl. No.: 10/967,085

(22) Filed: Oct. 14, 2004

(65) Prior Publication Data

US 2005/0119837 A1      Jun. 2, 2005

Related U.S. Application Data

(60) Provisional application No. 60/511,387, filed on Oct. 14, 2003.

(51) Int. Cl.
*G06G 7/48* (2006.01)
*G06G 7/58* (2006.01)
*G01N 33/48* (2006.01)
*G01N 31/00* (2006.01)

(52) U.S. Cl. ............... 703/11; 703/12; 702/19; 702/22

(58) Field of Classification Search .................. None
See application file for complete search history.

(56) References Cited

U.S. PATENT DOCUMENTS

| 3,648,253 | A  | * | 3/1972  | Mullery et al. | ............... 718/100   |
| 5,095,264 | A  | * | 3/1992  | Hulsing, II    | ................ 324/76.47 |
| 6,608,514 | B1 | * | 8/2003  | Akita et al.   | .................... 327/291 |
| 6,832,162 | B2 | * | 12/2004 | Floudas et al. | .................. 702/19   |

FOREIGN PATENT DOCUMENTS

WO      WO 02/063479 A1 *    8/2002

OTHER PUBLICATIONS

Sheinerman et al. On the role of electrostatic interactions in the design of protein-protein interfaces. Journal of Molecular Biology. 2002, vol. 318, pp. 161-177.*
Nicholls et al. A rapid finite difference algorithm, utilizing successive over relaxation to solve the Poisson-Boltzmann Equation. Journal of Computational Chemistry, vol. 12, 1991, pp. 435-445.*

(Continued)

*Primary Examiner* — Russell S Negin
(74) *Attorney, Agent, or Firm* — Kilpatrick Townsend and Stockton LLP

(57) ABSTRACT

Computing units are determined for performing molecular docking calculations in parallel with the number of computing units and the width of the data paths allocated by relative complexity of operations. Data can be expected to arrive at downstream computing units as it is needed, leading to higher utilization of computing units. Computing units are hardware components that are specific to a calculation performed. For molecular docking calculations, functions of molecular subsets or of combinations of molecular subsets are calculated. Determinations include fit between molecular subsets, affinity or energy of "fit" between molecular subsets, etc. Affinity might include inter-atomic energy, bond energy, energy of atoms immersed in a field, etc. The calculations could be used to simulate and/or estimate likelihoods of molecular interactions.

46 Claims, 19 Drawing Sheets

Modeling system

OTHER PUBLICATIONS

Cao et al. Implementation and performance of integrated application-controlled file caching, prefetching, and disk scheduling. ACM Transactions on Computer Systems, 1996, vol. 14, pp. 311-343.*

Kay et al. Three dimensional triple-resonance NMR spectroscopy of isotopically enriched proteins. Journal of Magnetic Resonance, vol. 89, 1990, pp. 496-514.*

Brooks et al. CHARMM: A Program for Macromolecular Energy, Minimization, and Dynamics Calculations. Journal of Computational Chemistry, 1983, vol. 4, pp. 187-217.*

Definition of "word." The Penguin Dictionary of Science, 2009, one page. Retrieved online on May 26, 2011 from<<http://www.credoreference.com/entry/penguinscience/word>>.*

Cornell et al. "A Second Generation Force Field for the Simulation of Proteins, Nucleic Acids, and Organic Molecules", Journal of the American Chemical Society, (1995), pp. 5179-5197, vol. 117.

Ewing et al. "Critical evaluation of search algorithms for automated molecular docking and database searching" Journal of Computational Chemistry, (1997), pp. 1175-1189, vol. 18.

Lamb et al. "Design, docking, and evaluation of multiple libraries against multiple targets", Proteins: Structure, Function, and Genetics, (2001), pp. 296-318, vol. 42.

Martino et al., "Parellel Computing in Biomedical Research", Science, (1994), pp. 902-908 vol. 265.

* cited by examiner

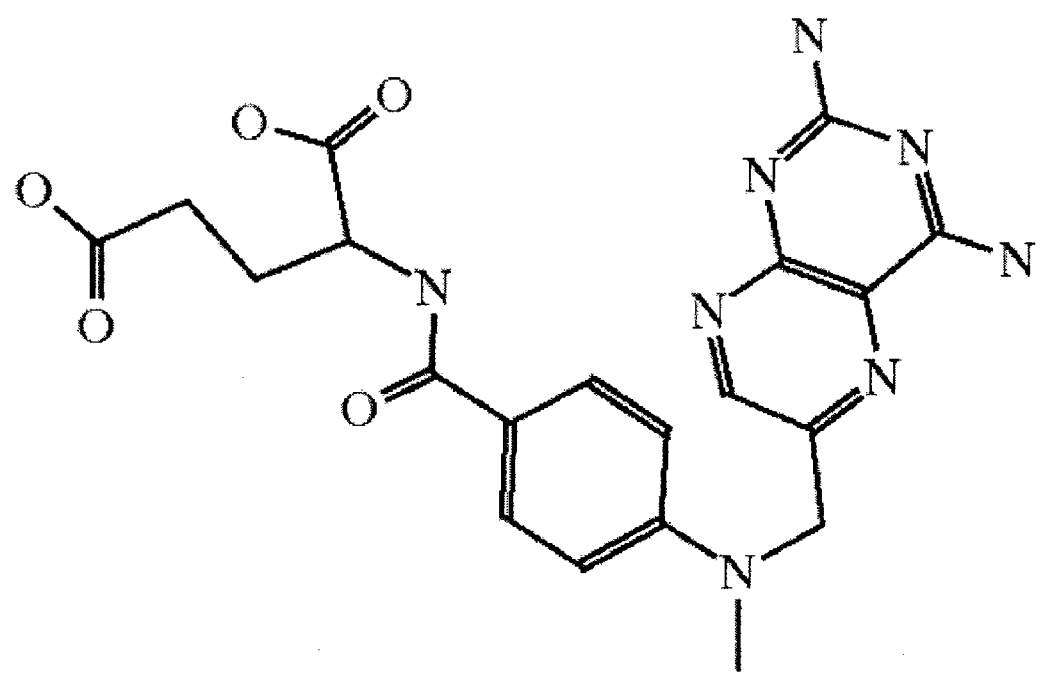
FIG. 2A: 2-D schematic representation of methotrexate

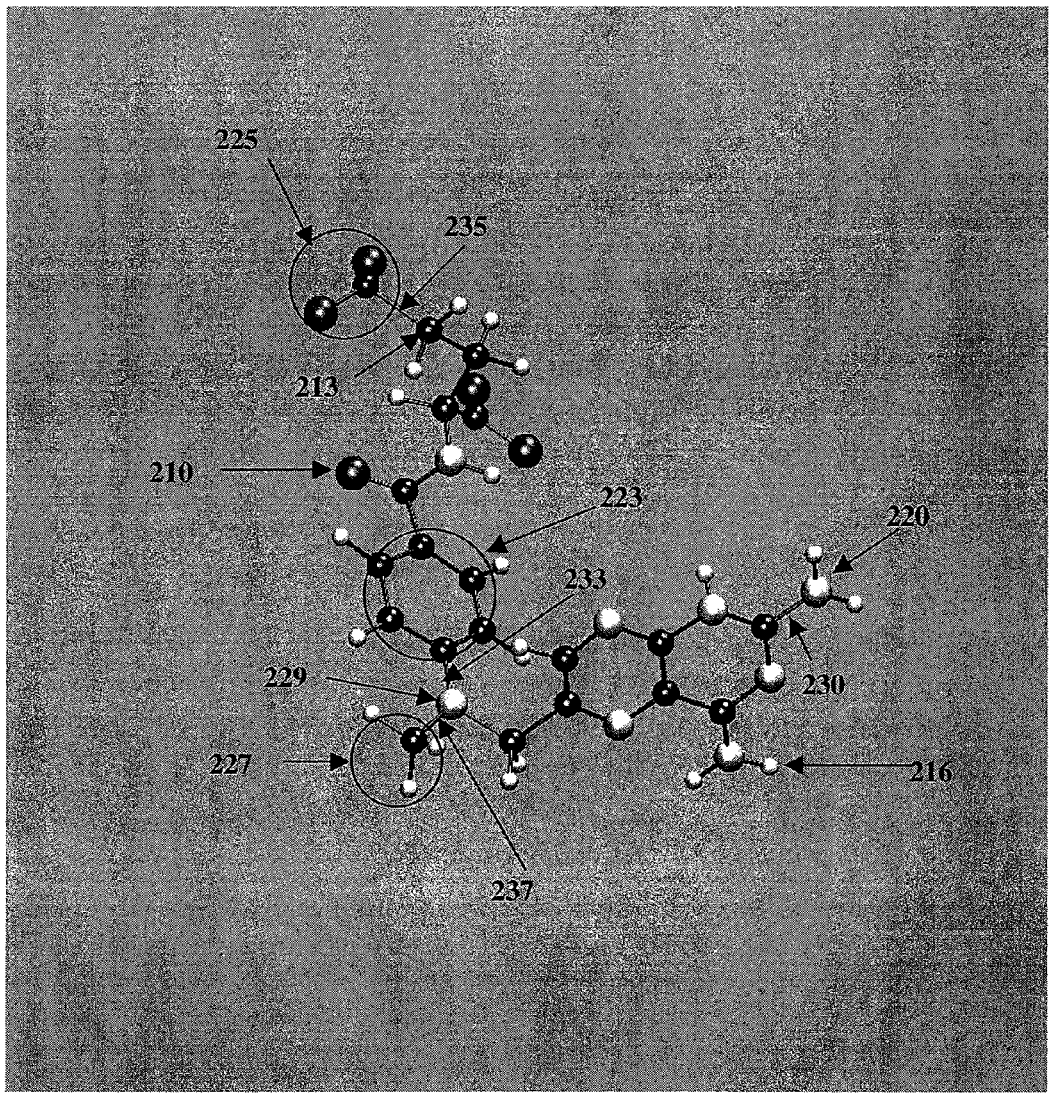
FIG. 2B: Ball-and-stick representation of methotrexate conformation

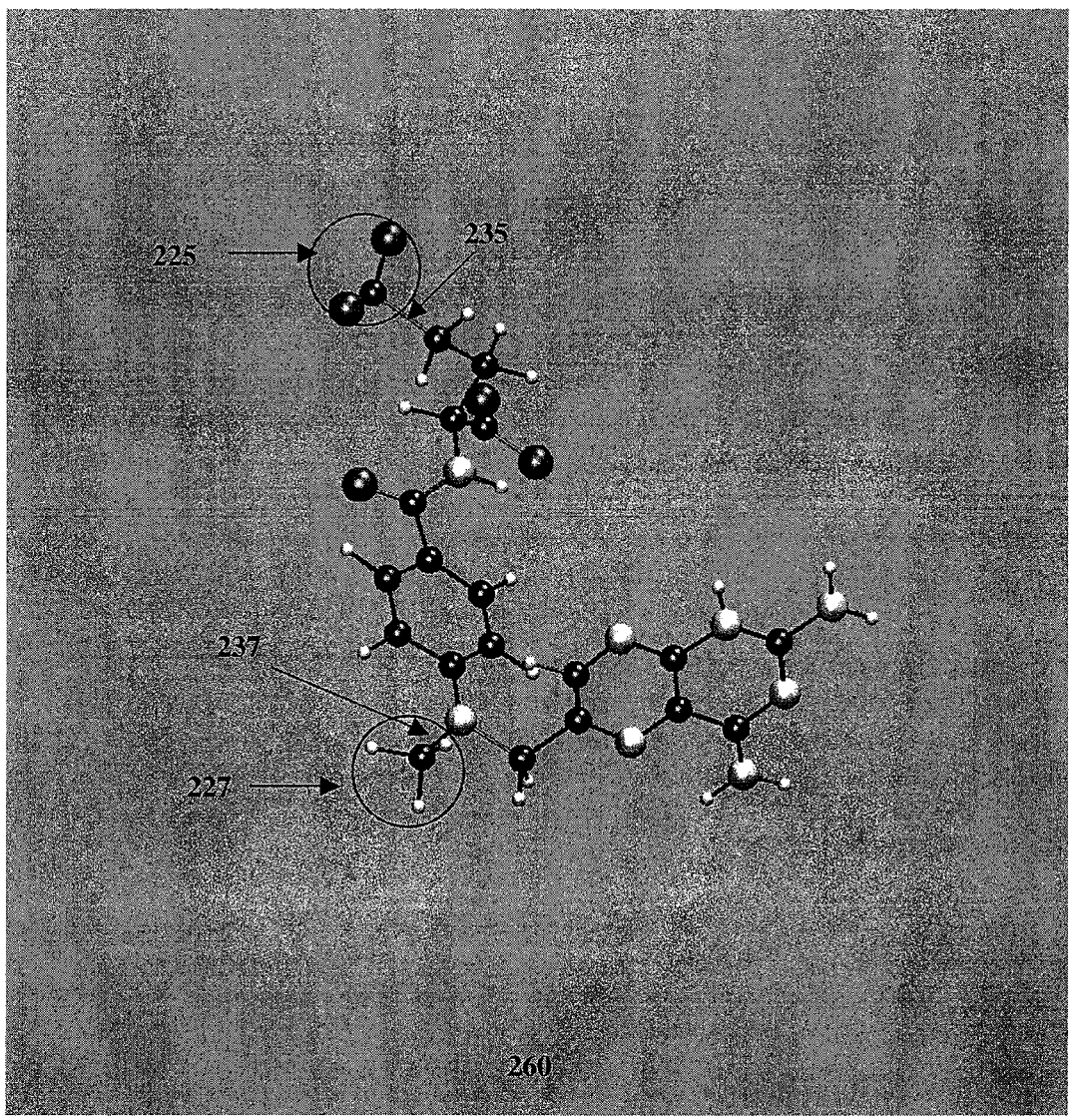
FIG. 2C: Ball and stick representation of a conformation of methotrexate

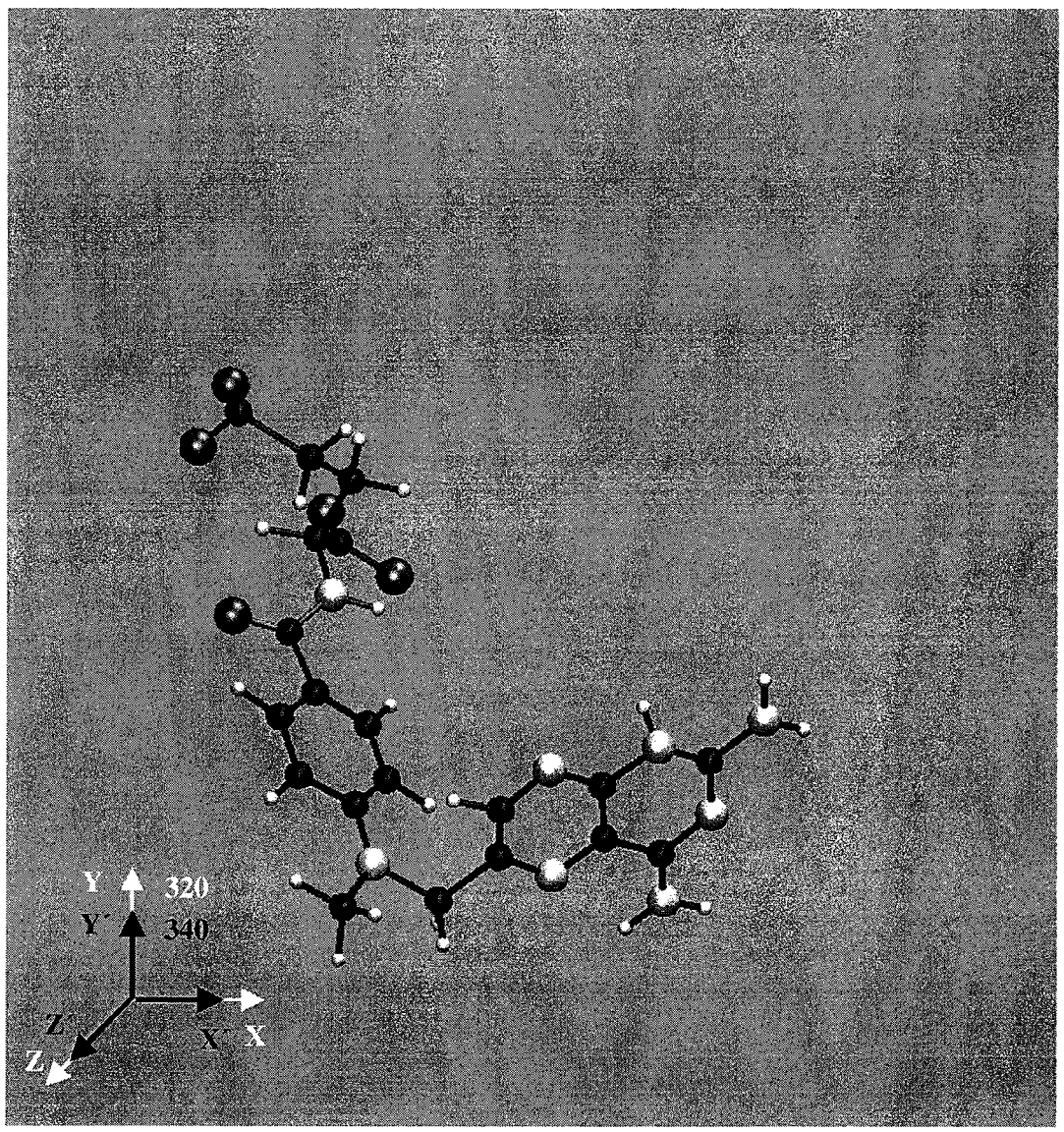
FIG. 3A: Pose of methotrexate with cartesian frame aligned with global 3D coordinate system

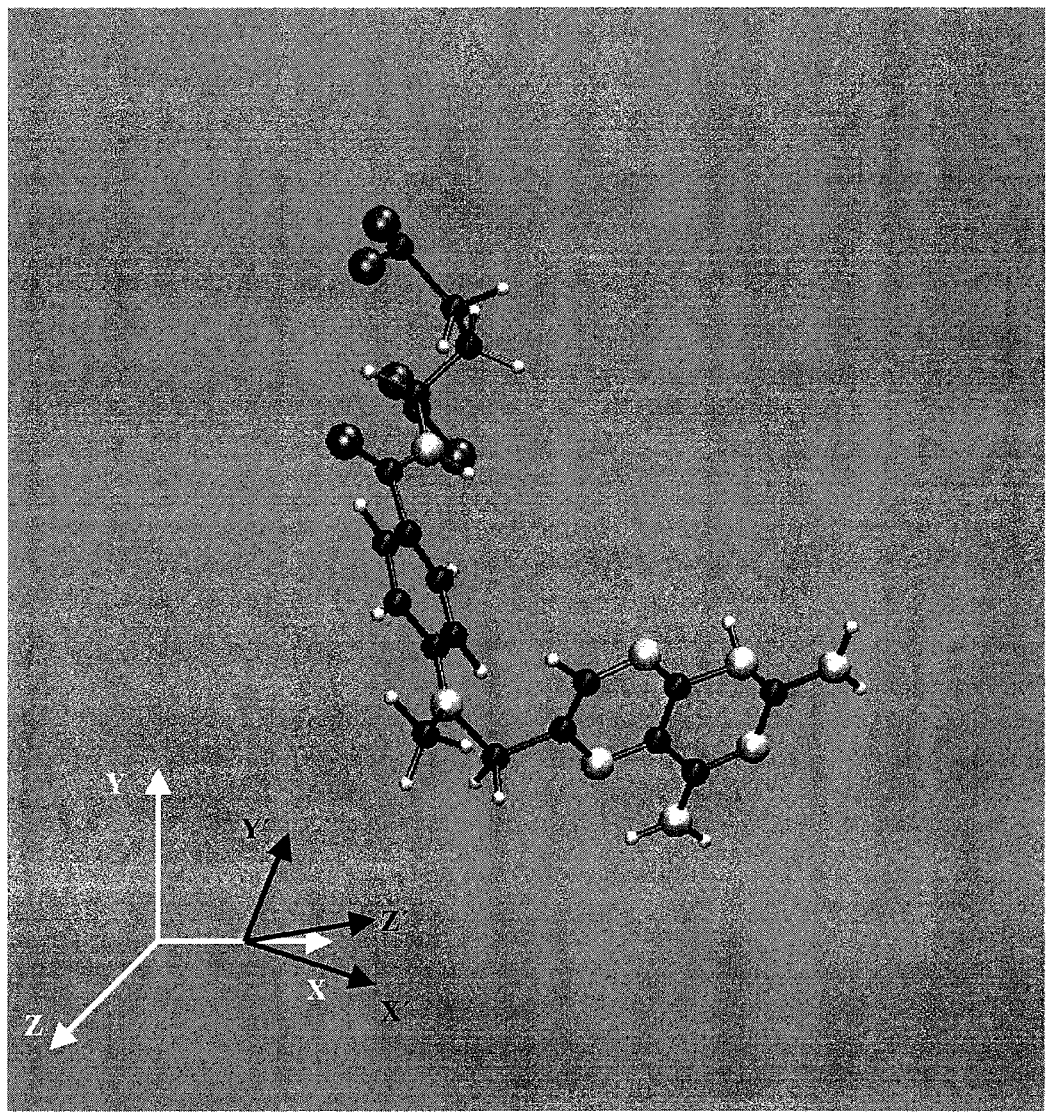
FIG. 3B: Another pose of methotrexate after translation and rigid body rotation

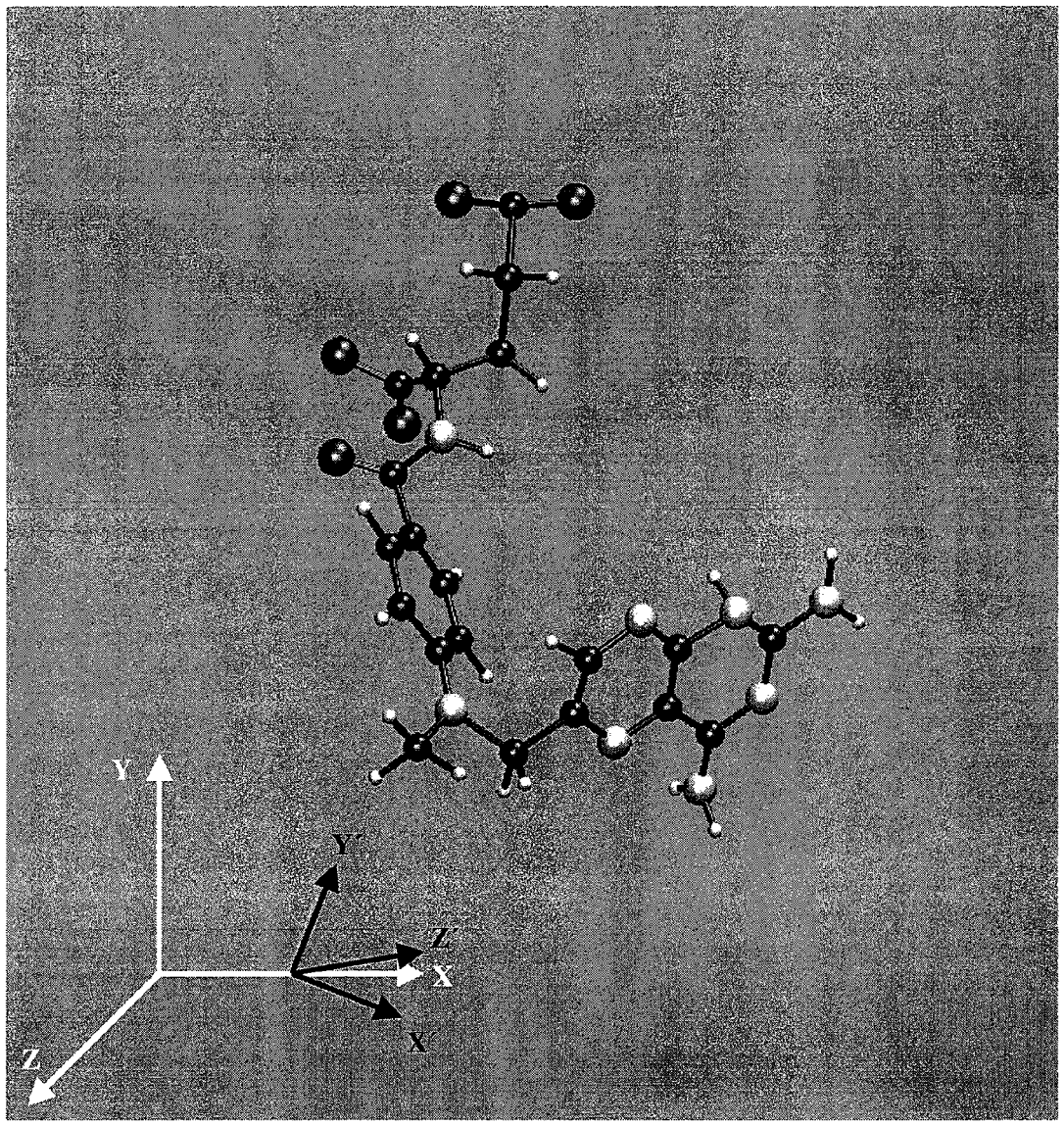
FIG. 3C: Another pose of methotrexate involving translation, rigid body rotation and changes in conformation

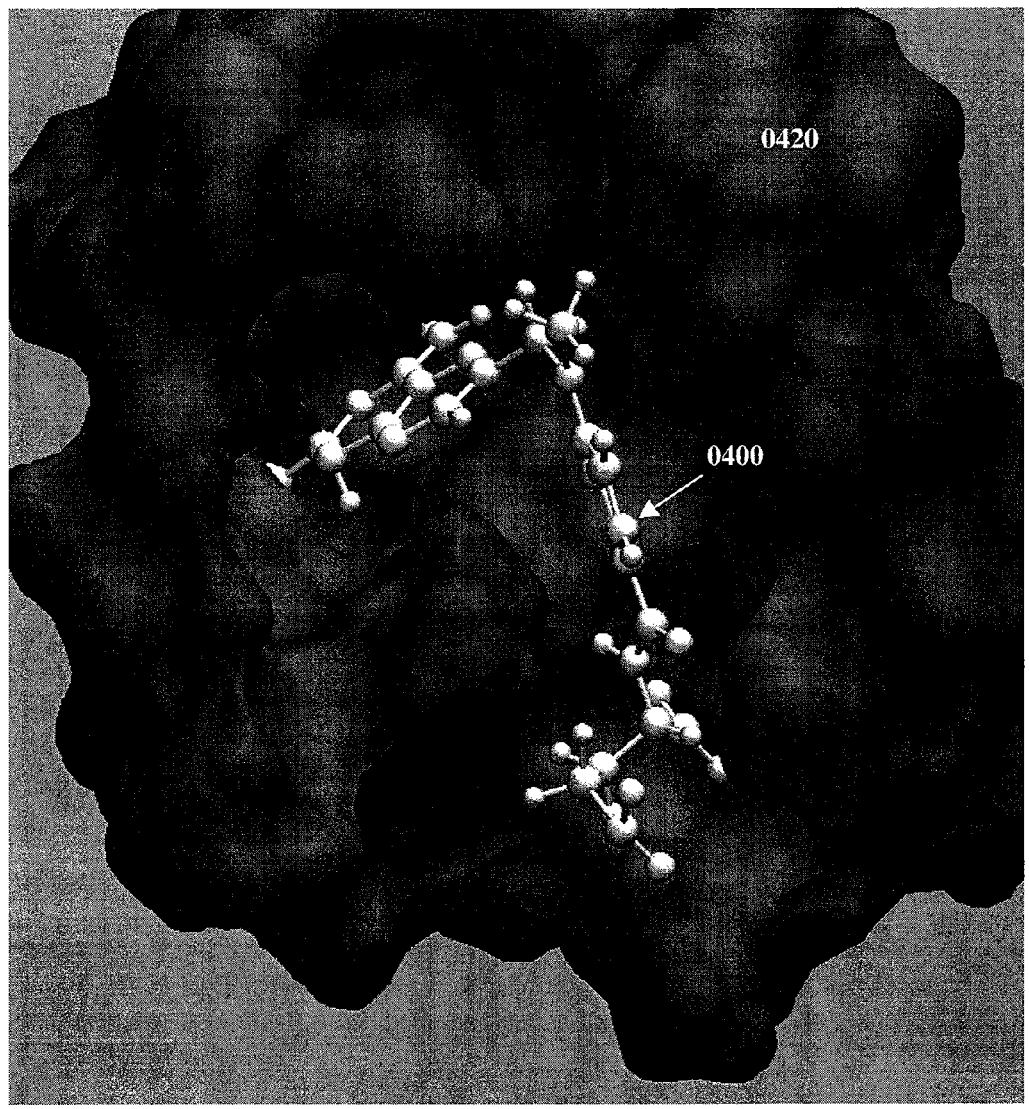
FIG. 4A: Example configuration of a molecular combination featuring methotrexate and dihydrofolate reductase

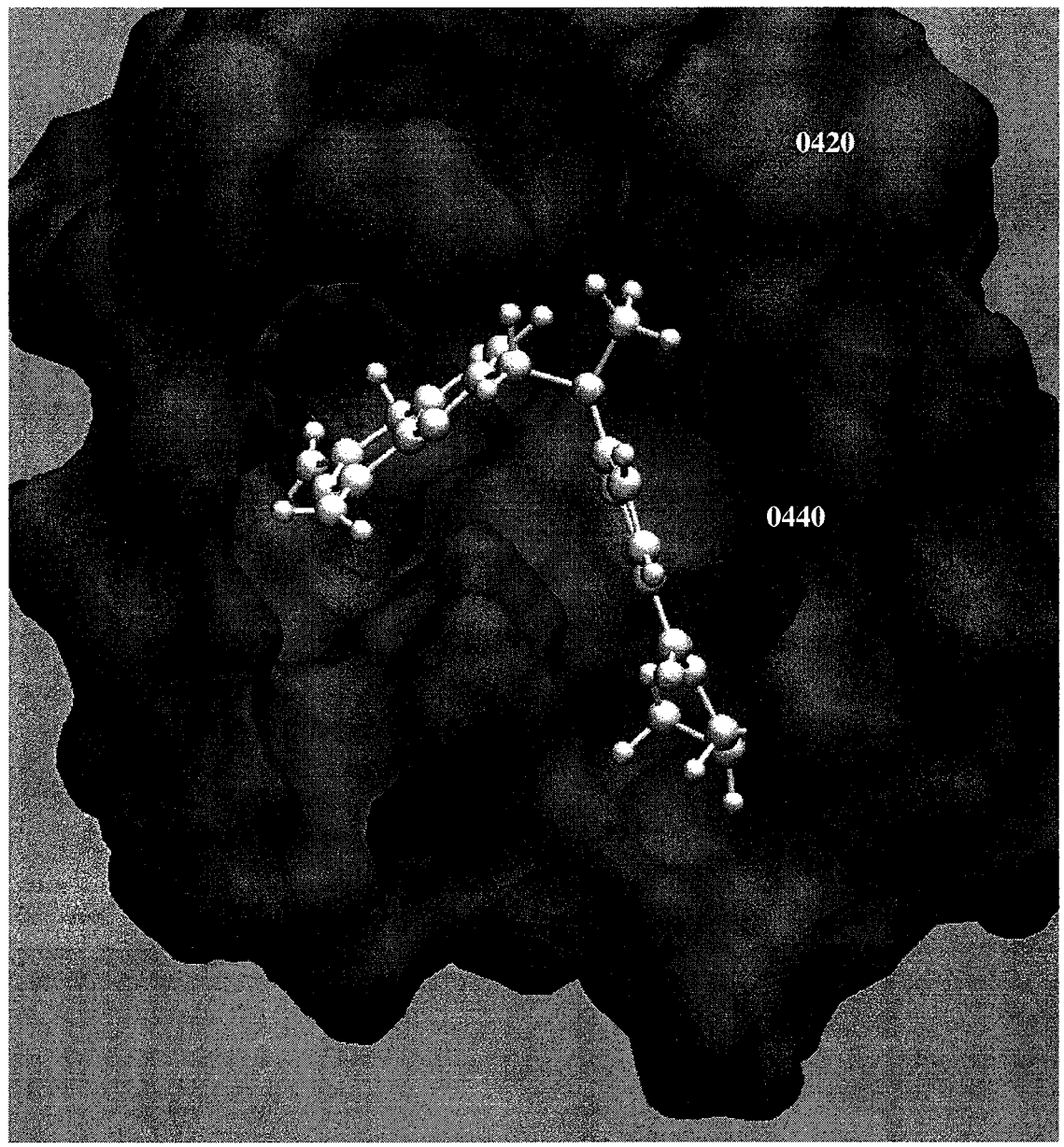
FIG. 4B: Another configuration for a molecular combination featuring the same pose of dihydrofolate reductase but a different pose of methotrexate

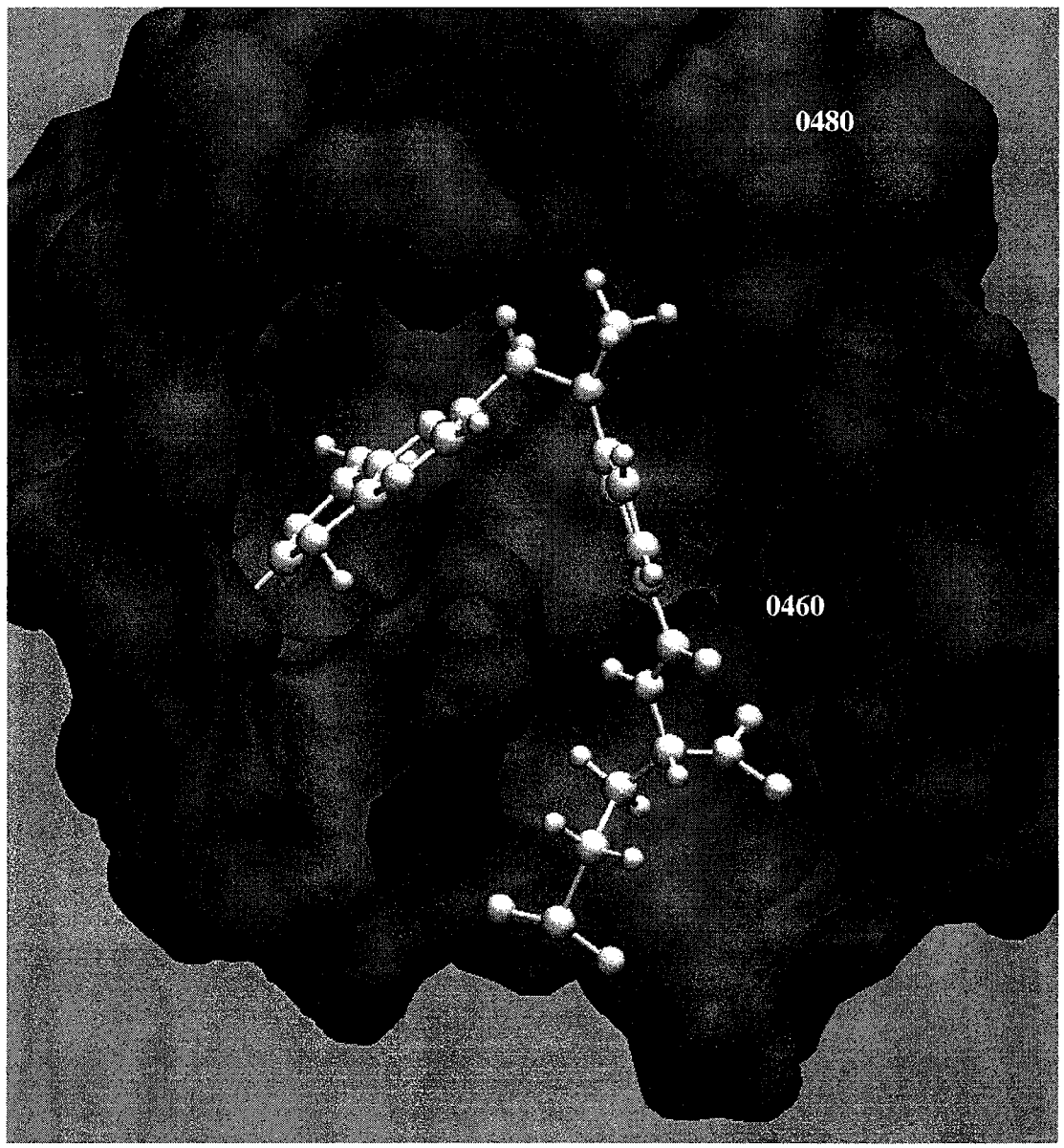
FIG. 4C: Yet another configuration for a molecular combination featuring different poses for both dihydrofolate reductase and methotrexate

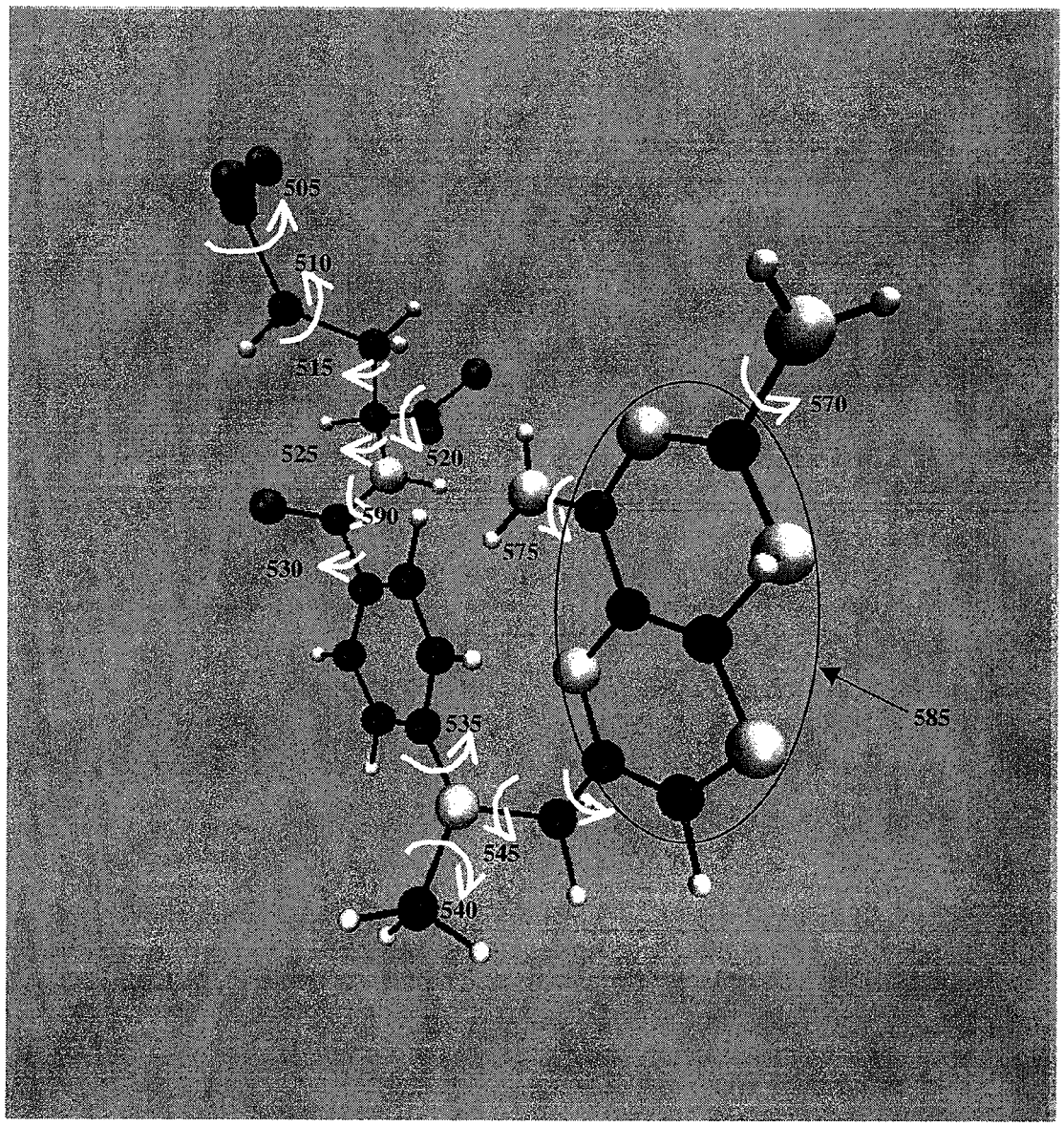
FIG. 5: Torsional degrees of freedom for methotraxate

```
HEADER  OXIDO-REDUCTASE           25-JUN-82  4DFR
COMPND  DIHYDROFOLATE REDUCTASE (E.C.1.5.1.3) COMPLEX WITH
COMPND  2 METHOTREXATE
SOURCE  (ESCHERICHIA SCOLI B), STRAIN /MB1428S,
SOURCE  2 A METHOTREXATE-RESISTANT MUTANT
AUTHOR  D.J.FILMAN,D.A.MATTHEWS,J.T.BOLIN,J.KRAUT
JRNL    AUTH  J.T.BOLIN,D.J.FILMAN,D.A.MATTHEWS,R.C.HAMLIN,
JRNL    AUTH 2 J.KRAUT
JRNL    REF  J.BIOL.CHEM.       V. 257 13650 1982
REMARK  1 RESOLUTION. 1.7
ANGSTROMS.
FORMUL  2 MTX  2(C20 H22 N8 O5)
HETATM  1 N1  MTX A  1    22.983 58.667 24.488 1.00 15.10
HETATM  2 C2  MTX A  1    23.468 58.215 23.282 1.00 17.30
HETATM  3 NA2 MTX A  1    24.797 58.223 23.208 1.00 16.50
HETATM  4 N3  MTX A  1    22.792 57.819 22.230 1.00 17.90
HETATM  5 C4  MTX A  1    21.459 57.803 22.068 1.00 18.60
HETATM  6 NA4 MTX A  1    20.821 57.440 21.075 1.00 18.10
HETATM  7 C4A MTX A  1    20.900 58.304 23.363 1.00 18.90
HETATM  8 N5  MTX A  1    19.558 58.514 23.370 1.00 19.80
HETATM  9 C6  MTX A  1    18.989 58.982 24.422 1.00 18.60
HETATM 10 C7  MTX A  1    19.781 59.256 25.628 1.00 18.80
HETATM 11 N8  MTX A  1    21.096 59.176 25.562 1.00 21.90
HETATM 12 C8A MTX A  1    21.608 58.594 24.363 1.00 19.50
HETATM 13 C9  MTX A  1    17.465 59.006 24.451 1.00 20.50
HETATM 14 N10 MTX A  1    16.957 59.967 25.533 1.00 17.40
HETATM 15 CM  MTX A  1    16.225 59.184 26.643 1.00 22.30
HETATM 16 C11 MTX A  1    18.122 64.100 25.805 1.00 22.10
HETATM 17 C12 MTX A  1    17.288 63.511 26.732 1.00 18.80
HETATM 18 C13 MTX A  1    16.845 62.195 26.688 1.00 18.10
HETATM 19 C14 MTX A  1    17.320 61.452 25.680 1.00 19.70
HETATM 20 C15 MTX A  1    18.141 62.098 24.672 1.00 17.60
HETATM 21 C16 MTX A  1    18.518 63.414 24.738 1.00 17.00
HETATM 22 C   MTX A  1    18.192 65.626 25.834 1.00 23.30
HETATM 23 O   MTX A  1    17.516 66.280 26.783 1.00 25.90
HETATM 24 N   MTX A  1    19.329 65.981 25.135 1.00 21.30
HETATM 25 CA  MTX A  1    19.837 67.459 25.135 1.00 22.60
HETATM 26 CT  MTX A  1    20.159 67.548 23.635 1.00 22.80
HETATM 27 O1  MTX A  1    20.289 66.659 22.848 1.00 21.30
HETATM 28 O2  MTX A  1    19.921 68.750 23.149 1.00 27.20
HETATM 29 CB  MTX A  1    21.217 67.669 25.761 1.00 27.40
HETATM 30 CG  MTX A  1    20.891 67.636 27.320 1.00 36.20
```

```
HETATM 31 CD  MTX A  1    19.921 68.524 28.357 1.00 41.50
HETATM 32 OE1 MTX A  1    19.413 68.371 29.593 1.00 49.10
HETATM 33 OE2 MTX A  1    19.441 69.469 27.489 1.00 42.50
CONECT  1  2 12
CONECT  2  1  3  4
CONECT  3  2
CONECT  4  2  5
CONECT  5  4  6  7
CONECT  6  5
CONECT  7  5  8 12
CONECT  8  7  9
CONECT  9  8 10 13
CONECT 10  9 11
CONECT 11 10 12
CONECT 12  1  7 11
CONECT 13  9 14
CONECT 14 13 15 19
CONECT 15 14
CONECT 16 17 21 22
CONECT 17 16 18
CONECT 18 17 19
CONECT 19 14 18 20
CONECT 20 19 21
CONECT 21 16 20
CONECT 22 16 23 24
CONECT 23 22
CONECT 24 22 25
CONECT 25 24 26 29
CONECT 26 25 27 28
CONECT 27 26
CONECT 28 26
CONECT 29 25 30
CONECT 30 29 31
CONECT 31 30 32 33
CONECT 32 31
CONECT 33 31
END
```

FIG. 6A: PDB file for a pose of methotrexate

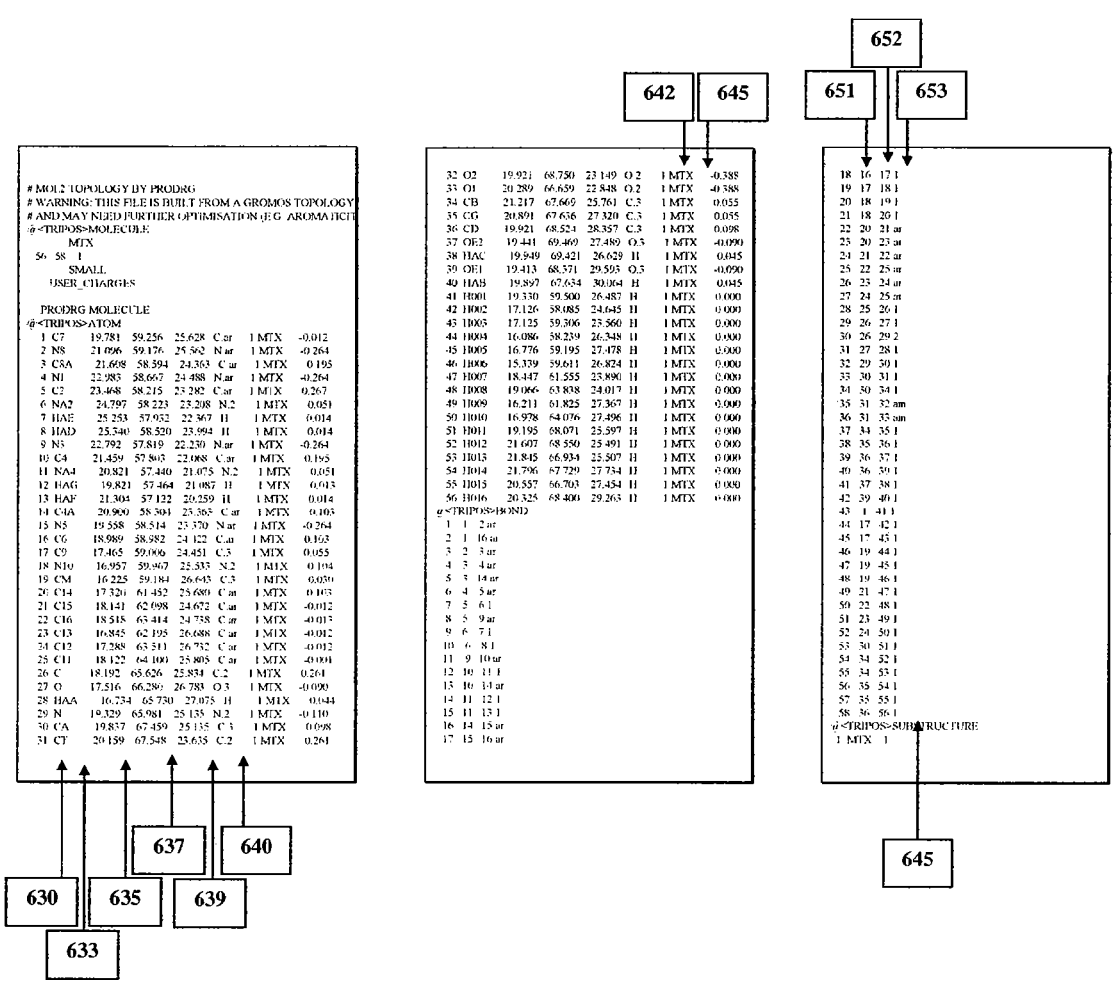
FIG. 6B: mol2 file for a pose of methotrexate

|       | 661         | 662          | 663   | 664           | 665          |
|       | ↓           | ↓            | ↓     | ↓             | ↓            |
| 4dfr Atom | Amber Atom | Charge   | Mass  | VdW Radius    | VdW Depth    |
|-------|-------------|--------------|-------|---------------|--------------|
| N1    | NT          | 0.1571       | 14.01 | 1.8240        | 0.1700       |
| C2    | CM          | -0.0211      | 12.01 | 1.9080        | 0.0860       |
| NA2   | NT          | 0.2746       | 14.01 | 1.8240        | 0.1700       |
| N3    | N2          | -0.3253      | 14.01 | 1.8240        | 0.1700       |
| C4    | CM          | 0.0724       | 12.01 | 1.9080        | 0.0860       |
| NA4   | NT          | 0.3867       | 14.01 | 1.8240        | 0.1700       |
| C4A   | CD          | -0.1444      | 12.01 | 1.9080        | 0.0860       |
| N5    | NC          | -0.0303      | 14.01 | 1.8240        | 0.1700       |
| C6    | CM          | -0.0100      | 12.01 | 1.9080        | 0.0860       |
| C7    | CM          | -0.0582      | 12.01 | 1.9080        | 0.0860       |
| N8    | NC          | 0.0543       | 14.01 | 1.8240        | 0.1700       |
| C8A   | CM          | -0.1038      | 12.01 | 1.9080        | 0.0860       |
| C9    | CT          | -0.0544      | 12.01 | 1.9080        | 0.1094       |
| N10   | N2          | 0.0215       | 14.01 | 1.8240        | 0.1700       |
| CM    | CT          | -0.0805      | 12.01 | 1.9080        | 0.1094       |
| C11   | CA          | -0.1230      | 12.01 | 1.9080        | 0.0860       |
| C12   | CA          | -0.0146      | 12.01 | 1.9080        | 0.0860       |
| C13   | CA          | -0.1936      | 12.01 | 1.9080        | 0.0860       |
| C14   | CA          | -0.0392      | 12.01 | 1.9080        | 0.0860       |
| C15   | CA          | -0.1960      | 12.01 | 1.9080        | 0.0860       |
| C16   | CA          | -0.0365      | 12.01 | 1.9080        | 0.0860       |
| C     | C           | 0.2424       | 12.01 | 1.9080        | 0.0860       |
| O     | O           | -0.4167      | 16.00 | 1.6612        | 0.2100       |
| N     | N           | 0.0791       | 14.01 | 1.8240        | 0.1700       |
| CA    | CT          | -0.1036      | 12.01 | 1.9080        | 0.1094       |
| CT    | C           | 0.4000       | 12.01 | 1.9080        | 0.0860       |
| O1    | O2          | -0.7173      | 16.00 | 1.6612        | 0.2100       |
| O2    | O2          | -0.5761      | 16.00 | 1.6612        | 0.2100       |
| CB    | CT          | -0.0699      | 12.01 | 1.9080        | 0.1094       |
| CG    | CT          | -0.2188      | 12.01 | 1.9080        | 0.1094       |
| CD    | C           | 0.4453       | 12.01 | 1.9080        | 0.0860       |
| OE1   | O2          | -0.6396      | 16.00 | 1.6612        | 0.2100       |
| OE2   | O2          | -0.5993      | 16.00 | 1.6612        | 0.2100       |

660 ↑↓

Pitzer Potential: (PK/IDIVF) * (1 + cos(PN*phi - PHASE) )

| 4dfr Bond        | Amber BOND    | IDIVF | PK    | PHASE | PN  |
|------------------|---------------|-------|-------|-------|-----|
| O2-C -CT-N       | X -C -CT-X    | 4     | 0.00  | 0.0   | 2.0 |
| O2-C -CT-CT      | X -C -CT-X    | 4     | 0.00  | 0.0   | 2.0 |
| C -CT-CT-CT      | X -CT-CT-X    | 9     | 1.40  | 0.0   | 3.0 |
| CT-CT-CT-N       | X -CT-CT-X    | 9     | 1.40  | 0.0   | 3.0 |
| CT-CT-N -C       | CT-CT-N -C    | 1     | 0.53  | 0.0   | 1.0 |
| CA-C -N -CT      | X -C -N -X    | 4     | 10.00 | 180.0 | 2.0 |
| N -C -CA-CA      | X -C -CA-X    | 4     | 14.50 | 180.0 | 2.0 |
| CA-CA-N2-CT      | X -CA-N2-X    | 4     | 9.60  | 180.0 | 2.0 |
| H -CT-N2-CT      | X -CT-N2-X    | 6     | 0.00  | 0.0   | 3.0 |
| CM-CT-N2-CT      | X -CT-N2-X    | 6     | 0.00  | 0.0   | 3.0 |
| CM-CM-CT-N2      | X -CM-CT-X    | 6     | 0.00  | 0.0   | 3.0 |

670 ↑↓

↑ ↑ ↑ ↑
672 674 676 678

FIG. 6C: Physical descriptors for methotrexate assigned according to Amber96 force field

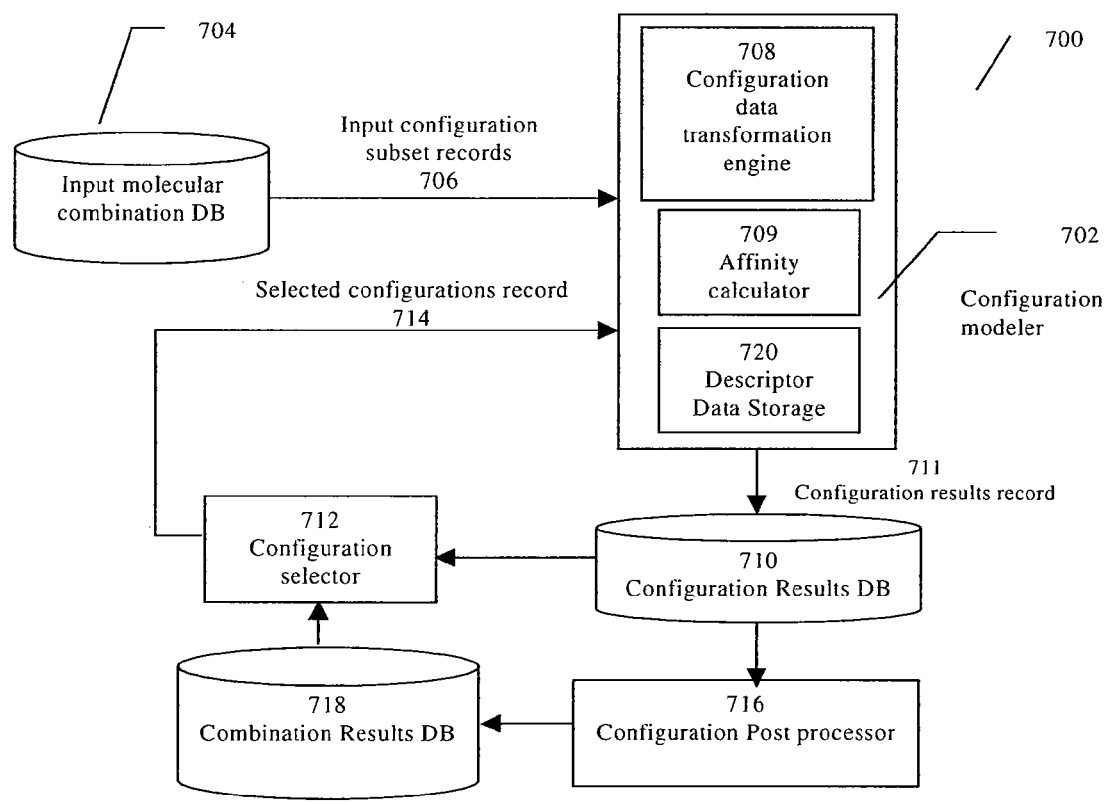
FIG. 7: Modeling system

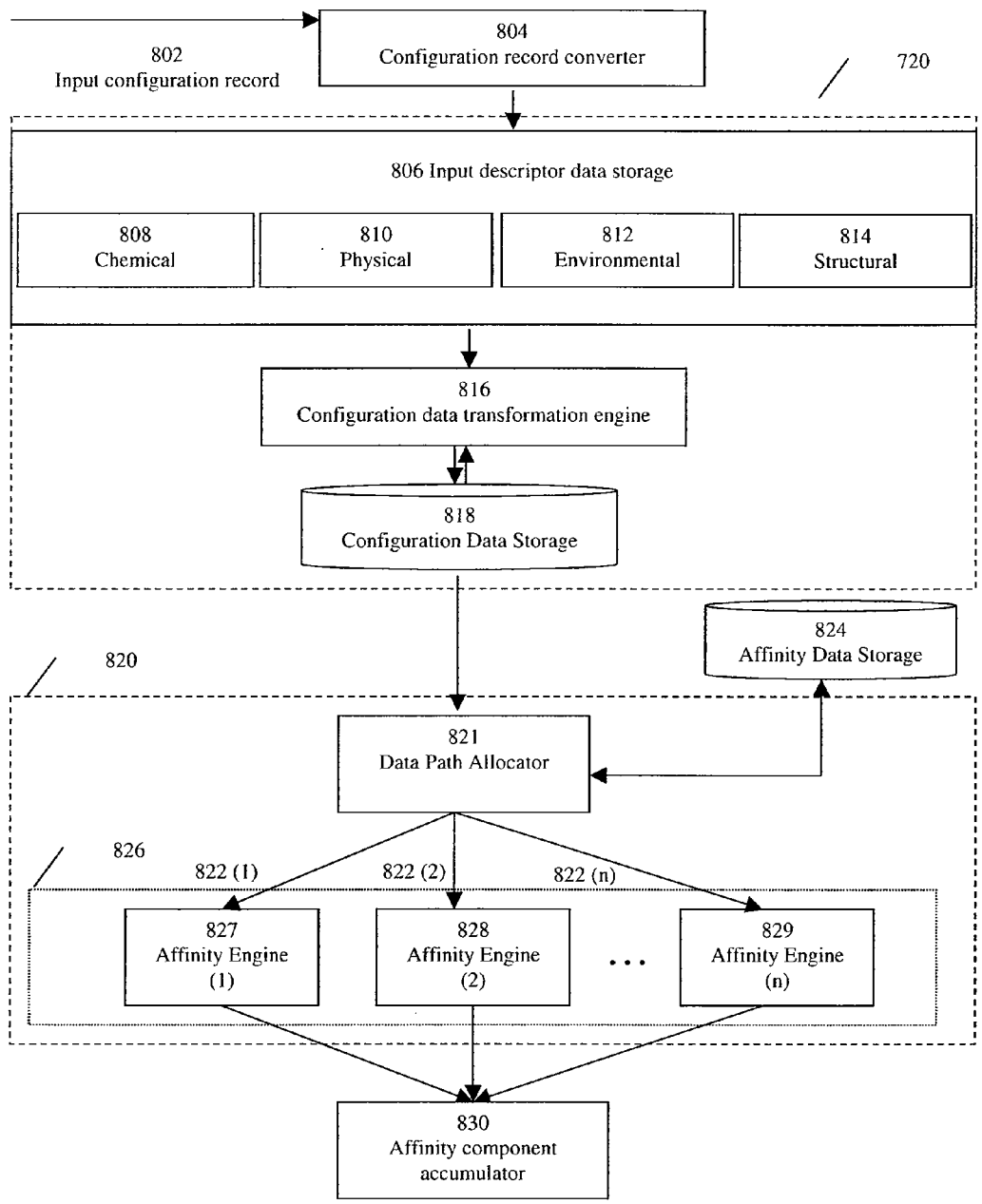
FIG. 8: Details of configuration modeler

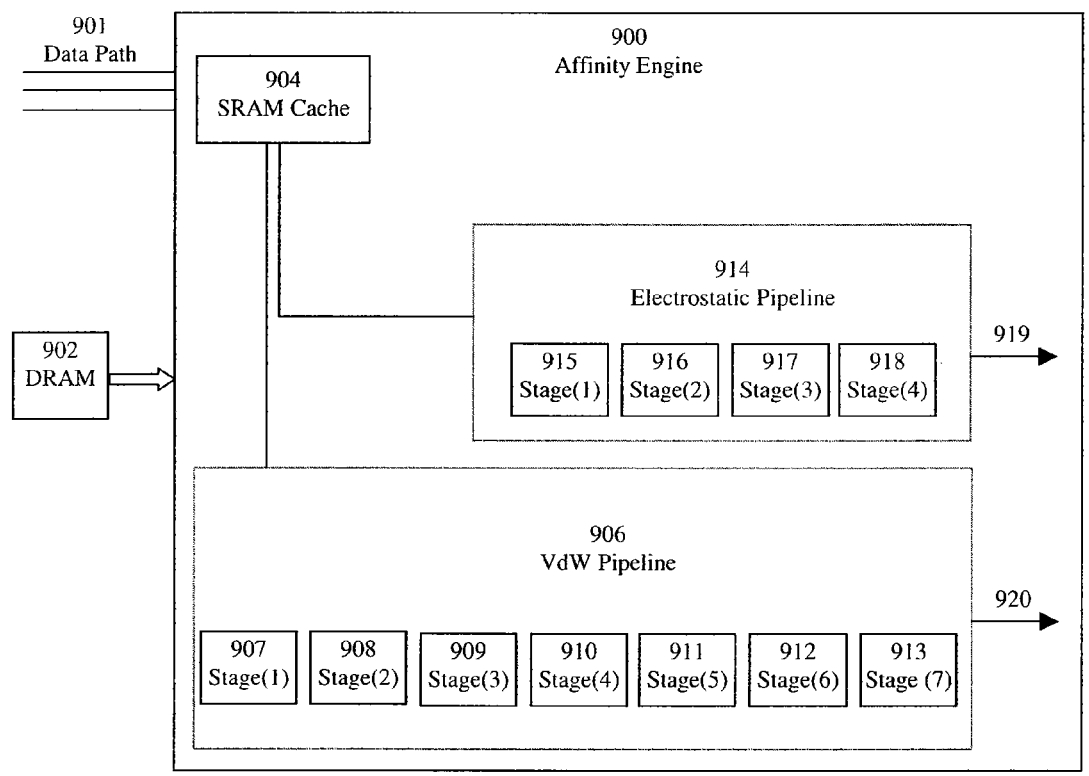
FIG. 9A: Example affinity engine demonstrating both parallelism and pipelines

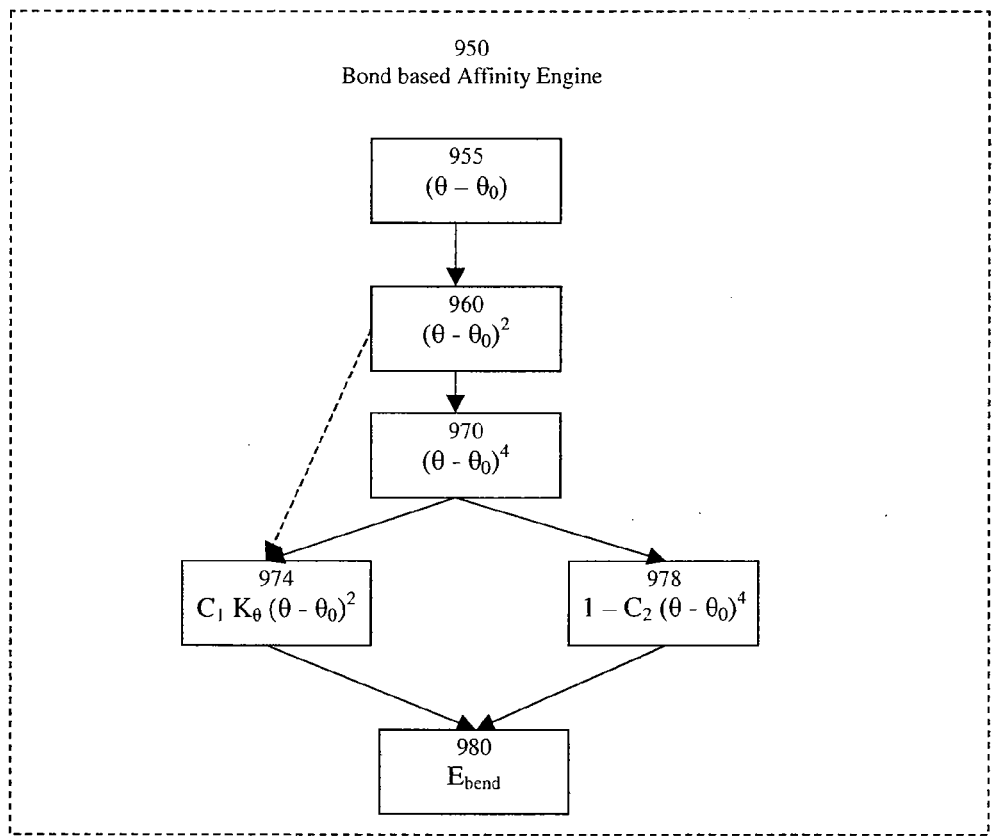
FIG. 9B: Bond based affinity engine for pipelined computation of intra-molecular strain associated with change in bond angle according to a modified harmonic bending potential, $E_{bend}$

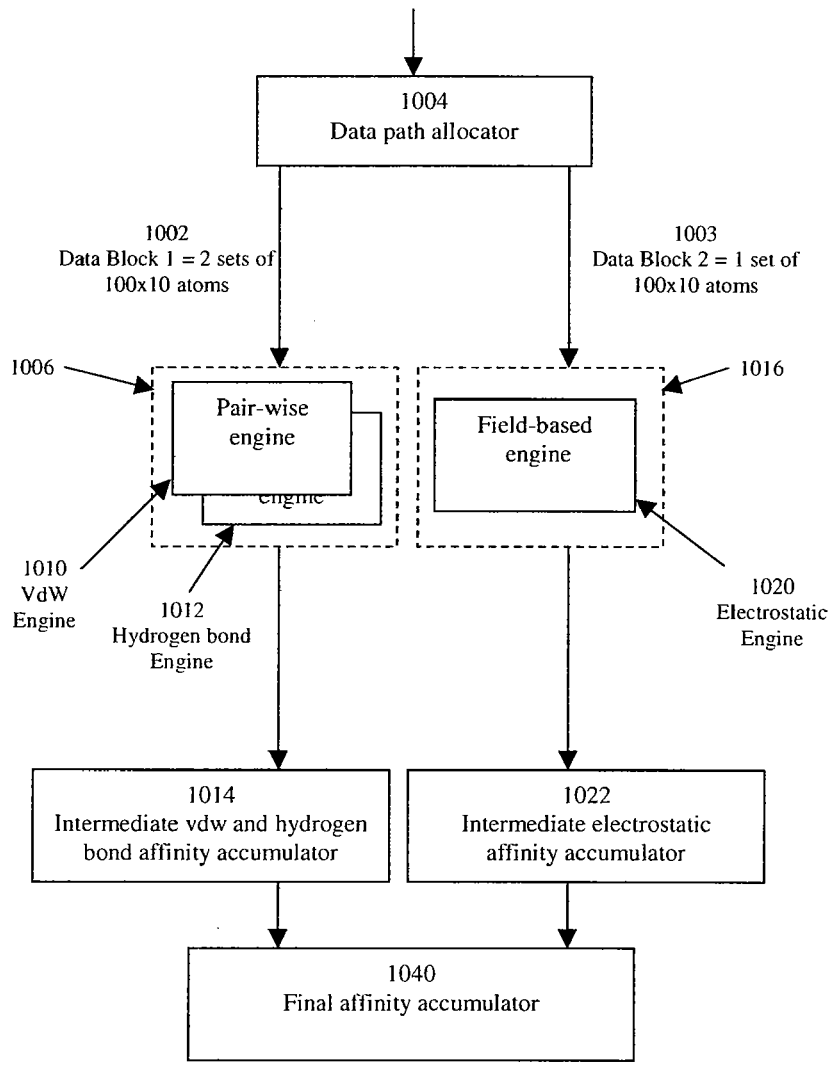
FIG. 10: Schematic of an example of a portion of a configuration modeler so as to demonstrate the concept of pipeline synchronization

METHOD AND APPARATUS FOR ANALYSIS OF MOLECULAR CONFIGURATIONS AND COMBINATIONS

CROSS-REFERENCES TO RELATED APPLICATIONS

The present application claims priority from and is a non-provisional application of U.S. Provisional Application No. 60/511,387, entitled "HARDWARE SYSTEM OPTIMIZED FOR PROCESSING MOLECULAR DOCKING CALCULATIONS" filed Oct. 14, 2003, the entire contents of which are herein incorporated by reference for all purposes.

The present disclosure is related to the following commonly assigned applications/patents:

U.S. patent application Ser. No. 10/966,041, filed of even date herewith, entitled "Method and Device for Partitioning a Molecule" to Ahuja et al. (hereinafter "Ahuja I"); and
Note: The following changes modify "FIG. 1" to become "FIGS. 1a-1f", because the six partial views of FIG. 1 have been relabeled FIG. 1A, 1B, 1C, 1D, 1E, and 1F:

The respective disclosures of these applications/patents are incorporated herein by reference in their entirety for all purposes.

FIELD OF THE INVENTION

The present invention generally relates to bioinformatics, proteomics, molecular modeling, computer-aided molecular design (CAMD), and more specifically computer-aided drug design (CADD) and computational modeling of molecular combinations.

BACKGROUND OF THE INVENTION

An explanation of conventional drug discovery processes and their limitations is useful for understanding the present invention.

Discovering a new drug to treat or cure some biological condition, is a lengthy and expensive process, typically taking on average 12 years and $800 million per drug, and taking possibly up to 15 years or more and $1 billion to complete in some cases.

A goal of a drug discovery process is to identify and characterize a chemical compound or ligand biomolecule, i.e., binder that affects the function of one or more other biomolecules (i.e., a drug "target") in an organism, usually a biopolymer, via a potential molecular interaction or combination. Herein the term biopolymer refers to a macromolecule that comprises one or more of a protein, nucleic acid (DNA or RNA), peptide or nucleotide sequence or any portions or fragments thereof. Herein the term biomolecule refers to a chemical entity that comprises one or more of a biopolymer, carbohydrate, hormone, or other molecule or chemical compound, either inorganic or organic, including, but not limited to, synthetic, medicinal, drug-like, or natural compounds, or any portions or fragments thereof.

The target molecule is typically what is known as a disease-related target protein or nucleic acid for which it is desired to affect a change in function, structure, and/or chemical activity in order to aid in the treatment of a patient disease or other disorder. In other cases, the target is a biomolecule found in a disease-causing organism, such as a virus, bacteria, or parasite, that when affected by the drug will affect the survival or activity of the infectious organism. In yet other cases, the target is a biomolecule of a defective or harmful cell such as a cancer cell. In yet other cases the target is an antigen or other environmental chemical agent that may induce an allergic reaction or other undesired immunological or biological response.

The ligand is typically a small molecule drug or chemical compound with desired drug-like properties in terms of potency, low toxicity, membrane permeability, solubility, chemical/metabolic stability, etc. In other cases, the ligand may be biologic such as an injected protein-based or peptide-based drug or even another full-fledged protein. In yet other cases the ligand may be a chemical substrate of a target enzyme. The ligand may even be covalently bound to the target or may in fact be a portion of the protein, e.g., protein secondary structure component, protein domain containing or near an active site, protein subunit of an appropriate protein quaternary structure, etc.

Throughout the remainder of the background discussion, unless otherwise specifically differentiated, a (potential) molecular combination will feature one ligand and one target, the ligand and target will be separate chemical entities, and the ligand will be assumed to be a chemical compound while the target will typically be a biological protein (mutant or wild type). Note that the frequency of nucleic acids (both DNA/RNA) as targets will likely increase in coming years as advances in gene therapy and pathogenic microbiology progress. Also the term "molecular complex" will refer to the bound state between the target and ligand when interacting with one another in the midst of a suitable (often aqueous) environment. A "potential" molecular complex refers to a bound state that may occur albeit with low probability and therefore may or may not actually form under normal conditions.

The drug discovery process itself typically includes four different subprocesses: (1) target validation; (2) lead generation/optimization; (3) preclinical testing; and (4) clinical trials and approval.

Target validation includes determination of one or more targets that have disease relevance and usually takes two-and-a-half years to complete. Results of the target validation phase might include a determination that the presence or action of the target molecule in an organism causes or influences some effect that initiates, exacerbates, or contributes to a disease for which a cure or treatment is sought. In some cases a natural binder or substrate for the target may also be determined via experimental methods.

Lead generation typically involves the identification of lead compounds, i.e., ligands, that can bind to the target molecule and that may alter the effects of the target through either activation, deactivation, catalysis, or inhibition of the function of the target, in which case the lead would be a viewed as a suitable candidate ligand to be used in the drug application process. Lead optimization involves the chemical and structural refinement of lead candidates into drug precursors in order to improve binding affinity to the desired target, increase selectivity, and also to address basic issues of toxicity, solubility, and metabolism. Together lead generation and lead optimization typically take about three years to complete and might result in one or more chemically distinct leads for further consideration.

In preclinical testing, biochemical assays and animal models are used to test the selected leads for various pharmacokinetic factors related to drug absorption, distribution, metabolism, excretion, toxicity, side effects, and required dosages. This preclinical testing takes approximately one year. After the preclinical testing period, clinical trials and approval take another six to eight or more years during which the drug candidates are tested on human subjects for safety and efficacy.

Rational drug design generally uses structural information about drug targets (structure-based) and/or their natural ligands (ligand-based) as a basis for the design of effective lead candidate generation and optimization. Structure-based rational drug design generally utilizes a three-dimensional model of the structure for the target. For target proteins or nucleic acids such structures may be as the result of X-ray crystallography/NMR or other measurement procedures or may result from homology modeling, analysis of protein motifs and conserved domains, and/or computational modeling of protein folding or the nucleic acid equivalent. Model-built structures are often all that is available when considering many membrane-associated target proteins, e.g., GPCRs and ion channels. The structure of a ligand may be generated in a similar manner or may instead be constructed ab initio from a known 2-D chemical representation using fundamental physics and chemistry principles, provided the ligand is not a biopolymer.

Rational drug design may incorporate the use of any of a number of computational components ranging from computational modeling of target-ligand molecular interactions and combinations to lead optimization to computational prediction of desired drug-like biological properties. The use of computational modeling in the context of rational drug design has been largely motivated by a desire both to reduce the required time and to improve the focus and efficiency of drug research and development, by avoiding often time consuming and costly efforts in biological "wet" lab testing and the like.

Computational modeling of target-ligand molecular combinations in the context of lead generation may involve the large-scale in-silico screening of compound libraries (i.e., library screening), whether the libraries are virtually generated and stored as one or more compound structural databases or constructed via combinatorial chemistry and organic synthesis, using computational methods to rank a selected subset of ligands based on computational prediction of bioactivity (or an equivalent measure) with respect to the intended target molecule.

Throughout the text, the term "binding mode" refers to the 3-D molecular structure of a potential molecular complex in a bound state at or near a minimum of the binding energy (i.e., maximum of the binding affinity), where the term "binding energy" (sometimes interchanged with "binding free energy" or with its conceptually antipodal counterpart "binding affinity") refers to the change in free energy of a molecular system upon formation of a potential molecular complex, i.e., the transition from an unbound to a (potential) bound state for the ligand and target. The term "system pose" is also sometimes used to refer to the binding mode. Here the term free energy generally refers to both enthalpic and entropic effects as the result of physical interactions between the constituent atoms and bonds of the molecules between themselves (i.e., both intermolecular and intramolecular interactions) and with their surrounding environment. Examples of the free energy are the Gibbs free energy encountered in the canonical or grand canonical ensembles of equilibrium statistical mechanics.

In general, the optimal binding free energy of a given target-ligand pair directly correlates to the likelihood of combination or formation of a potential molecular complex between the two molecules in chemical equilibrium, though, in truth, the binding free energy describes an ensemble of (putative) complexed structures and not one single binding mode. However, in computational modeling it is usually assumed that the change in free energy is dominated by a single structure corresponding to a minimal energy. This is certainly true for tight binders (pK~0.1 to 10 nanomolar) but questionable for weak ones (pK~10 to 100 micromolar). The dominating structure is usually taken to be the binding mode. In some cases it may be necessary to consider more than one alternative binding mode when the associated system states are nearly degenerate in terms of energy.

Binding affinity is of direct interest to drug discovery and rational drug design because the interaction of two molecules, such as a protein that is part of a biological process or pathway and a drug candidate sought for targeting a modification of the biological process or pathway, often helps indicate how well the drug candidate will serve its purpose. Furthermore, where the binding mode is determinable, the action of the drug on the target can be better understood. Such understanding may be useful when, for example, it is desirable to further modify one or more characteristics of the ligand so as to improve its potency (with respect to the target), binding specificity (with respect to other target biopolymers), or other chemical and metabolic properties.

A number of laboratory methods exist for measuring or estimating affinity between a target molecule and a ligand. Often the target might be first isolated and then mixed with the ligand in vitro and the molecular interaction assessed experimentally such as in the myriad biochemical and functional assays associated with high throughput screening. However, such methods are most useful where the target is simple to isolate, the ligand is simple to manufacture and the molecular interaction easily measured, but is more problematic when the target cannot be easily isolated, isolation interferes with the biological process or disease pathway, the ligand is difficult to synthesize in sufficient quantity, or where the particular target or ligand is not well characterized ahead of time. In the latter case, many thousands or millions of experiments might be needed for all possible combinations of the target and ligands, making the use of laboratory methods unfeasible.

While a number of attempts have been made to resolve this bottleneck by first using specialized knowledge of various chemical and biological properties of the target (or even related targets such as protein family members) and/or one or more already known natural binders or substrates to the target, to reduce the number of combinations required for lab processing, this is still impractical and too expensive in most cases. Instead of actually combining molecules in a laboratory setting and measuring experimental results, another approach is to use computers to simulate or characterize molecular interactions between two or more molecules (i.e., molecular combinations modeled in silico). The use of computational methods to assess molecular combinations and interactions is usually associated with one or more stages of rational drug design, whether structure-based, ligand-based, or both.

When computationally modeling the nature and/or likelihood of a potential molecular combination for a given target-ligand pair, the actual computational prediction of binding mode and affinity is customarily accomplished in two parts: (a) "docking", in which the computational system attempts to predict the optimal binding mode for the ligand and the target and (b) "scoring", in which the computational system attempts to refine the estimate of the binding affinity associated with the computed binding mode. During library screening, scoring may also be used to predict a relative binding affinity for one ligand vs. another ligand with respect to the target molecule and thereby rank prioritize the ligands or assign a probability for binding.

Docking may involve a search or function optimization algorithm, whether deterministic or stochastic in nature, with the intent to find one or more system poses that have favorable affinity. Scoring may involve a more refined estimation of an affinity function, where the affinity is represented in terms of a combination of one or more empirical, molecular-mechanics-based, quantum mechanics-based, or knowledge-based expressions, i.e., a scoring function. Individuals scoring functions may themselves be combined to form a more robust consensus-scoring scheme using a variety of formulations. In practice, there are many different docking strategies and scoring schemes employed in the context of today's computational drug design.

Whatever the choice of computational method there are inherent trade-offs between the computational complexity of both the underlying molecular models and the intrinsic numerical algorithms, and the amount of computing resources (time, number of CPUs, number of simulations) that must be allocated to process each molecular combination. For example, while highly sophisticated molecular dynamics simulations (MD) of the two molecules surrounded by explicit water molecules and evolved over trillions of time steps may lead to higher accuracy in modeling the potential molecular combination, the resultant computational cost (i.e., time and computing power) is so enormous that such simulations are intractable for use with more than just a few molecular combinations. On the other hand, the use of more primitive models for representing molecular interactions, in conjunction with multiple, and often error-prone, modeling shortcuts and approximations, may result in more acceptable computational cost but will invariably cause significant performance degradation in terms of modeling accuracy and predictive power. Currently, even the process of checking a library of drug candidates against a target protein takes too long for the required accuracy using current computational systems.

In general, the present invention relates to the efficient and accurate determination or characterization of molecular interactions via computational methods. Here the determination or characterization of molecular interactions (of which computational docking and scoring methods are only a subset) may involve the prediction of likelihood of formation of a potential molecular complex, the estimation of the binding affinity or binding energy of two (or more) molecules, the prediction of the binding mode (or even additional alternative modes) for the target-ligand pair, or the rank prioritization of a set of ligands based on predicted bioactivity with the target molecule. Throughout the remainder of the text, the binding affinity (or equivalent) will in general be modeled as an objective mathematical function (i.e., an 'affinity' function) that approximately characterizes the underlying physics and chemistry of the appropriate molecular interactions between the target and ligand molecules, though other possible embodiments exist (some of which will be discussed in the detailed description) wherein the affinity function may be one of a variety of qualitative or quantitative measures associated with the molecular interactions.

In summary, it is desirable in the drug discovery process to identify quickly and efficiently the optimal states or configurations, i.e., binding modes and binding energy, of two molecules or parts of molecules. Efficiency is especially relevant in the lead generation and lead optimization stages for a drug discovery pipeline, where it may be desirable to accurately predict the binding mode and binding affinity for possibly millions of potential target-ligand molecular combinations, before submitting promising candidates to further analysis. There is a clear need then to have more efficient systems and methods for computational modeling of the molecular combinations with reasonable accuracy.

REFERENCES & PRIOR ART

Prior art in the field of the current invention is heavily documented: the following tries to summarize it.

Drews [1] provides a good overview of the current state of drug discovery. In [2] Abagyan and Totrov show the state of high throughput docking and scoring and its applications. Lamb et al. [3] further teach a general approach to the design, docking, and virtual screening of multiple combinatorial libraries against a family of proteins, finally Waskowycz et al. [4] describe the use of multiple computers to accelerate virtual screening of a large ligand library against a specific target by assigning groups of ligands to specific computers.

[1] J. Drews, "Drug Discovery: A Historical perspective", *Science,* 287, 1960-1964 (2000).

[2] Ruben Abagyan and Maxim Totrov, "High-throughput docking for lead generation", *Current Opinion in Chemical Biology*, Vol. 5, 375-382 (2001).

[3] Lamb, M. L., Burdick, K. W., Toba, S., Young, M. M., Skillman, A. G. et al., "Design, docking, and evaluation of multiple libraries against multiple targets", *Proteins,* Vol. 42, 296-318 (2001).

[4] Waszkowycz, B., Perkins, T. D. J., Sykes, R. A., Li, J., "Large-scale virtual screening for discovering leads in the postgenomic era", IBM Systems Journal, Vol. 40, No. 2 (2001).

There are a number of examples of software tools currently used to perform docking simulations. These methods involve a wide range of computational techniques, including use of a) rigid-body pattern-matching algorithms, either based on surface correlations, use of geometric hashing, pose clustering, or graph pattern-matching; b) fragmnental-based methods, including incremental construction or 'place and join' operators; c) stochastic optimization methods including use of Monte Carlo, simulated annealing, or genetic (or memetic) algorithms; d) molecular dynamics simulations or e) hybrids strategies derived thereof.

The earliest docking software tool was a graph-based rigid-body pattern-matching algorithm called DOCK [5][6][6], developed at UCSF back in 1982 (v1.0) and now up to v5.0 (with extensions to include incremental construction). Other examples of graph-based pattern-matching algorithms include CLIX [8] (which in turn uses GRID [9]), FLOG [10] and LIGIN [11].

[5] Shoichet, B. K., Bodian, D. L. and Kuntz, I. D., "Molecular docking using shape descriptors", *J Comp Chem,* Vol. 13 No. 3, 380-397 (1992).

[6] Meng, E. C., Gschwend, D. A., Blaney, J. M., and I. D. Kuntz, "Orientational sampling and rigid-body minimization in molecular docking", *Proteins: Structure, Function, and Genetics*, Vol. 17, 266-278 (1993).

[7] Ewing, T. J. A. and Kuntz, I. D., "Critical Evaluation of Search Algorithms for Automated Molecular Docking and Database Screening", *J. Computational Chemistry*, Vol. 18 No. 9, 1175-1189 (1997).

[8] Lawrence, M. C. and Davis, P. C.; "CLIX: A Search Algorithm for Finding Novel Ligands Capable of Binding Proteins of Known Three-Dimensional Structure", *Proteins,* Vol. 12, 31-41 (1992).

[9] Kastenholz, M. A., Pastor, M., Cruciani, G., Haaksma, E. E. J., Fox, T., "GRID/CPCA: A new computational tool to design selective ligands", *J. Medicinal Chemistry,* Vol. 43, 3033-3044 (2000).

[10] Miller, M. D., Kearsley, S. K., Underwood, D. J. and Sheridan, R. P., "FLOG: a system to select 'quasi-flexible' ligands complementary to a receptor of known three-dimensional structure", *J. Computer-Aided Molecular Design*, Vol. 8 No. 2, 153-174 (1994).

[11] Sobolev, V., Wade, R. C., Vriend, G. and Edelman, M., "Molecular docking using surface complementarity", *Proteins*, Vol. 25, 120-129 (1996). Other rigid-body pattern-matching docking software tools include the shape-based correlation methods of FTDOCK [12] and HEX [13], the geometric hashing of Fischer et al. [14], or the pose clustering of Rarey et al. [15].

[12] Aloy, P., Moont, G., Gabb, H. A., Querol, E., Aviles, F. X., and Sternberg, M. J. E., "Modeling Protein Docking using Shape Complementarity, Electrostatics and Biochemical Information," *Proteins: Structure, Function, and Genetics*, Vol. 33, 535-549 (1998).

[13] Ritchie, D. W. and Kemp. G. J. L., "Fast Computation, Rotation, and Comparison of Low Resolution Spherical Harmonic Molecular Surfaces", *Proteins: Structure, Function, and Genetics*, Vol. 39, 178-194 (2000).

[14] Fischer, D., Norel, R., Wolfson, H. and Nussinov, R., "Surface motifs by a computer vision technique: searches, detection, and implications for protein-ligand recognition", *Proteins*, Vol. 16, 278-292 (1993).

[15] Rarey, M., Wefing, S., and Lengauer, T., "Placement of medium-sized molecular fragments into active sites of proteins", *J. Computer-Aided Molecular Design*, Vol. 10, 41-54 (1996).

In general, rigid-body pattern-matching algorithms assume that both the target and ligand are rigid (i.e., not flexible) and hence may be appropriate for docking small, rigid molecules (or molecular fragments) to a simple protein with a well-defined, nearly rigid active site. Thus this class of docking tools may be suitable for de novo ligand design, combinatorial library design, or straightforward rigid-body screening of a molecule library containing multiple conformers per ligand.

Incremental construction based docking software tools include FlexX [16][17] from Tripos (licensed from EMBL), Hammerhead [18], DOCK v4.0 [6] (as an option), and the nongreedy, backtracking algorithm of Leach et al. [19]. Programs using incremental construction in the context of de novo ligand design include LUDI [20] (from Accelrys) and GrowMol [21]. Docking software tools based on 'place and join' strategies include DesJarlais et al. [22].

[16] Kramer, B., Rarey, M. and Lengauer, T., "Evaluation of the FlexX incremental construction algorithm for protein-ligand docking", *Proteins*, Vol. 37, 228-241 (1999).

[17] Rarey, M., Kramer, B., Lengauer, T., and Klebe, G., "A Fast Flexible Docking Method Using An Incremental Construction Algorithm", *J. Mol. Biol.*, Vol. 261, 470-489 (1996).

[18] Welch, W., Ruppert, J. and Jain, A. N., "Hammerhead: Fast, fully automated docking of flexible ligands to protein binding sites", *Chemical Biology*, Vol. 3, 449-462 (1996).

[19] Leach, A. R., Kuntz, I. D., "Conformational Analysis of Flexible Ligands in Macromolecular Receptor Sites", *J. Comp. Chem.*, Vol. 13, 730-748 (1992).

[20] Bohm, H. J., "The computer program LUDI: a new method for the de novo design of enzyme inhibitors", *J. Computer-Aided Molecular Design*, Vol. 6, 61-78 (1992).

[21] Bohacek, R. S. and McMartin, C., "Multiple Highly Diverse Structures Complementary to Enzyme Binding Sites: Results of Extensive Application of a de Novo Design Method Incorporating Combinatorial Growth", *J. American Chemical Society*, Vol. 116, 5560-5571 (1994).

[22] DesJarlais, R. L., Sheridan, R. P., Dixon, J. S., Kuntz, I. D., and Venkataraghavan, R., "Docking Flexible Ligands to Macromolecular Receptors by Molecular Shape", *J. Med. Chem.*, Vol. 29, 2149-2153 (1986).

Incremental construction algorithms may be used to model docking of flexible ligands to a rigid target molecule with a well-characterized active site. They may be used when screening a library of flexible ligands against one or more targets. They are often comparatively less compute intensive, yet consequently less accurate, than many of their stochastic optimization based competitors. However, even FlexX may take on order of <1-2 minutes to process one target-ligand combination and thus may still be computationally onerous depending on the size of the library (e.g., tens of millions or more compounds). Incremental construction algorithms often employ one or more scoring functions to evaluate and rank different system poses encountered during computations. Recently FlexX was extended to FlexE [23] to attempt to account for partial flexibility of the target molecule's active site via use of user-defined ensembles of certain active site rotamers.

[23] Claussen, H., Buning, C., Rarey, M., and Lengauer, T., "FlexE: Efficient Molecular Docking Considering Protein Structure Variations", *J. Molecular Biology*, Vol. 308, 377-395 (2001).

Computational docking software tools based on stochastic optimization include ICM [24] (from MolSoft), GLIDE [25] (from Schrodinger), and LigandFit [26] (from Accelrys), all based on modified Monte Carlo techniques, and AutoDock v.2.5 [27] (from Scripps Institute) based on simulated annealing. Others based on genetic or memetic algorithms include GOLD [28][29], DARWIN [30], and AutoDock v.3.0 [31] (also from Scripps).

[24] Abagyan, R. A., Totrov, M. M., and Kuznetsov, D. N., "Biased probability Monte Carlo conformational searches and electrostatic calculations for peptides and proteins", *J. Comp. Chem.*, Vol. 15, 488-506 (1994).

[25] Halgren, T. A., Murphy, R. B., Friesner, R. A., Beard, H. S., Frye, L. L., Pollard, W. T., and Banks, J. L., "Glide: a new approach for rapid, accurate docking and scoring. 2. Enrichment factors in database screening", *J Med Chem.*, Vol. 47 No. 7, 1750-1759, (2004).

[26] Luty, B. A., Wasserman, Z. R., Stouten, P. F. W., Hodge, C. N., Zacharias, M., and McCammon, J. A., "Molecular Mechanics/Grid Method for the Evaluation of Ligand-Receptor Interactions", *J. Comp. Chem.*, Vol. 16, 454-464 (1995).

[27] Goodsell, D. S. and Olson, A. J., "Automated Docking of Substrates to Proteins by Simulated Annealing", *Proteins: Structure, Function, and Genetics*, Vol. 8, 195-202 (1990).

[28] Jones, G., Willett, P. and Glen, R. C., "Molecular Recognition of Receptor Sites using a Genetic Algorithm with a Description of Desolvation", *J. Mol. Biol.*, Vol. 245, 43-53 (1995).

[29] Jones, G., Willett, P., Glen, R. C., Leach, A., and Taylor, R., "Development and Validation of a Genetic Algorithm for Flexible Docking", *J. Mol. Biol.*, Vol. 267, 727-748 (1997).

[30] Taylor, J. S. and Burnett, R. M., *Proteins*, Vol. 41, 173-191 (2000).

[31] Morris, G. M., Goodsell, D. S., Halliday, R. S., Huey, R., Hart, W. E., Belew, R. K. and Olson, A. J., "Automated Docking Using a Lamarckian Genetic Algorithm and an Empirical Binding Free Energy Function", *J. Comp. Chem.*, Vol. 19, 1639-1662 (1998).

Stochastic optimization-based methods may be used to model docking of flexible ligands to a target molecule. They generally use a molecular-mechanics-based formulation of the affinity function and employ various strategies to search for one or more favorable system energy minima. They are often more compute intensive, yet also more robust, than their incremental construction competitors. As they are stochastic in nature, different runs or simulations may often result in different predictions. Traditionally most docking software tools using stochastic optimization assume the target to be nearly rigid (i.e., hydrogen bond donor and acceptor groups in the active site may rotate), since otherwise the combinatorial complexity increases rapidly making the problem difficult to robustly solve in reasonable time.

Molecular dynamics simulations have also been used in the context of computational modeling of target-ligand combinations. This includes the implementations presented in Di Nola et al. [32] and Luty et al. [16] (along with Monte Carlo). In principle, molecular dynamics simulations may be able to model protein flexibility to an arbitrary degree. On the other hand, they may also require evaluation of many fine-grained, time steps and are thus often very time-consuming (one order of hours or even days per target-ligand combination). They also often require user interaction for selection of valid trajectories. Use of molecular dynamics simulations in lead discovery is therefore more suited to local minimization of predicted complexes featuring a small number of promising lead candidates.

[32] Di Nola, A., Berendsen, H. J. C., and Roccatano, D., "Molecular Dynamics Simulation of the Docking of Substrates to Proteins", *Proteins*, Vol. 19, 174-182 (1994).

Hybrid methods may involve use of rigid-body pattern-matching techniques for fast screening of selected low-energy ligand conformations, followed by Monte Carlo torsional optimization of surviving poses, and finally even molecular dynamics refinement of a few choice ligand structures in combination with a (potentially) flexible protein active site. An example of this type of docking software strategy is Wang et al. [33].

[33] Wang, J., Kollman, P. A. and Kuntz, I. D., *Proteins*, Vol. 36, 1-19 (1999). There are a number of examples of scoring functions implemented in software and used to estimate target-ligand affinity, rank prioritize different ligands as per a library screen, or rank intermediate docking poses in order to predict binding modes. Scoring functions traditionally fall into three distinct categories: a) empirical scoring functions, b) molecular-mechanics-based expressions, or (c) knowledge-based scoring functions or hybrid schemes derived thereof.

Empirically derived scoring functions (as applied to target-ligand combinations) were first inspired by the linear free-energy relationships often utilized in QSAR studies. An early example is that of Böhm et al. [20][34] (used in LUDI). Other empirical scoring functions include SCORE [35] (used in FlexX), ChemScore [36], PLP [37], Fresno [38], and GlideScore v.2.0+ [39] (modified form of ChemScore, used by GLIDE).

[34] Böhm, H. J., "The Development of a simple empirical scoring function to estimate the binding constant for a protein-ligand complex of known three-dimensional structure", *J. Comput-Aided Mol. Des.*, Vol. 8, 243-256 (1994).

[35] Wang, R., Gao, Y. and Lai, L., "A new empirical method for estimating the binding affinity of a protein-ligand complex.", *J. Molecular Modeling*, Vol. 4, 379 (1998).

[36] Eldridge, M. D., Murray, C. W., Auton, T. R., Paolini, G. V., and Mee, R. P., "Empirical scoring functions: I. The development of a fast empirical scoring function to estimate the binding affinity of ligands in receptor complexes", *J. Computer-Aided Molecular Design*, Vol. 11, 425-445 (1997).

[37] Gelhaar, D. K., Bouzida, D.; Rejto, P. A., In "*Rational Drug Design: Novel Methodology and Practical Applications*", Parrill, L., Reddy, M. R., Ed.; American Chemical Society: Washington, D.C., pp. 292-311 (1999).

[38] Rognan D., Lauemoller S. L., Holm A., Buus S., Schinke V., *J. Medicinal Chemistry*, Vol. 42, 4650-4658 (1999).

[39] Halgren, T. A., Murphy, R. B., Friesner, R. A., Beard, H. S., Frye, L. L., Pollard, W. T., and Banks, J. L., "Glide: a new approach for rapid, accurate docking and scoring. 2. Enrichment factors in database screening", *J Med Chem.*, Vol. 47 No. 7, 1750-1759 (2004).

In general, empirical scoring functions comprise the bulk of scoring functions used today, especially in the context of large compound library screening. The basic premise is to calibrate a linear combination of empirical energy models, each multiplied by an associated numerical weight and each representing one of a set of interaction components represented in a (so-called) 'master scoring equation', where said equation attempts to well approximate the binding free energy of a molecular combination. The numerical weight factors may be obtained by fitting to experimental binding free energy data composed for a training set of target-ligand complexes.

Molecular-mechanics-based scoring functions were first developed for use in molecular modeling in the context of molecular mechanics force fields like AMBER [40][41], OPLS [42], MMFF [43], and CHARMM [44]. Examples of molecular-mechanics-based scoring functions include both the chemical and energy-based scoring functions of DOCK v.4.0 (based on AMBER) [6], the objective functions used in GOLD [28][29], AutoDock v.3.0 [31] (with empirical weights), and FLOG [10].

[40] Pearlman, D. A., Case, D. A., Caldwell, J. C., Ross, W. S., Cheatham III, T. E., Ferguson, D. M., Seibel, G. L., Singh, U. C., Weiner, P., Kollman, P. A. *AMBER* 4.1, University of California, San Francisco (1995).

[41] Cornell, W. D., Cieplak, P., Bayly, C. I., Goulg, I. R., Merz, K. M., Ferguson, D. M., Spellmeyer, D. C., Fox, T., Caldwell, J. W., Kollman, P. A., "A second-generation force field for the simulation of proteins, nucleic acids, and organic molecules", *J. American Chemical Society*, Vol. 117, 5179-5197 (1995).

[42] Jorgensen, W. L., & Tirado-Rives, J., *J. American Chemical Society*, Vol. 110, 1657-1666 (1988).

[43] Halgren, T. A., "Merck Molecular Force Field. 1. Basis, Form, Scope, Parameterization, and Performance of MMFF94", *J. Comp. Chem.*, Vol. 17, 490-519 (1996).

[44] Brooks, B. R., Bruccoleri, R. E., Olafson, B. D., States, D. J., Swaminathan, S. and Karplus, M., "CHARMM: A Program for Macromolecular Energy, Minimization, and Dynamics Calculations", J. Comp. Chem., Vol. 4, 187-217 (1983).

In general, molecular-mechanics-based scoring functions may closely resemble the objective functions utilized by many stochastic optimization-based docking programs. Such functions typically require atomic (or chemical group) level parameterization of various attributes (e.g., charge, mass, vdW radii, bond equilibrium constants, etc.) based on one or more molecular mechanics force fields (e.g., AMBER, MMFF, OPLS, etc.). In some cases, the relevant parameters for the ligand may also be assigned based on usage of other molecular modeling software packages, e.g., ligand partial charges assigned via use of MOPAC [45], AMPAC [46] or AMSOL [47]. They may also include intramolecular interactions (i.e., self-energy of molecules), as well as long range interactions such as electrostatics. In some cases, the combination of energy terms may again be accomplished via numerical weights optimized for reproduction of test ligand-target complexes.

[45] Stewart, J. J. P., *Quantum Chemistry Program Exchange*, Vol. 10:86 (1990).

[46] Liotard, D. A., Healy, E. F., Ruiz, J. M., and Dewar, M. J. S., *Quantum Chemistry Program Exchange*—no. 506, QCPE Bulletin, Vol. 9: 123 (1989).

[47] AMSOL—version 6.5.1 by G. D. Hawkins, D. J. Giesen, G. C. Lynch, C. C. Chambers, I. Rossi, J. W. Storer, J. Li, D. Rinaldi, D. A. Liotard, C. J. Cramer, and D. G. Truhlar, University of Minnesota, Minneapolis (1997).

Knowledge-based scoring functions were first inspired by the potential of mean force statistical mechanics methods for modeling liquids. Examples include DrugScore [48], PMF [49], and BLEEP [50].

[48] Gohlke, H., Hendlich, M. and Klebe, G., "Knowledge-based Scoring Function to Predict Protein-Ligand Interactions", *J. Mol. Biol.*, Vol. 295, 337-356 (2000).

[49] Muegge, I. and Martin, Y. C., "A general and fast scoring function for protein-ligand interactions—a simplified potential approach.", *J. Med. Chem.*, Vol. 42, 791-804 (1999).

[50] Mitchell, J. B. O., Laskowski, R. A., Alex, A. and Thornton, J. M., "BLEEP—Potential of Mean Force Describing Protein-Ligand Interactions II. Calculation of Binding Energies and Comparison with Experimental Data", *J. Comp. Chem.*, Vol. 20, 1165-1176 (1999).

In general, knowledge-based scoring functions do not require partitioning of the affinity function. However, they do require usage of a large database of 3-D structures of relevant molecular complexes. There is also usually no need for regression against a data set of molecular complexes with known experimental binding affinities. These methods are based on the underlying assumption that the more favorable an interaction is between two atoms, at a given distance, the more frequent its occurrence relative to expectations in a bulk, disordered medium. These schemes are sometimes referred to as 'inverse Boltzmann' schemes, but in fact the presence of local, optimized structures in macromolecules and protein folds means that distance-dependent pair-wise preference distributions need not be strictly Boltzmann. It is also possible to introduce the concept of singlet preferences based on other molecular descriptors, e.g., solvent accessible surface area for approximation of solvation effects.

Hybrid scoring functions may be a mixture of one or more scoring functions of distinct type. One example is VALIDATE [51], which is a molecular-mechanics/empirical hybrid function. Other combinations of scoring functions may include the concept of consensus scoring in which multiple functions may be evaluated for each molecular combination and some form of 'consensus' decision is made based on a set of rules or statistical criteria, e.g., states that occur in the top 10% rank list of each scoring function (intersection-based), states that have a high mean rank (average-based), etc. A useful review discussion of consensus scoring can be found in Bissantz et al. [52].

[51] Head, R. D., Smythe, M. L., Oprea, T. I., Waller, C. L., Green, S. M. and Marshall, G. R., "VALIDATE: A New Method for Receptor-Based Prediction of Binding Affinities of Novel Ligand", *J. American Chemical Society*, Vol. 118, 3959-3969 (1996).

[52] Bissantz, C., Folkers, G., Rognan, D., "Protein-based virtual screening of chemical databases. 1. Evaluation of different docking/scoring combinations", *J Med Chem,* Vol. 43, 4759-4767 (2000). However, none of the current computational tools available for modeling of target-ligand molecular combinations provide both the necessary accuracy and speed as required in today's drug discovery in order to enable the efficient large-scale screening of potential drug candidates.

Various file formats exist for the digital representation of structural and chemical information for both target proteins and compounds as related to structural databases. Examples include the pdb, mol2 (from Tripos), and the SMILES formats.

[53] Westbrook, J. and Fitzgerald, P. M. (2003): *Structural Bioinformatics*, P. E. Bourne and H. Weissig (editors). Hoboken, N.J., John Wiley & Sons, Inc. pp. 161-179.

[54] The .mol2 file format is a molecular file format from Tripos used in a number of molecular modeling applications.

[55] SMILES is a standard molecular representation language licensed by the company Daylight.

[56] Clark, M., Cramer, R. D., Opdenbosch, N. V., "Validation of the General Purpose Tripos 5.2 Force Field", *J. Comp. Chem.*, Vol. 10, 982-1012 (1989).

[57] CORINA is a software package for generation of 3-D coordinates of molecules licensed by Molecular Networks Inc.

A discussion on the calculation of total electrostatic energies involved in the formation of a potential molecular complex can be found in Gilson et al. [58]. Computational solutions of electrostatic potentials in the classical regime range from simpler formulations, like those involving distance-dependent dielectric functions [59] to more complex formulations, like those involving solution of the Poisson-Boltzmann equation [60][61], a second order, generally nonlinear, elliptic partial differential equation.

Other classical formalisms that attempt to model electrostatic desolvation include those based on the Generalized Born solvation model [62][63], methods that involve representation of reaction field effects via additional solvent accessible or fragmental volume terms [64][65][66], or explicit representation of solvent in the context of molecular dynamics simulations [67][68][69]. A lengthy review of full quantum mechanical treatment of electrostatics interactions can be found in Labanowksi et al. [70].

[58] Gilson, M. K., and Honig, B., "Calculation of the Total Electrostatic Energy of a Macromolecular System: Solvation Energies, Binding Energies, and Conformational Analysis", *Proteins*, Vol. 4, 7-18 (1988).

[59] Mehler, E. L. and Solmajer, T., "Electrostatic effects in proteins: comparison of dielectric and charge models" *Protein Engineering*, Vol. 4, 903-910 (1991).

[60] Holst, M., Baker, N., and Wang, F., "Adaptive Multilevel Finite Element Solution of the Poisson-Boltzmann Equations I. Algorithms and Examples", *J. Comp. Chem.,* Vol. 21, No. 15, 1319-1342 (2000).

[61] Nicholls, A., and Honig, B., "A Rapid Finite Difference Algorithm, Utilizing Successive Over-Relaxation to Solve Poisson-Boltzmann Equation", *J. Comp. Chem.*, Vol. 12, No. 4, 435-445 (1991)

[62] Still, W. C., Tempczyk, A., Hawley, R. C. and Hendrickson, T., "A General Treatment of Solvation for Molecular Mechanics", *J. Am. Chem. Soc.*, Vol. 112, 6127-6129 (1990).

[63] Ghosh, A., Rapp, C. S., and Friesner, R. A., "A Generalized Born Model Based on Surface Integral Formulation", *J. Physical Chemistry B.*, Vol. 102,10983-10 (1988). Eisenberg, D., and McLachlan, A. D., "Solvation Energy in Protein Folding and Binding", *Nature*, Vol. 31, 3086 (1986).

[65] Privalov, P. L., and Makhatadze, G. I., "Contribution of hydration to protein folding thermodynamics", *J. Mol. Bio.*, Vol. 232, 660-679 (1993).

[66] Stouten, P. F. W., Frömmel, C., Nakamura, H., and Sander, C., "An effective salvation term based on atomic occupancies for use in protein simulations", *Molecular Simulation*, Vol. 10, No. 2-6, 97-120 (1993).

[67] Bash, P., Singh, U. C., Langridge, R., and Kollman, P., "Free Energy Calculation by Computer Simulation", *Science*, Vol. 236, 564 (1987).

[68] Jorgensen, W. L., Briggs, J. M., and Contreras, M. L., "Relative Partition Coefficients for Organic Solutes from Fluid Simulations", *J. Phys. Chem.*, Vol. 94, 1683-1686 (1990).

[69] Jackson, R. M., Gabb, H. A., and Sternberg, M. J. E., "Rapid Refinement of Protein Interfaces Incorporating Solvation: Application to the Docking Problem", *J. Mol. Biol.*, Vol. 276, 265-285 (1998).

[70] Labanowski and J. Andzelm, editors, "Density Functional Methods in Chemistry", Springer-Verlag, New York (1991).

BRIEF SUMMARY OF THE INVENTION

Aspects of the present invention relate to a method and apparatus for the efficient computation of affinity functions for two or more molecular subsets of a molecular configuration, wherein either one or both molecular subsets are from a plurality of molecular subsets selected from a molecule library, based on a calculation means comprising a plurality of parallel pipelines. Other aspects of the invention relate to synchronization of the parallel affinity pipelines in order to maximize utilization of processing power available to the calculation means. Further aspects of the invention relate to the use of a data path allocation means to apportion molecular descriptor data to each affinity engine as one or more data blocks according to a data path schedule. Further embodiments of the invention will also be discussed relating to use of the invention in the context of analysis of molecular combinations including provisions for efficient generation of new configurations from one or more input configurations, computation of a plurality of affinity functions for a plurality of configurations, and subsequent selection of processed configurations for further analysis, as well as several embodiments involving iterative use of the invention in the context of a search or optimization strategy. Moreover, various embodiments of the invention relating to efficient implementation of the invention in the context of a hardware apparatus are also discussed.

BRIEF DESCRIPTION OF THE DRAWINGS

A more complex appreciation of the invention and many of the advantages thereof will be readily obtained, as the same becomes better understood by references to the detailed description when considered in connection with the accompanying drawings, wherein:

FIGS. 2a, 2b, and 2c respectively show a 2-D schematic representation of methotrexate, a 'ball and stick' representation of conformation of methotrexate, and another conformation of methotrexate that differs from that depicted in FIG. 2b by changes to two torsional degrees of freedom.

FIGS. 3a, 3b, and 3c respectively show a 'ball and stick' representation of a pose of methotrexate with an attached Cartesian frame aligned with a global 3-D coordinate system, a 'ball and stick' representation of another pose of methotrexate after both translation and rigid body rotation, and lastly 'ball and stick' representation of yet another pose of methotrexate also involving changes in conformation.

FIGS. 4a, 4b, and 4c illustrate example configurations of a molecular combination featuring methotrexate and the protein dihydrofolate reductase. FIG. 4a depicts a 'ball and stick' representation of a pose of methotrexate and a pose of the protein dihydrofolate reductase as represented by a portion of the solvent accessible surface associated with the active site. FIG. 4b depicts another configuration featuring the same pose of the protein (as in FIG. 4a) but for a different pose of methotrexate. Lastly FIG. 4c depicts yet another configuration but now featuring different poses for both the protein and for methotrexate.

FIG. 5 is an illustration of a plurality of torsional degrees of freedom associated with the methotrexate molecule.

FIGS. 6a, 6b, and 6c respectively show a digital representation of a pose of methotrexate in the form of a pdb-formatted file, another digital representation of the same pose of methotrexate in the form of a mol2 formatted file, and file listing a set of physical descriptors for the methotrexate atoms and bonds assigned according to an Amber96 force field.

FIG. 7 is a schematic of an embodiment of a modeling system for the analysis of molecular combinations as relates to the current invention.

FIG. 8 is a more detailed schematic of an embodiment of a configuration modeler, including both a configuration data transformation engine and an affinity calculator, as part of a modeling system for the analysis of molecular combinations as relates to the current invention.

FIG. 9a is a schematic of an example embodiment of an affinity engine featuring two parallel pipelines, one dedicated to electrostatic computations and the other to vdW computations, so as to demonstrate concepts of pipelines, parallelism, and synchronization.

FIG. 9b is a schematic of an example embodiment of a bond based affinity engine for efficient pipelined computation of the intramolecular strain energy associated with changes in one or more bond angles in a molecular configuration, according to a modified harmonic bending potential.

FIG. 10 is a schematic of an example embodiment of a portion of a configuration modeler including a data path allocation means, two distinct data paths, two groups of affinity engines operating in parallel representing the calculation means, and an accumulation means, so as to further demonstrate the concept of pipeline synchronization.

DETAILED DESCRIPTION OF THE INVENTION

Figure 1A:
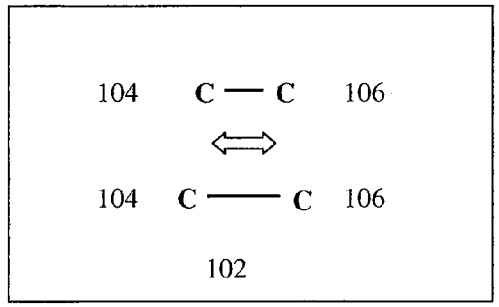
FIGS. 1a-1f illustrate some examples of conformational degrees of freedom associated with possible changes in structure of a molecular conformation.
Figure 1B:
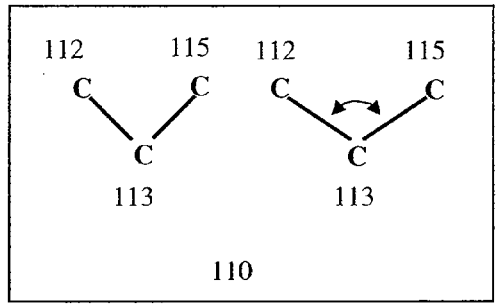
Figure 1C:
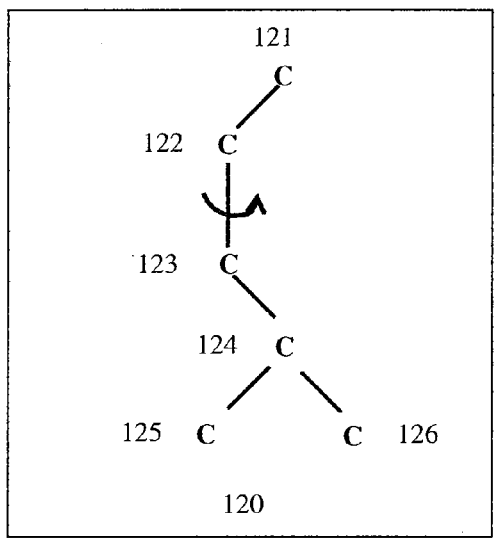

The present invention has many applications, as will be apparent after reading this disclosure. In describing an embodiment of a computational system according to the present invention, only a few of the possible variations are described. Other applications and variations will be apparent to one of ordinary skill in the art, so the invention should not be construed as narrowly as the examples, but rather in accordance with the appended claims.

Embodiments of the invention will now be described, by way of example, not limitation. It is to be understood that the invention is of broad utility and may be used in many different contexts.

A molecular subset is a whole or parts of the components of a molecule, where the components can be single atoms or bonds, groups of atoms and/or bonds, amino acid residues, nucleotides, etc. A molecular subset might include a molecule, a part of a molecule, a chemical compound composed of one or more molecules (or other bioactive agents), a protein, one or more subsets or domains of a protein, a nucleic acid, one or more peptides, or one or more oligonucleotides. In another embodiment, a molecular subset may also include one or more ions, individual atoms, or whole or parts of other simple molecules such as salts, gas molecules, water molecules, radicals, or even organic compounds like alcohols, esters, ketones, simple sugars, etc. In yet another embodiment, the molecular subset may also include organic molecules, residues, nucleotides, carbohydrates, inorganic molecules, and other chemically active items including synthetic, medicinal, drug-like, or natural compounds.

In yet another embodiment, the molecular subset may already be bound or attached to the target through one or more covalent bonds. In another embodiment, the molecular subset may in fact include one or more structural components of the target, such as secondary structure elements that make up a tertiary structure of a protein or subunits of a protein quaternary structure. In another embodiment, the molecular subset may include one or more portions of a target molecule, such as protein domains that include the whole or part of an active site, one or more spatially connected subsets of the protein structure that are selected based on proximity to one or more protein residues, or even disconnected protein subsets that feature catalytic or other surface residues that are of interest for various molecular interactions. In another embodiment, the molecular subset may include the whole of or part of an existing molecular complex, meaning a molecular combination between two or more other molecular subset, as, for example, an activated protein or an allosterically bound protein.

A molecular combination (sometimes referred to simply as combination) is a collection of two or more molecular subsets that may potentially bind, form a molecular complex, or otherwise interact with one another, usually in the context of a particular physical, chemical, or biological environment. A combination specifies at the very least the identities of the two or more interacting molecular subsets.

In many of the forthcoming examples and explanations, the molecular combination will represent the typical scenario of two molecular subsets where a ligand biomolecule (first molecular subset) interacts with a target biomolecule (usually a biopolymer; second molecular subset). Thus a typical analysis of a molecular combination seeks to determine whether, and to what degree, a ligand will interact with a target molecule in a particular environment. It should be understood that, unless otherwise indicated, such examples and explanations could more generally apply to molecular combinations wherein more than two molecular subsets bind or interact with one another, representing the whole of, or portion(s) of, one or more target molecules and/or one or more ligands, or even other molecules such as those that may be associated with the specified environment.

As an example, in one embodiment of the present invention the molecular combination may represent a target interacting with a ligand (i.e., target-ligand pair) where one molecular subset is from the protein and the other the ligand. In a further embodiment, the molecular combination may represent a target-ligand pair where one molecular subset is the entire ligand biomolecule but the other molecular subset is a portion of a target biopolymer containing one or more relevant active sites.

In yet another embodiment, the molecular combination may feature more than two molecular subsets, one representing a target (whole or part) and the other two correspond to two distinct ligands interacting with the same target at the same time, such as in the case of competitive thermodynamic equilibrium between a possible inhibitor and a natural binder of a protein. In yet another embodiment the previous example may be turned around such that the molecular combination features two target molecules in competition with one ligand biomolecule.

As another example, in one embodiment the molecular combination may represent a protein-protein interaction in which there are two molecular subsets, each representing the whole or a relevant portion of one protein. In a further embodiment, the molecular combinations may also represent a protein-protein interaction, but now with potentially more than two molecular subsets, each representing an appropriate protein domain.

As a further example, the molecular combination may feature two molecular subsets representing a target-ligand pair but also additional molecular subsets representing other atoms or molecules (heteroatoms or heteromolecules) relevant to the interaction, such as, but not limited to, one or more catalytic or structural metal ions, one or more ordered, bound, or structural water molecules, one or more salt molecules, or even other molecules such as various lipids, carbohydrates, acids, bases, mRNA, ATP/ADP, etc. In yet another embodiment, the molecular combination may feature two molecular subsets representing a target-ligand pair but also one or more added molecular subsets representing a whole or portion of a cell membrane, such as a section of a lipid bilayer, nuclear membrane, etc., or a whole or portion of an organelle such as a mitochondrion, a ribosome, endoplasmic reticulum, etc.

In another embodiment, the molecular combination may feature two or more molecular subsets, with one or more molecular subsets representing various portions of a molecular complex and another subset representing the ligand interacting with the complex at an unoccupied active site, such as for proteins complexed with an allosteric activator or for proteins containing multiple, distinct active sites.

In another embodiment, the molecular combination may feature two or more molecular subsets representing protein chains or subunits interacting noncovalently as per a quaternary protein structure. In another embodiment, the molecular combination may feature two or more molecular subsets representing protein secondary structure elements interacting as per a tertiary structure of a polypeptide chain, induced for example by protein folding or mutagenesis.

Molecular subsets are likely to interact differently in different environments as governed by any number of possible physical and/or chemical factors. Such factors may include, but are not limited to, temperature, pH, pressure, chemical potential, membrane permeability, solubility, polarizability (for both solute and solvent), viscosity, conductivity, dielectric strength, phase (gas, liquid, or solid) transitions or mixtures, electrostatic potentials between charges and/or various higher multipole moments, interfacial surface tension, presence of ions or salts in ambient solvent, etc. Different environments may also be characterized by location of the (probable) site of interaction between the molecular subsets such as, for example, the gastrointestinal tract, the bloodstream, in vitro in a laboratory test tube, the liver, a cellular membrane, in the cytoplasm, in a tumor, etc.

In one embodiment of the present invention, a molecular combination may include the definition of the environment. As such two different molecular combinations may then comprise the same set of interacting molecular subsets (e.g., target-ligand pair) but in the context of a different environment. As an example, one molecular combination may feature a target protein-ligand in a gas phase approximation in vacuum. For another molecular combination the same target protein-ligand pair may be in a liquid phase embedded in an ambient solvent medium. For yet another molecular combination the same target protein-ligand pair may be suspended in a crystalline lattice as per X-ray crystallography experiments.

In many of the forthcoming examples and explanations, the molecular combination will represent the typical scenario of a target-ligand pair interacting with one another in an aqueous solvent environment at physiological pH. Here the term solvent generally refers to the plurality of atoms, ions, and/or simple molecules (e.g., water, salt, sugars). In one embodiment the solvent may be represented by one or more solvent molecular subsets. In another embodiment, an appropriate continuum implicit solvation model may represent the solvent.

In yet another embodiment, a molecular combination may feature only one molecular subset interacting with itself and with surrounding solvent as per the determination of one or more best energy molecular conformers or, in the case of proteins, one or more favorable folds. In such a scenario, two different molecular combinations may feature the same, single molecular subset but in a different environment. In such embodiments, the environment can be viewed as a surrogate for the second molecular subset associated with standard molecular combinations. This is useful for determining an optimal pose for a molecule and other interactions of part of a molecule with itself.

As already mentioned, a typical analysis of a molecular combination may seek to determine whether, and to what degree, a ligand will interact with a target molecule in a particular environment. In another embodiment, the analysis may involve a plurality of molecular combinations, each corresponding to a different ligand, selected, for example, from a molecule library (virtual or otherwise), in combination with the same target molecule in the same environment, in order to find one or more ligands that might bind or otherwise react with the target or even to better characterize the active site of a target protein. In such cases, it may be necessary to assign a score or ranking for each molecular combination in order to achieve relative comparison of relevant bioactivity.

In such a scenario where each target-ligand pair is an individual combination, and if there are N ligands to be tested against one target, then there will be N distinct molecular combinations involved in the analysis. For sufficiently large molecule libraries, it may be necessary to analyze millions or more potential molecular combinations for a single target protein.

In yet another embodiment, the analysis may be reversed and the plurality of molecular combinations represents a plurality of target molecules, each in combination with the same ligand biomolecule in the same environment. In other embodiments, the molecular combinations may represent multiple ligands and/or targets reacting simultaneously, i.e., more than just a target-ligand pair, and may also include various heteroatoms or molecules as previously discussed.

The structure of a given molecular subset may be able to assume different geometric states meaning that the relative positions of atoms, bonds, and/or chemical groups in the molecular subset can change. This sort of variation of structure of a molecular subset will be referred to in the description henceforth as a conformation. In many of the forthcoming examples and explanations, it will be assumed that most covalent bonds are preserved during a change in conformation, i.e., bonds are not broken or formed, though this need not be the case for other chemical bonds such as disulfide bonds, hydrogen bonds, and salt bridges. However, it should obvious to one skilled in the art that the invention applies equally well to chemical reactions where bonds are readily broken or formed, since it is a straightforward to allow for both the coagulation or fragmentation of molecular subsets during analysis of a particular molecular combination.

Two different conformations of the same molecular subset may result due to relative changes in bond lengths, bond angles, bond torsions (both proper and improper), or other more complex changes such as ring transformations (e.g., ring corner flapping, ring book folding, etc.). The difference between two conformations may be as subtle (local) as the change in position of only one atom in the subset or as large (global) as the change associated with a distinct protein fold or the alteration of side chains for multiple active residues. Some changes in conformation while geometrically possible are not generally physically realizable as they may result in unfavorable steric clashes of constituent atoms or groups. The allowed changes in conformation are generally termed degrees of freedom.

FIGS. 1a-1f show diagrammatic examples of some of the standard degrees of freedom associated with changes in conformation of molecules. Item 102 shows an example of a chemical bond stretching, i.e., a change in bond length, between two neighboring atoms 104 and 106. Item 110 shows an example of bond angle bending, i.e., a change in bond angle, between three consecutive atoms 112, 113, and 115. Item 120 shows an example of a proper torsion, i.e., a rotation around the bond between atoms 122 and 123, or equivalently a change in the dihedral angle between the plane defined by atoms 121, 122, and 123 and the plane defined by 122, 123 and 124. Note that in this example for a proper torsion it is assumed that atoms 125 and 126 will similarly rotate around the bond between atoms 123 and 124, in order to preserve relative distances with respect to themselves and to atoms 123 and 124.

Figure 1D:
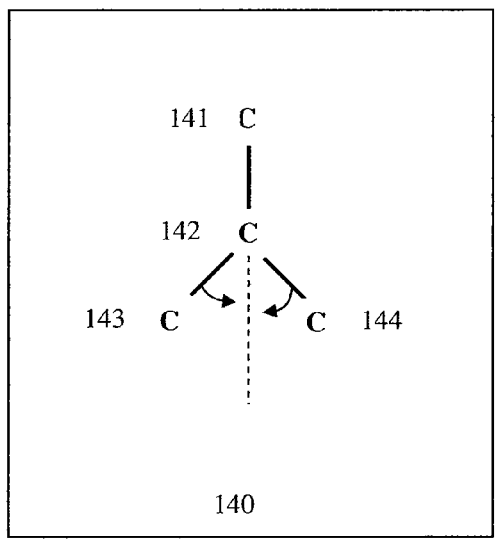
Figure 1E:
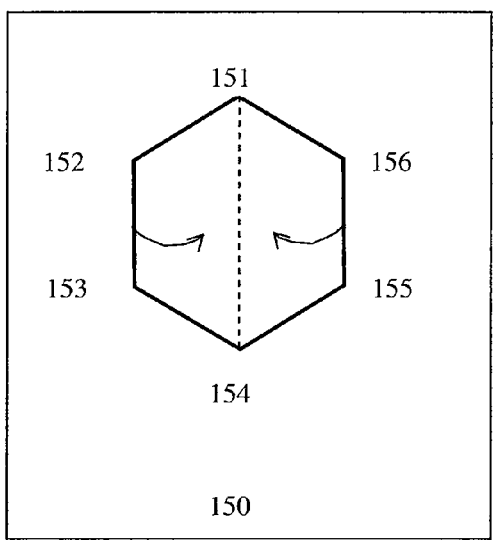
Figure 1F:
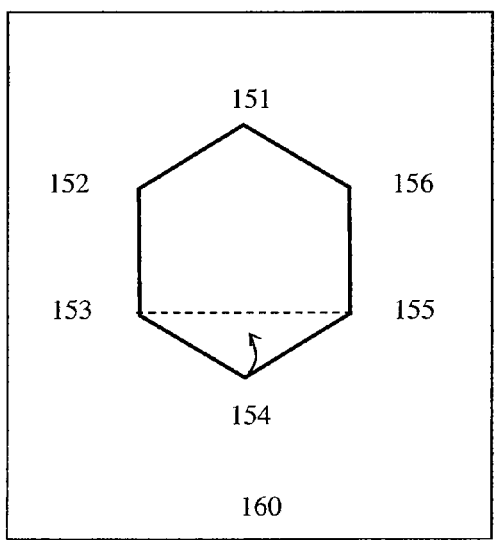

Continuing with FIG. 1d, item 140 shows an example of an improper torsion, i.e., a change in the dihedral angle between the plane defined by atoms 141, 142, and 143 and the plane defined by 141, 142 and 144. Item 150 shows an example of a 'book-folding' transformation of a nonaromatic homocyclic ring defined by atoms 151, 152, 153, 154, 155, and 156. In this case the transformation reflects a change in the angle between the plane defined by atoms 151, 152, 153, and 154 and the plane defined by 151, 156, 155, and 154. Lastly item 160 shows a 'corner-flapping' transformation of the same nonaromatic homocyclic ring, but now the transformation reflects a change in the angle between the plane defined by atoms 151, 152, 153, 156, and 155 and the plane defined by atoms 155, 154, and 153.

Other conformational degrees of freedom are possible such as (but not limited to) the exchange between cis and trans modes, the change in one or more chiral centers, reflecting different stereoisomers, or other more complicated deformations of rings, especially macrocylic ones. However, many (if not almost all) changes in molecular conformation that do not break or form covalent bonds can be decomposed into a collection of one or more of the aforementioned degrees of freedom listed in FIGS. 1a-1f.

In many cases a degree of freedom may also have constraints that reflect bounds on the permitted motions of relevant atoms and bonds. Such constraints may be motivated by the nature or hybridization state of the chemical bond(s), the energy landscape associated with the structural alteration in question, or even other more sophisticated considerations such as those relating to conservation of secondary structure elements or protein structural motifs or the presence of various heteroatoms or other molecules.

In many of the forthcoming examples and explanations, the conformation of a molecular subset will be dominantly associated with one or more degrees of freedom related to proper and improper torsions, since for many systems the bond lengths and bond angles of most chemical bonds in standard ligands and targets do not change significantly between the unbound and bound states of a combination; the most likely exception being associated with structural perturbations of chemical groups featuring cyclic (especially macrocyclic) rings. However, in many embodiments molecular conformations need not be limited to torsional degrees of freedom alone.

FIG. 2b shows a 'ball-and-stick' rendering of a conformation 205 of a methotrexate molecule 200 with chemical formula a $C_{20}H_{22}N_8O_5$ and a 2-D chemical representation depicted in FIG. 2a. The depicted molecular subset consists of a collection of atoms 220 and bonds 230. The small, black atoms, as indicated by item 213, represent carbon atoms. The tiny, white atoms, as indicated by item 216, represent hydrogen atoms, whereas the slightly larger dark atoms (item 210) are oxygen atoms and the larger white atoms (item 229) are nitrogen atoms. Continuing in FIG. 2a, item 223 denotes a circle containing a benzene ring ($C_6H_4$), and item 225 a circle containing a carboxyl group ($COO^-$), and item 227 another circle containing a methyl group ($CH_3$). Item 233 denotes a covalent bond connecting the benzene ring 223 to the ester group that includes the methyl group 227. Item 235 denotes a covalent bond connecting the carbon atom 213 to the carboxyl group 225. Lastly item 237 denotes a covalent bond connecting the methyl group 227 to a nitrogen atom 229.

FIG. 2c shows a 'ball-and-stick' rendering of another conformation 260 of the same methotrexate molecule 200. The conformations in FIGS. 2b and 2c differ only in the value of the torsion angles assigned to the torsional degrees of freedom for bonds 235 and 237, thus resulting in different positions for atoms and bonds in the methyl group (227) and the carboxyl group (225) relative to the rest of the molecule.

The conformation of a given molecular subset may be translated or rotated with respect to a global coordinate system leading to different geometric states. This sort of variation of the conformation of a molecular subset will be referred to in the description henceforth as a pose.

FIG. 3a shows a conformation 300 of a methotrexate molecule. Item 320 (in black) shows a three-dimensional coordinate axes defining a global Cartesian coordinate system, i.e., (x, y, z). Item 340 (in white) shows a local Cartesian frame (x', y', z') attached to the molecule, which is currently aligned with the global Cartesian axes 320. FIG. 3b shows the same conformation 300 but in a different pose. Now the molecule has been translated along the x-axis of the global Cartesian axes 320 and its attached Cartesian frame 340 has been rotated by the angles (a, b, c) with respect to the axes 320. Notice how the translation and rotation of conformation 300 is applied to all atoms uniformly so that the relative positions of one atom or bond with respect to another do not change.

When defining a conformation, the definition of a coordinate system used to represent the positions of atoms and bonds is immaterial, since the conformation relates to relative positions of constituent atoms and bonds in a molecular subset and as such any suitable coordinate system might be chosen. However, when considering a pose, the nature of the coordinate system will dictate how the atom and bond positions will be represented to all other parts of the molecular combination, including other molecular subsets and even to components of the environment. Moreover, the choice of coordinate system will determine how the translation and rotation operators will be defined and how they will act on a given conformation. Examples of typical coordinate systems include Cartesian, cylindrical, and spherical polar coordinates. A typical choice is to affix a local Cartesian frame (or equivalent) to the centroid or center of mass of the molecule.

Two different poses for a molecular subset may have identical conformations but differ only in their relative translation and rotation. Such poses are said to differ only by rigid-body transformations. On the other hand, the two poses may differ only in their conformations but no differences exist in terms of translation and orientation (i.e., local Cartesian frame affixed at centroid is same for both poses). Of course, the two poses may differ due to changes in both conformation and in translation and orientation with respect to the global coordinate system. FIG. 3c shows such a case where the methotrexate molecule is now in a different pose due to changes in both conformation and in translation and orientation. Traditionally there are a total of six degrees of freedom involved with the translation and orientation of a conformation, three for translation (e.g., displacement of centroid or center of mass) and three for orientation (e.g., Euler angles).

As a molecular combination may include two or more molecular subsets in a specified environment, the term configuration will be used henceforth in the description to represent the joint poses of all constituent molecular subsets. Thus a particular configuration of a molecular combination describes the set of positions of all structural components of all molecular subsets and all components of the environment with respect to one another, usually in the context of a chosen coordinate system.

FIG. 4a shows a configuration of a molecular combination featuring a ball and stick representation of the chemotherapy drug methotrexate 400 (ligand) and a portion of the protein dihydrofolate reductase 420 (target) represented via a solvent accessible surface (colored in dark gray). FIG. 4b shows a different configuration for the same molecular combination, featuring a different pose 440 for the same methotrexate ligand 400 and the same pose for the target protein 420. FIG. 4c shows yet a different configuration for the same molecular combination but now with different poses (460 & 480) respectively for both the ligand 400 and the target protein 420. Notice in FIG. 4c how the "groove" in the active site has changed as the result of conformational changes associated with the rearrangement of several active site residues.

When analyzing a molecular combination it may be necessary to assess many different configurations representing many different poses for each of the interacting molecular subsets. As an example let us consider the molecular combination described in FIGS. 4a-4c. For this example, let us assume for the moment that the protein will remain fixed and the ligand will assume multiple poses. Let us further assume that the methotrexate ligand will only change its conformation via a number of proper torsions and that bond lengths, bond angles, and ring geometries remained fixed during the analysis.

FIG. 5 shows a 2-D ball-and-stick representation (item 500) of the methotrexate ligand and also annotation for the permitted degrees of freedom representing proper torsions. Items 505, 510, 515, 520, 525, 530, 535, 540, 545, 550 represent the permitted torsional degrees of freedom (here the two bonds 570 and 575 connecting the trigonal planar nitrogen groups to the heterocyclic ring 585 and the amide bond 590 are assumed to be immobile due to favorable energetics involved with maintaining planarity). This makes for 10 torsional degrees of freedom in addition to the six degrees of freedom describing relative translation and orientation of the ligand with respect to the target protein.

In the current example, if the torsions are represented as discrete steps of 10° over the full range −180° to +180°, the volume of the protein active site is approx. $10^3$ Å, the translation of the ligand is sampled in steps of 0.5 Å, and three Euler angles describing orientation are sampled in steps of also 10°, then there are possibly more than $6\times10^{23}$ possible configurations for the combination. Of course many of the poses have little or no probability of being physically realizable as they may be very energetically unfavorable due to steric clashes of the ligand with itself or with the protein, while others may not be close enough to the protein in order to form favorable interactions. However, the current example should still illustrate the potential enormity of configurations involved.

Typically when analyzing such a combination, a process will take certain shortcuts and will not attempt to evaluate all possible configurations but may try instead to efficiently and intelligently examine a reasonable subset, with the premise that the desired configurations associated with one or more potential binding modes are approximately represented in this analyzed subset. Of course adding further configurational complexity to the combination, such as finer sampling of the degrees of freedom or the consideration of protein conformational changes, such as for example those corresponding to one or more torsion degrees of freedom associated with side chains of active site residues, will only further increase the number of possible configurations.

Typically, a set of appropriate molecular descriptors describing each distinct configuration will be used to distinguish one configuration from another. Molecular descriptors may include, but are not limited to, a) chemical descriptors (e.g., element, atom type, chemical group, residue, bond type, hybridization state, ionization state, tautomeric state, chirality, stereochemistry, protonation, hydrogen bond donor or acceptor capacity, aromaticity, etc.); b) physical descriptors (e.g., charge, both formal and partial, mass, polarizability, ionization energy, characteristic size parameters, such as van der Waals [vdW] radii, vdW well depths, hydrophobicity, hydrogen bonding potential parameters, solubility, equilibrium bond parameters relating bond energies to bond geometries, etc.); c) geometrical descriptors (e.g., atomic coordinates, bond vectors, bond lengths, bond angles, bond torsions, suitable structural descriptors for rings, descriptors for molecular surfaces and volumes, such as solvent accessible surfaces and solvent-excluded volumes, etc.); and d) environmental descriptors (e.g., temperature, pH, ionic strength, pressure, etc.).

Chemical descriptors may be assigned based on application of one or more rules or concepts of organic (or inorganic, if appropriate) chemistry to represent chemical structures that must at least stipulate basic structural information such as element type and bond connectivity (i.e., minimally which nonhydrogen atoms are connected to one another) but may also contain some form of coordinate information. Such chemical structures may be stored and received in a number of different data representations. One common example of data representation, though many others are also possible, is that of a PDB file, for which a full description of the PDB file format can be found Westbrook et al. [53]. Examples of currently available software programs that can be used to assign chemical descriptors include SYBYL™ computational informatics software for molecular modelers from Tripos, CHIMERA™ program for interactive visualization and analysis of molecular structures and related data from UCSF, and WHATIF™ program for molecular modeling and drug design that is specialized on working with proteins and the molecules in their environment originally from EMBL, etc. These are modeling softwares that are used for processing, analyzing, and/or visualizing proteins and protein structures. Correct assignment of chemical descriptors may also include additional input regarding chiral centers and stereochemistry or even environmental factors, such as expected pH as related to assignment of ionization states.

FIG. 6a shows a pdb file representation 600 of a chemical structure for the methotrexate ligand conformation described in FIG. 5, including a general header 610, a section 620 composed of atom type and coordinate information, and a section 625 regarding bond connectivity information. The header section 610 may contain any annotation or other information desired regarding the identity, source, or characteristics of the molecule and its conformation. Section 620 shows a list of all 33 nonhydrogen atoms of methotrexate and for each atom it includes a chemical type (e.g., atomic element) and three spatial coordinates. For instance, the line for atom 6 shows that it is a nitrogen atom with name NA4 in a compound (or residue if a protein) named MTX in chain A with compound (or residue) ID of 1 and with (x, y, z) coordinates (20.821, 57.440, 21.075) in a specified Cartesian coordinate system. Note that the compound or residue name field may be more relevant for amino or nucleic acid residues in biopolymers.

Section 625 of the PDB file 600, sometimes called the connect record of a PDB file, describes a list of the bonds associated with each atom. For instance, the first line of this section shows that atom 1 is bonded to atoms (2), and (12), whereas the second line shows that atom 2 is bonded to atoms (1), (3), and (4). Notice also how in this example hydrogens are missing and as such the bond connections for each atom may not be complete. Of course, completed variants of the PDB file representation are possible if the positions of hydrogen atoms are already specified, but in many cases where the chemical structure originates from experimental observations the positions of hydrogens may be very uncertain or missing altogether.

FIG. 6b shows a Tripos mol2 file containing various structural and chemical information for the input conformation for methotrexate depicted in FIG. 6a. Column 630 lists an index for each atom; column 633 lists an atom name (may be nonunique) for each atom; columns 635, 637, and 639 respectively list x, y, z coordinates for each atom in an internal coordinate system; column 640 lists a SYBYL atom type according to the Tripos force field [56] for each atom that codifies information for hybridization states, chemical type, bond connectivity, hydrogen bond capacity, aromaticity, and in some cases chemical group; and columns 642 and 645 list a residue ID and a residue name for each atom (relevant for proteins, nucleic acids, etc.). Section 650 lists all bonds in the molecular subset. Column 691 lists a bond index for each bond; columns 652 and 653 the atom indices of the two atoms connected by the bond; and column 655 the bond type, which may be single, double, triple, delocalized, amide, aromatic, or other specialized covalent bonds. In other embodiments, such information may also represent noncovalent bonds such as salt bridges or hydrogen bonds. In this example, notice how the hydrogen atoms have now been included.

In this example, notice how the hydrogen atoms have now been included (and in this case their likely positions predicted) as the result of assignment of chemical descriptors. In this example, the depicted atom types contain codified information for hybridization states, chemical type, bond connectivity, hydrogen bond capacity, aromaticity, and in some cases chemical group. Moreover, the ionization states can generally be inferred by a combination of atom types and hydrogenation. Other examples may even include data relevant to lone pairs.

Physical descriptors depend on one or more chemical descriptors and are typically related to atoms and/or bonds but may also be characterized by chemical group, residue, etc. Values for physical descriptors are typically assigned according to one or more parameter sets associated with molecular mechanics force fields like AMBER [40][41], OPLS [42], MMFF [43], and CHARMM [44]. Some physical descriptors may also be assigned according to the use of one or more molecular modeling software packages such as the assignment of partial charges via Mopac [45] or AMPAC [46]. The choice of energy interactions to be modeled will typically dictate the type and form of physical descriptors that must be determined for each molecular subset in order to compute affinity for a given molecular combination.

FIG. 6c shows a file containing a subset of physical descriptors assigned via the Amber96 force field (in conjunction with Mopac v7.0 for the partial charges) for the methotrexate ligand corresponding to FIGS. 5, 6a, and 6b. Section 660 describes atomic physical descriptors related to charge (column 662), mass (column 663), vdW radius (column 664), and vdW well depth (column 665) for the identical atom names (column 661) originally listed in FIG. 6a. Section 670 describes bond physical descriptors related to the ten allowed bond torsions described in FIG. 5. Here columns 672, 674, 676, and 678 denote standard numerical parameters for a generalized Pitzer potential used in estimating the strain energy associated with dihedral changes.

Geometrical descriptors relate to the description of structure of one or more components of the molecular combination. This may include, but is not limited to, coordinates or other spatial information relating to points representing positions of atomic centers, vectors representing various bonds, planes representing various chemical groups, spheres representing the extent and placement of individual atoms, 3-D surfaces representing solute—solvent interfaces, volumes representing solute occupancy, spatial 3-D functions representing discretization of interaction fields or potentials onto 3-D volumetric grids (e.g., probe grid maps [26][31], meshes for differential equation solvers, etc.), or even a generalized set of appropriate geometrical basis functions for approximate representations of structures, surfaces, and/or volumes (e.g., spherical harmonics radial basis functions of Ritchie et al. [13]). Geometrical descriptors may also include one or more geometric variables (e.g., angles, torsions, lengths, etc.) representing one or more allowed degrees of freedom associated with different poses, such as some of the conformational degrees of freedom described in conjunction with FIG. 1 FIGS. 1a-1f.

Some geometric descriptors, like for example, those describing points, vectors, planes, and spheres, have natural representations, though the actual values may depend on the choice of coordinate system. Others like surfaces, volumes, grid maps, or basis functions may have various representations depending on the storage requirements, the level of desired precision, and the nature of the object to be represented. As an example, surface may be represented by a series of surface normals or a collection of various elementary surface patches. Volumes may be represented by occupancy of a 3-D bitmap or by a union of simpler geometric objects such as spheres or polygons.

Geometrical descriptors involved with structural degrees of freedom may be continuous or discrete variables, may have one or more constraints imposed by basic structural or energetic considerations, and may depend on the choice of an internal coordinate system for the molecular subset. Such descriptors are of particular importance as they describe the geometrical transformations (or operators) that distinguish two different geometric states of the same molecule or combination (e.g., conformation, pose, configuration).

In some embodiments various geometric descriptors are derived from input structural data. For example, FIGS. 6b (and also 6a) already shows spatial coordinates for an input structure for the methotrexate ligand. Bond vectors can be easily derived via use of both the spatial coordinates of section 620 and the connect record of section 625. Bond angles can be derived from bond vectors. Dihedral angles associated with proper or improper torsions can be derived from the two planes defined by sets of consecutive bond vectors and so forth.

Environmental descriptors may be expected to vary depending on the anticipated site of action for the molecular combination. Environmental descriptors may represent three-dimensional functions that vary between different positions in the system and may require suitable choice of one or more system boundary conditions. The choice of solvent mediums as either explicit (e.g., explicit water dipoles simulations [67][68][69]) or implicit (Generalized Born [62][63], Poisson Boltzmann equation [60][61]) representations may significantly alter the computational complexity associated with analysis of a given molecular combination.

The set of molecular descriptors attached to a particular configuration will be termed henceforth as a configuration record throughout the remainder of the text. Two configuration records involving the same molecular combination of molecular subsets in the same physical environment differ in at least one included geometric descriptors. Two configuration records involving two different molecular combinations (even in the same environment) are expected to exhibit differences in one or more chemical, and hence physical, descriptors as well as one or more geometrical descriptors. A molecule record will be used to refer to that portion of the configuration record that is related to the descriptors for one of the molecular subsets.

To serve as a starting point for analysis of a molecular combination, each molecular subset may be supplied with an input molecule record, often containing geometric descriptors for an initial pose of the molecular subset. In one embodiment initial poses may be generated from initial conformations derived from input 3-D (or in some cases, 2-D) chemical structures. Typically, such input structures may originate as the result of experiment or of prior molecular modeling and/or conformational analysis. Examples of prior molecular modeling and conformational analysis may include protein threading, energy-based conformation minimization (e.g., molecular dynamics simulation, stochastic optimization, etc.), or 2-D to 3-D structure conversion tools (e.g., CORINA [57]). In other embodiments the input structure may even be randomly generated by random value assignment of various geometrical descriptors. Initial poses for each molecular subset may be generated from initial conformations by random assignment of global translation and/or orientation variables. Typically, methods for the analysis of molecular combinations based on stochastic optimization will often involve some form of random assignment of one or more geometric descriptors before optimization begins. In other embodiments, the initial poses corresponding to one or more input molecule records may result from other previous molecular modeling of individual molecular subsets (or even the combination as a whole) as part of an iterative procedure.

When processing a molecule library it may be necessary to analyze potentially millions or even billions of different molecular combinations each requiring the assessment of potentially millions or even billions of system configurations. As part of the efficient assessment of each system configuration, it is often desirable to utilize methods for both efficient generation of different conformations, poses, and (hence)

configurations of a molecular combination, and storage of associated molecule and (hence) configuration records.

In some embodiments, efficient construction or structural modification of system configurations may be accomplished via application of a one or more geometrical operators characterized by a set of geometric descriptors. Typically, the order and number of visited configurations during analysis of the molecular combination is often dictated by the choice of search or optimization method used. In one embodiment, the collection of configurations visited (possibly ordered) during the analysis may be initiated from an initial configuration comprising one or more input molecular records related to input structures for each molecular subset. Selected geometrical operators may then be used to generate one or more configurations either in sequence (e.g., state trajectory in a Monte Carlo-based scheme) or in parallel (e.g., population in a genetic algorithm).

In one embodiment this may be accomplished through random variation of one or more degrees of freedom. In another embodiment this may be accomplished through the application of a union or sequence of transformations corresponding to one or more degrees of freedom such as those outlined in FIGS. 1a-1f. In yet another embodiment this may be based on other operators such as crossover in genetic algorithms or probabilistic variation based on state energy differences associated with simulated annealing or other Monte Carlo-based methods.

Such a use of geometrical operators may have a profound impact on the storage of geometrical descriptors as part of molecule records associated with different configurations. For example, instead of storing a unique set of spatial coordinates for each atom in a configuration it may be possible to store coordinates for only one template configuration (e.g., an initial or randomized configuration or other canonical variant) and then record the values for all relevant geometrical descriptors that represent the net transformation of the template configuration into the particular configuration of interest via application of a series of geometric operators.

As an example, in one embodiment, instead of representing the geometrical descriptors of the conformation depicted in FIG. 2c via a separate PDB record (or equivalent), it may be more efficient to use an original PDB record associated with the conformation depicted in FIG. 2b, in conjunction with two torsion angle values corresponding respectively to the change in dihedral angles of bonds 235 and 237, in order to represent the FIG. 2c conformation without requiring two distinct PDB records. Alternatively, in another embodiment it may still be practical to store all atomic coordinates explicitly. Explicit representation of surfaces and volumes (if necessary for analysis) may be very costly to store without the use of appropriate geometrical transformations.

In one embodiment, as physical descriptors are often fundamentally associated with atoms and bonds and thus typically do not change between different configurations for the same molecular combination in the same environment, it may be more expedient to store them in one or more lookup tables addressable by, for example, atom or bond index, as opposed to allocating separate storage for possibly redundant data. In another embodiment, the same logic can be used to reduce redundant storage of certain chemical descriptors between different configurations for the same molecular combination in the same environment. Depending on the modeling sophistication involved, the storage requirements for environmental descriptors may range from very small (e.g., set of constants describing implicit solvation model) to very large (e.g., high density grids representing spatial variation of 3-D functions in an explicit solvation scheme).

In one embodiment, molecule records may be stored as one or more file records in a flat file system on a recordable storage medium. In another embodiment, molecule records may be represented as records or entries in one or more databases, i.e., one or more table rows in a relational database or elements of one or more objects in an object-oriented database. In another embodiment configuration records may be represented by the simple direct union of a set of molecule records corresponding to each molecular subset. In yet another embodiment configuration records may be supplemented by additional information related to the results of a particular assessment of a system configuration, such as a configuration score or other qualitative or quantitative measure. In other embodiments, provisions are made in the data representation of molecule and configuration records to remove redundant information to allow for more efficient storage and/or data access. In another embodiment, the descriptor data (especially geometric and chemical) may be stored in one or more specialized memory allocation structures in accordance with the molecular representation partitioning described in Ahuja I in order to facilitate efficient computation. In yet other embodiments, the descriptor data may be stored in various other standard data structures, including, but not limited to, lists, trees, heaps, hash tables, directed graphs, or hybrids thereof, or even more specialized memory allocation structures such as the molecular graph structures discussed in.

As mentioned earlier, the estimation of binding affinity or binding energy is typically of interest when analyzing molecular combinations. This is often accomplished by the computation of an affinity function that depends on both the nature of the interacting molecular subsets in a corresponding molecular configuration. An affinity function may represent interactions between molecular subsets, interactions of each molecular subset with itself, or interactions of molecular subsets with their environment. Calculation of an affinity function for a given configuration of a molecular combination will usually involve a set of molecular descriptors describing various chemical, physical, and geometric/structural properties of the combination, and may comprise a plurality of molecule records or a single configuration record. In some embodiments the affinity function may be a mathematical function or score representing one or more energies such as binding affinity, binding energy, or free energy of a molecular system. In other embodiments, the affinity function may represent other qualitative measures, including, but not limited to, a measure of shape complementarity, a score, a QSAR prediction, a binding constant, or a reaction rate or probability. In yet other embodiments, the affinity function may represent various qualitative measures such as a grade, a categorization, or other classification (e.g., reacts at all, highly reactive, not very reactive).

The affinity function often comprises one or more affinity components that are composed or accumulated in some fashion in order to generate an affinity value or score for the combination. In some embodiments the affinity component may be characterized by a combination of one or more interaction types, affinity formulations, and an associated computation strategy.

In one embodiment, the composition of affinity components to form an affinity function is a straight sum of each component. In another embodiment, the composition may be a linear combination of affinity components with each component first multiplied by a corresponding weight before accumulation. In yet another embodiment, the composition may be a generalized (potentially nonlinear) function of the affinity components. In another embodiment, the composition of the affinity components may be decision based, e.g., include one component if and only if value is greater than some threshold, etc. In another embodiment, the composition may be determined as the result of a regression based on a training set of molecular combinations with experimental measurements of binding affinity or equivalent. In yet another embodiment the composition may be dynamically determined via pattern recognition methods such as by use of a neural network or a support vector machine.

The term interaction type refers herein to a type of physical or chemical interaction of one or more molecular subsets with itself (intramolecular) or other molecular subsets (intermolecular) or with components of an environment (environmental). Interaction types may be either enthalpic or entropic in nature and may reflect either nonbonded or bonded interactions.

Examples of nonbonded interaction types include, but are not limited to, electrostatic interactions, vdW (or dispersion) interactions between time-varying dipole moments (often related to steric complementarity), short range repulsion between overlapping atomic orbitals, hydrogen bonding, interactions involved with metal ion coordination, or interactions with one or more ordered or structural waters. Other examples of nonbonded interaction types may also include one or more solvation effects such as electrostatic desolvation (including self-reaction field polarization effects, solvent screening in a dielectric medium or interactions with a solvent-based ionic atmosphere), the hydrophobic effect, cavitation energy, and surface tension.

Examples of bonded interactions include, but are not limited to, the intramolecular strain associated with distortions of equilibrium bond lengths, angles, torsions, etc., or the energy gap between cis-trans modes or the energy differential associated with changes in chirality of one or more chiral center. Examples of entropic-based interactions include the loss of conformational entropy of molecular subsets (including loss of rotameric entropy for protein side chains) upon binding or the favorable entropy gain obtained by the release of one or more ordered waters. Other more exotic interaction types may include pi-pi stacking, charge transfer, or other quantum mechanical phenomena.

The term affinity formulation refers herein to the energy model used to calculate approximate quantitative values for a given interaction type for a configuration associated with a molecular combination. Typically, there may be many different affinity formulations for a given interaction type from which to choose. The choice of affinity formulation may affect the amount of error associated with the quantitative approximation of a given interaction type. The choice of affinity formulation may also involve very different levels of modeling sophistication and hence computational complexity. A given affinity formulation may require one or more molecular descriptors for evaluation. Two different affinity formulations for a given interaction type may require a very different set of molecular descriptors, while others may share multiple molecular descriptors in common.

For example, electrostatic interactions may be modeled according to an affinity formulation involving the use of a modified form of Coulomb's law with distance-dependent dielectric function (such as that described in [59]) as applied to a set of partial charges assigned to atomic centers in each molecular subset via use of a suitable force field. In another example, both electrostatic and electrostatic desolvation interactions may be modeled according to an affinity formulation involving a solution of the Poisson-Boltzmann equation (linear or nonlinear) [60][61] along with an assumption of point charges embedded in solute spherical cavities with size defined by vdW radius of each atom and the solute spheres placed in a homogeneous dielectric medium representing water with and possibly containing an ionic atmosphere as described in Gilson et al. [58]. Alternatively, electrostatic interactions may be modeled based on quantum-mechanical solution of electronic ground states for each molecular subset [70]. In most scenarios the modified Coulomb with distance-dependent dielectric formulation will be cheaper to compute but less accurate than a Poisson-Boltzmann-based formulation let alone a full quantum-mechanical solution.

As further examples, vdW interactions may be modeled according to an affinity formulation based on use of a generalized Lennard-Jones potential or alternatively based on a steric complementarity score such as that outlined in Ritchie et al. [13]. Hydrogen-bonding interactions may be modeled according to an affinity formulation based on use of a 12-10 Lennard-Jones potential with a angular weighting function [31] or by rescaling of partial charges and vdW radii of hydrogen bond donor and acceptor atoms such as that found in the Amber force field [40][41]. The hydrophobic effect may be modeled according to an affinity formulation based on the fragmental volume approach of Stouten et al. [66] or the solvent accessible surface area-based formalism of Eisenberg et al. [64]. Intramolecular strain associated with dihedral changes may be modeled according to an affinity formulation based on use of Pitzer potentials or by inverse Gaussian torsional constraints. As yet another example, instead of using a Poisson Boltzmann-based formulation, electrostatic desolvation for a configuration may be modeled via an affinity formulation based on use of a variant of the Generalized Born approximation [62][63].

The term "computation strategy" herein refers to the computational technique used to quantitatively evaluate a given affinity formulation for one or more interaction types. The choice of computation strategy may be influenced by the available computational systems, apparatus, means and/or methods, the available memory capacity, and/or computing time constraints.

As an example of different computational strategies for the same affinity formulation, consider the electrostatic interaction for target-ligand combination, for which a modified Coulombic affinity formulation with distance-dependent dielectric may be computed according to a computation strategy involving direct summation of pair-wise calculation between all possible pairs of partial charges across the protein and ligand. For a ligand with 100 atoms and a protein with 3000 atoms, this would entail the calculation of 300 K intermolecular distances let alone the number of distinct intramolecular pairs.

An alternative computation strategy is to instead utilize a probe grid map approximation [26] whereby an electrostatic potential function associated with source charges on the protein is evaluated and stored on 3-D grid for coordinate locations enclosing the protein. Then for each ligand charge a corresponding electrostatic potential value is accessed from memory (or other storage) and the direct product of the charge and the potential is then accumulated over all charges in the ligand. This may significantly reduce computational effort especially in the context of screening a molecule library where many molecular combinations may feature the same target protein but different ligands. Of course, the probe grid map approximation may require significant storage in order to reduce numerical errors related to variation of the potential function. Moreover, such an approximation is only suitable when the source charges of the protein do not change positions between different configurations. An alternative for a target protein featuring a flexible binding pocket, may be to use a hybrid computation strategy involving the use of the pair-wise strategy for the portion of the protein containing mobile source charges and the probe grid map strategy for the remainder of the protein, such as outlined in Luty et al. [26].

In general, various different computation strategies may be applied to other affinity formulations for other interaction types. On the other hand, the choice of computation strategy may be limited by the nature of the affinity formulation or interaction type in question. For example, it is unlikely that one would a strategy appropriate for evaluation of intermolecular electrostatics interactions to instead compute intramolecular strain components involving bonded interactions.

Other types of computational strategies exist than those based on pair-wise (e.g., interactions between pairs of atoms) or map or potential field (e.g., interactions of an atom with a potential field) calculations. For example, the evaluation of a Generalized Born solvation model based on the calculation of either volume integrals over the solvent excluded volume (Still et al. [62]) or on the calculation of surface integrals on the solvent accessible surface area (Ghosh et al. [63]). As yet another example, various formulations of bonded interactions may be evaluated according to a computation strategy featuring traversal of an appropriate data structure containing relevant coordinate and bond descriptors.

To summarize, an affinity function is a composition of affinity components each of which corresponds to a combination of an interaction type, an affinity formulation, and a computation strategy. An affinity component may represent interactions for the whole or parts of one or more molecular subsets. An affinity function may contain multiple affinity components relating to the same interaction type. For example, two affinity components may represent the same interaction type but differ in either their affinity formulation and/or their computation strategy. Each distinct molecular configuration for a given molecular combination may produce different quantitative results for an affinity component and hence for the corresponding affinity function. In one embodiment, the analysis of a molecular combination may be based on determination of the configuration with the best value for the affinity function. In other embodiments, multiple favorable values for the affinity function corresponding to molecular configurations associated with one or more potential binding modes may be considered. In yet another embodiment, multiple affinity functions may be computed on one or more configurations of a molecular combination and some decision or action based on their joint consideration, such as for example the scenario of consensus scoring of a small finite number of configurations for each molecular combination explored in the course of screening a molecule library against a target molecule.

FIG. 7 illustrates a modeling system 700 for the analysis of molecular combinations. As shown a configuration modeler 702 receives one or more input configuration records 706, including both the identities of and molecular descriptors for input structures for one or more molecular subsets from an input molecular combination database 704. The configuration modeler 702 comprises a configuration data transformation engine 708, an affinity calculator 709, and descriptor data storage 720. Results from the configuration modeler 702 are output as configuration results records 711 to a results database 710.

Modeling system 700 may be used to determine or characterize one or more molecular combinations. In some embodiments, this may include, but is not limited to, prediction of likelihood of formation of a potential molecular complex, or a proxy thereof, the estimation of the binding affinity or binding energy between molecular subsets in an environment, the prediction of the binding mode (or even additional alternative modes) for the molecular combination, or the rank prioritization of a collection of molecular subsets (e.g., ligands) based on predicted bioactivity with a target molecular subset, and would therefore also include usage associated with computational target-ligand docking and scoring.

In a typical operation, many molecular combinations, each featuring many different molecular configurations, may be modeled. Since the total possible number of configurations may be enormous, the modeling system may sample a subset of configurations during the modeling procedure, though the sampling subset may still be very large (e.g., millions or billions of configurations per combination) and the selection strategy for configuration sampling is specified by one or more search and/or optimization techniques (e.g., steepest descent, conjugate gradient, modified Newton's methods, Monte Carlo, simulated annealing, genetic or memetic algorithms, brute force sampling, pattern matching, incremental construction, fragment place-and-join, etc.). An affinity function is evaluated for each visited configuration and the results for one or more configurations recorded in a storage medium.

The molecular combination may then be assessed by examination of the set of configuration results including the corresponding computed affinity function values. Once the cycle of computation is complete for one molecular combination, modeling of the next molecular combination may ensue. Alternatively, in some embodiments of the modeling system 700, multiple molecular combinations may be modeled in parallel as opposed to in sequence. Likewise, in some embodiments, during modeling of a molecular combination, more than one configuration may be processed in parallel as opposed to in sequence.

In one embodiment, modeling system 700 may be implemented on a dedicated microprocessor, ASIC, or FPGA. In another embodiment, modeling system 700 may be implemented on an electronic or system board featuring multiple microprocessors, ASICs, or FPGAs. In yet another embodiment, modeling system 700 may be implemented on or across multiple boards housed in one or more electronic devices. In yet another embodiment, modeling system 700 may be implemented across multiple devices containing one or more microprocessors, ASICs, or FPGAs on one or more electronic boards and the devices connected across a network.

In some embodiments, modeling system 700 may also include one or more storage media devices for the storage of various, required data elements used in or produced by the analysis. Alternatively, in some other embodiments, some or all of the storage media devices may be externally located but networked or otherwise connected to the modeling system 700. Examples of external storage media devices may include one or more database servers or file systems. In some embodiments involving implementations featuring one or more boards, the modeling system 700 may also include one or more software processing components in order to assist the computational process. Alternatively, in some other embodiments, some or all of the software processing components may be externally located but networked or otherwise connected to the modeling system 700.

In some embodiments, results records from database 710 may be further subjected to a configuration selector 712 during which one or more molecular configurations may be selected based on various selection criteria and then resubmitted to the configuration modeler 702 (possibly under different operational conditions) for further scrutiny (i.e., a feedback cycle). In such embodiments, the molecular configurations are transmitted as inputs to the configuration modeler 702 in the form of selected configuration records 714.

In another embodiment, the configuration selector 712 may also send instructions to the configuration data transformation engine on how to construct one or more new configurations to be subsequently modeled by configuration modeler 702. For example, if the configuration modeler modeled ten target-ligand configurations for a given target-ligand pair and two of the configurations had substantially higher estimated affinity than the other eight, then the configuration selector 712 may generate instructions for the configuration data transformation engine on how to construct further additional configurations (i.e., both target and ligand poses) that are structurally similar to the top two high-scoring configurations, which are then subsequently processed by the remainder of the configuration modeler 702. In some embodiments, the transmitted instructions may relate to construction from the resubmitted configurations whereas in other cases they relate to construction from the original input reference configuration(s).

In some embodiments, once analysis of a molecular combination is completed (i.e., all desired configurations assessed) a combination postprocessor 716 may be used to select one or more configuration results records from database 710 in order to generate one or more qualitative or quantitative measures for the combination, such as a combination score, a combination summary, a combination grade, etc., and the resultant combination measures are then stored in a combination results database 718. In one embodiment, the combination measure may reflect the configuration record stored in database 710 with the best observed affinity. In another embodiment, multiple high affinity configurations are submitted to the combination postprocessor 716 and a set of combination measures written to the combination results database 718. In another embodiment, the selection of multiple configurations for use by the combination postprocessor 716 may involved one or more thresholds or other decision-based criteria.

In a further embodiment, the selected configurations are also chosen based on criteria involving structural diversity or, alternatively, structural similarity (e.g., consideration of mutual rmsd of configurations, use of structure-based clustering or niching strategies, etc.). In yet another embodiment, the combination measures output to the combination results database 718 are based on various statistical analysis of a sampling of possibly a large number of configuration results records stored in database 710. In other embodiment the selection sampling itself may be based on statistical methods (e.g., principal component analysis, multidimensional clustering, multivariate regression, etc.) or on pattern-matching methods (e.g., neural networks, support vector machines, etc.)

In yet another embodiment, the combination results records stored in database 718 may not only include the relevant combination measures, but may also include some or all of the various configuration records selected by the combination postprocessor 716 in order to construct a given combination measure. For example, combination results records stored in database 718 may include representations of the predicted binding mode or of other alternative, high affinity (possibly structurally diverse) modes for the molecular combination.

In another embodiment, the combination postprocessor 716 may be applied dynamically (i.e., on-the-fly) to the configuration results database 710 in conjunction with the analysis of the molecular combination as configuration results records become available. In yet another embodiment, the combination postprocessor 716 may be used to rank different configurations in order to store a sorted list of either all or a subset of the configurations stored in database 710 that are associated with the combination in question. In yet other embodiments, once the final combination results records, reflecting the complete analysis of the molecular combination by the configuration modeler 702, have been stored in database 718, some or all of the configuration records in database 710 may be removed or deleted in order to conserve storage in the context of a library screen involving possibly many different molecular combinations. Alternatively, some form of garbage collection or equivalent may be used in other embodiments to dynamically remove poor affinity configuration records from database 710.

In one embodiment, the molecular combination record database 704 may comprise one or more molecule records databases (e.g., flat file, relational, object oriented, etc.) or file systems and the configuration modeler 702 receives an input molecule record corresponding to an input structure for each molecular subset of the combination, and possibly a set of environmental descriptors for an associated environment. In another embodiment, when modeling target protein-ligand molecular combinations, the molecular combination record database 704 is replaced by an input target record database and an input ligand (or drug candidate) record database. In a further embodiment, the input target molecular records may be based on either experimentally derived (e.g., X-ray crystallography, NMR, etc.), energy minimized, or model-built 3-D protein structures. In another embodiment, the input ligand molecular records may reflect energy minimized or randomized 3-D structures or other 3-D structures converted from a 2-D chemical representation, or even a sampling of low energy conformers of the ligand in isolation. In yet another embodiment, the input ligand molecular records may correspond to naturally existing compounds or even to virtually generated compounds, which may or may not be synthesizable.

In one embodiment the configuration data transformation engine 708 may transform one or more input molecular configurations into one or more other new configurations by application of various geometrical operators characterized by sets of geometrical descriptors. Transformation of molecular configurations into newer variants may be accomplished by one or more unary operations (i.e., acting on one input configuration, such as the mutation operator in a genetic algorithm), binary operations (i.e., acting on two input configurations, such as a binary crossover in a genetic algorithm), other n-ary operations (i.e., acting on a plurality of input configurations, such as a transform operator based on a population of configurations), or a combination thereof. In another embodiment, the transformation of molecular configurations into newer variants may result in multiple new configurations from one configuration, such as, for example, the construction of a suitable (often randomized) initial population for use in a genetic algorithm. In some embodiments, the configuration data transformation engine 708 may be able to construct ab initio one or more entirely new configurations without the requirement of input geometrical descriptors from an input molecular combination database 704, though other types of molecular descriptors may still be needed.

As already discussed, in some embodiments, the set of configurations generated via transformation during the course of an analysis of a molecular combination may be determined according to a schedule or sampling scheme specified by one or more search and/or optimization techniques used to drive the modeling processes of the configuration modeler 702. In some embodiments, the search strategy or optimization technique may be an iterative process whereby one or more configurations are generated from one or more input configurations, then affinities are calculated for each configuration, decisions are made based on affinity and/or structure, and all or part of the new set of configurations are used as input seeds for the next iteration; the process continuing until a specified number of iterations are completed configuration modeler 702 or some other convergence criteria satisfied. In such embodiments, the input configuration records 706 obtained or derived from data in the input molecular combination database 704, may serve only to initiate (or also possibly reset) the iterative process (i.e., prime the pump).

In some embodiments, the search strategy or optimization technique may be stochastic in nature meaning that the set of configurations visited during analysis of a molecular combination may involve some random component and thus be possibly different between different runs of the configuration modeler 702 as applied to the same molecular combination. Here the term run refers to two different initiations of (possibly iterative) cycles of computation for analysis of the same molecular combination. In some embodiments, the combination postprocessor 716 may then base its results or decisions on configuration results records stored in database 710 but obtained from different runs.

In some embodiments, the configuration data transformation engine 708 may produce new configurations sequentially, such as a new possible state associated with a given iteration of a Monte Carlo-based technique, and feed them to the affinity calculator 709 in a sequential manner. In other embodiments, the configuration data transformation engine 708 may produce multiple new configurations in parallel, such as a population associated with a given iteration of a genetic algorithm, and submit them in parallel to the affinity calculator 709.

In other embodiments, the configuration data transformation engine 708 may not generate additional configurations and instead the configuration modeler 702 may operate solely on one or more input configuration records from the input molecular combination database 704, such as for example in some usages of modeling system 700 related to scoring of a set of known molecular configurations. In such embodiments, the configuration data modeler 702 may not include a search or optimization strategy and instead be used to perform affinity calculations on an enumerated set of input configuration records.

In some embodiments, various descriptor data related to the configurations of a given molecular combination may be stored or cached in one or more components of a descriptor data storage 720 via one or more storage (or memory) allocation means, structure or apparatus for efficient access and storage during the cycle of computations performed by the configuration modeler 702. In one embodiment, the descriptor data storage 720 may contain chemical or physical descriptors assigned to atoms, bonds, groups, residues, etc. in each of the molecular subsets or may even also contain environmental descriptors. In another embodiment, the descriptor data common to all configurations for a given molecular combination is compactly represented via a storage allocation means in one or more lookup tables. For example, often many physical and chemical descriptors may be identical for different configurations of a combination whereas one or more geometric descriptors are not.

In yet another embodiment, the descriptor data storage 720 may also contain relevant geometric descriptors for the configurations arranged in one or more storage formats via a prescribed storage allocation means. As examples, such formats may involve, but are not limited to, records analogous to pdb or mol2 file formats. Additional examples include various data structures such as those associated with the molecular representation partitioning shown in Ahuja I. As a further example, perhaps stored descriptors for atoms and bonds may represent individual nodes in one or more lists or arrays, or may alternatively be attached, respectively, to nodes and edges of a tree or directed graph.

The whole or parts of the input configuration records 706, and, if applicable, selected configuration records 714 chosen by configuration selector 712, may be converted to data representations used in the storage allocation means of the descriptor data storage 720. Data constructs contained in the descriptor data storage 720 may be either read (i.e., accessed) for use by the configuration data transformation engine 708 or the affinity calculator 709 and may be written either at the inception of or during the execution of a cycle of computation by the configuration modeler 702. The layout and access patterns for the associated descriptor data storage 720 will likely depend on the needs of the affinity calculator 709 as well as the configuration data transformation engine 708.

The affinity calculator 709 may comprise one or more processing (i.e., affinity) engines, where each affinity engine may be dedicated to performing calculations related to one or more affinity components as defined previously in regard to interaction types, affinity formulations, and computation strategies. In some embodiments, different affinity engines are assigned to each unique affinity component. In other embodiments, one or more affinity engines may compute multiple affinity components according to similarity of processing requirements. In yet other embodiments, different affinity engines may be grouped or otherwise arranged together to take advantage of common subsets of required input data in order to improve any caching scheme and/or to reduce the number of, the bandwidth requirements for, or the routing requirements for various associated data paths.

For example, in one embodiment, affinity components for both the electrostatic and vdw interactions involving field-based computation strategies utilizing stored pregenerated probe grid maps, may be computed on the same affinity engine, where said engine requires access to both types of probe grid maps in storage and to various numerical parameters used in evaluating the affinity formulation for the two different interactions. As another example, affinity components for both the hydrogen bonding and vdW interactions using affinity formulations featuring generalized Lennard-Jones potentials computed according to a pair-based computation strategy may be computed on the same affinity engine. In an alternative embodiment, the same two affinity components may be computed using two different affinity engines but grouped together in order to share common input data such as that relating to spatial coordinates and a subset of relevant chemical or physical descriptors.

Typically a processing pipeline is defined as a series of processing elements or engines, which performs a task in several steps, like, for example, an assembly in a factory. Each processing element takes input in and produces output that is stored in its output buffer. In a pipeline the output of each processing element is the input of the following processing element, meaning that one processing element's output buffer is the next processing element's input buffer. A pipeline allows the processing elements to work in parallel thus being more efficient than if each input had to fully processed before beginning computations on the next input. The first processing element in the pipeline often receives input data from one or more storage devices or caches or even other upstream processing pipelines. Similarly the final processing element outputs data to one or more storage devices or caches or even other downstream processing pipelines Each processing element in a pipeline is associated with a pipeline stage. The amount of time taken by a pipeline stage to produce output from its input is defined as a pipeline stage interval. Here a pipeline stage interval is measured in units of cycles (or clock cycles), where a cycle refers to the fundamental period of time recognized by the computational device. A cycle is generally determined by the system clock rate (hence the term clock cycle).

Input to the pipeline stage is read at the start of the pipeline stage interval. In a pipeline input data is expected to be available for reading once the stage interval starts, not before. Similarly output from a pipeline stage is expected to be available only after the end of the stage interval, not before. If instead a pipeline stage must wait some amount of time before starting its processing due to output considerations of previous stages the waiting time is termed a pipeline stall and the processing element is said to be idle during the stall since it has produced its output on one set of data but has not started reading or processing the next set of inputs produced by prior stages.

It is natural for a pipeline to possess a (start-up) latency associated with the total time taken between the first processing element receiving the first input data and the last processing element generating the first output data. Once the latency period has passed and all pipeline stages are regularly processing data in succession, the pipeline is said to have reached a steady state.

In a well-designed pipeline, the pipeline interval is chosen such that pipeline stalls are minimal or nonexistent and each processing element is (nearly) fully utilized once the pipeline has reached a steady state. To achieve maximal utilization the pipeline may require higher latency and more architectural complexity in order to better synchronize the stages so that different inputs do not interfere with one another at any stage in the pipeline. The schedule according to which each stage receives inputs, performs various operations, and outputs results to the next stage in the pipeline within the context of a pipeline stage interval is termed herein as a pipeline schedule.

Two pipelines are said to be parallel pipelines if they operate in parallel, i.e., while one pipeline is processing one sets of inputs the other pipeline is simultaneously processing the same or a different set on inputs. The input buffers of the first processing element in each pipeline may be distinct or may in fact overlap or share storage in common. Similarly the output buffers of the last stage of each pipeline may be distinct or may in fact overlap or share storage in common. Typically input data is received by each pipeline in the form of data blocks or portions arranged and delivered by a data path allocation means or equivalent; discussion of which will be forthcoming.

Two parallel pipelines are said to be synchronized if each pipeline generates results for portions of their respective input data in substantially the same time. Herein the term "substantially the same time" means that the synchronization lag between the two parallel pipelines is a comparatively small time interval, often measured in units of (clock) cycles, wherein the term synchronization lag refers to the gap in time between the output of results of the faster pipeline vs. the output of results of the slower pipeline. If the synchronization lag is zero the two parallel pipelines are said to be perfectly synchronized. If the synchronization lag is small either in terms of (clock) cycles or even in terms of a relative ratio with respect to the time taken by the slowest pipeline to produce results, the two parallel pipelines are said to be nearly synchronized.

According to the design of the two pipelines, the property of synchronization may apply to individual input data blocks or to a collection or stream of data blocks or other portion thereof. Synchronization (either near or perfect) may be achieved by either balancing of processing demands across pipelines, the further internal parallelization of one or both pipelines, or even the introduction of small internal latencies in the faster pipeline, though the latter choice may tend to be less efficient and even undesirable. A detailed example of synchronization will be discussed in regard to FIG. 10.

Returning to discussion of the affinity calculator 709, in some embodiments, the plurality of affinity engines may perform their processing in parallel or in sequence or a hybrid thereof. In some embodiments, the plurality of affinity engines may be arrayed as synchronized parallelized pipelines such that affinity calculations are completed by each engine on portions of input data in substantially the same time. Also according to various embodiments, if applicable, different affinity components computed on the same engine may be performed in either a sequential or a parallel fashion.

In some embodiments, in order to perform and complete affinity calculations across a bank of affinity engines in substantially the same time, especially in the context of a pipeline, different affinity engines may require different amounts of logic gates, circuits, dye area, or other processing elements; may feature different architectures such as different clock frequencies, different caching schemes, different component layouts; or may even be implemented in different mediums such as, for example, an FPGA cell vs. a DSP vs. a small ASIC. Generally the larger, or more complicated, the calculations for a given affinity component, the more processing power that will need to be used for that affinity engine in order to balance the time considerations in relation to other affinity engines. This will be discussed in more detail in regard to examples depicted in FIGS. 9a, 9b, and 10.

The affinity calculator 709 may also include one or more storage components for data specific to the operation of one or more affinity engines according to an affinity-specific storage means. In one embodiment, this may involve the storage of grid maps or potential functions associated with one or more field-based affinity components. In other embodiments, such affinity-specific data storage may also include various numerical parameters, constants, or lookup tables for one or more mathematical functions or expressions. The affinity calculator 709 also includes a suitable data path allocation means for the accessing and delivery of such affinity-specific data, as well as any configuration data generated by the configuration data transformation engine 708. In some embodiments, the included data path allocation means may also be responsible for scheduling the operation of the plurality of affinity engines. In some embodiments, the included allocation means may also be responsible for maintaining the (possibly proximal) synchronicity of the processing pipeline by delivering data to the bank of affinity engines in specified chunks in a prescribed and computationally balanced manner.

More detailed discussion of the configuration modeler 702, including the configuration data transformation engine 708, the affinity calculator 709, and the descriptor data storage 720, will be presented later in association with FIG. 8.

In some embodiments, the configuration results records 711 may include a quantitative measure related to the affinity function (i.e., affinity measure) evaluated for the configuration. In one embodiment, this may be a score. In another embodiment, this may be a probability. In another embodiment, this may be an enthalpy. In another embodiment, this may be a free energy associated with various thermodynamic ensembles (i.e., canonical, microcanonical, grand canonical, etc.). In yet another embodiment, this may be a measure of potency or bioactivity. In other embodiments, the configuration results records 711 may include a qualitative measure related to the affinity function evaluated for the configuration. In one embodiment, this may be a grade. In another embodiment this may be a categorization (i.e., poor, weak, strong, etc.). In yet another embodiment this may be a simple pass-fail measure like active or inactive.

In many embodiments, the configuration results records 711 may also include information used to specify the identity and/or nature of configuration corresponding to the affinity measure. In addition to the identity of the interacting molecular subsets as well as one or more relevant chemical and physical descriptors, there may be a need to annotate or otherwise represent the geometrical state of the configuration. As previously discussed in regard to geometrical transformations, in some embodiments this may involve a recording of a set of geometrical descriptors or state variables associated with degrees of freedom for each molecular subset. Such a set of geometric descriptors (possibly along with knowledge of a template or reference input structure for each molecular subset) may serve as a configuration tag or label, thereby distinguishing one visited configuration from another. For example, a unique value for the six degrees of freedom associated with rigid-body configuration changes involving two molecular subsets might be an appropriate configuration label (provided in this case there are no conformational changes by either molecular subset). However, when using modeling system 700 in certain embodiments related to scoring of configurations perhaps only the affinity measure(s) may be required.

Selections made by the configuration selector 712 may be based on affinity function values, a set of geometrical descriptors describing the structure of each configuration, or other various descriptor data attached to the configuration records. In addition, in some embodiments, the configuration selector 712 may also include a configuration results processing means for the further analysis of a plurality of configuration records stored in the results database such that the selection criteria employed by the configuration selector may make their decisions based on the results of the additional processing. In some embodiments, the configuration selector 712 may utilize various selection criteria in order to resubmit certain configurations back to modeling system 702 for more computations.

In one embodiment, the selection criteria may be predicated on passing of a threshold or other decision mechanism based on one or more qualitative affinity measures. In another embodiment, the selection criteria may be based on a threshold or other decision mechanism based on one or more quantitative affinity measures. In another embodiment, the configuration selector 712 waits until affinity functions have been evaluated for a number of sampled configurations, ranks them by their corresponding affinity measures, and then selects the top X%, where X is a chosen number between zero and 100.

In yet another embodiment, the selection criteria is based on the application of a quantitative threshold derived by calculation of the mean, median, the mode, or various other histogram-based statistics over a plurality of configurations, as provided by the aforementioned configuration results processing means. In yet another embodiment, the further analysis of the configuration results processing means in conjunction with the selection criteria may be based on other statistical analysis of a plurality of configuration records stored in database 710, including, but not limited to, principal component analysis, multidimensional clustering, Bayesian filters, multivariate regression analysis, etc. In yet another embodiment, the further analysis of the configuration results processing means in conjunction with the selection criteria may be based on various pattern matching analysis of a number of different configuration results records stored in database 710, including, but not limited to, use of neural networks, support vector machines, hidden Markov models, etc. In yet another embodiment, the further analysis of the configuration results processing means in conjunction with the selection criteria may be based on clustering of a plurality of configurations based on structural similarity followed by ranking and/or selection of cluster representatives based on affinity function values of cluster members.

In another embodiment, wherein the configuration modeler 702 employs a genetic or memetic algorithm for configuration sampling, the configuration selector 712 may examine a number of configurations results records representing a population of different configurations with corresponding affinity measures and apply a selection operator based on fitness of each configuration with respect to the rest of the population. In another embodiment, wherein the configuration modeler 702 employs simulated annealing or a Monte Carlo based approach for configuration sampling, the configuration selector 712 may examine a number of configurations results records representing a different configurations with corresponding affinity measures and make selections based on one or more probability distributions using the affinity measures.

In some embodiments, the configuration data transformation engine 708 may receive certain resubmitted configurations from the configuration selector 712 and utilize them as inputs to start a new cycle of modeling computations. Once again this may entail the generation (via transformation or ab initio construction) of one or more new configurations based on the resubmitted selected configurations records 714. For example, if a particular configuration was selected from database 710 based on high affinity by the configurations elector 712, the configuration data transformation engine 708 may generate multiple configurations that are structurally similar (i.e., similar but slightly different poses for each molecular subset) in order to better investigate that portion of the possible configuration space of the molecular combination.

In other embodiments, the new cycle of modeling computations instigated by the resubmission of the selected configurations records 714 may involve the operation of the configuration modeler 702 under a different set of conditions or using a different set of control parameters. In further embodiments, the selected configurations records 714 may start a new cycle of modeling computations using a different variant of the configuration modeler 702, including the use of a different affinity calculator or even the use of a different search or optimization strategy altogether.

FIG. 8 illustrates the configuration modeler 702 in more detail as per one embodiment relevant to docking, scoring, or even molecule library screening.

Here item 802 refers to input configuration records obtained either from an input molecular combination database or a configuration selector or both, as described in regard to FIG. 7. The input configuration records 802 are delivered to a configuration record converter 804. The configuration record converter 804 converts the incoming records into molecular representations used in a storage means associated with one or more components of an input descriptor data storage 806. The configuration data converter is also responsible for the assignment of all descriptors that are either missing or are to be derived directly from the input configuration data. Here the input descriptor data storage 806 is broken up into four components, an input chemical descriptor data storage 808, an input physical descriptor data storage 810, an input environmental descriptor data storage 812, and an input structural data storage 814 containing various geometric descriptors. In one embodiment it is assumed that the relevant chemical, physical, and environmental descriptors will remain unchanged for different configurations of the same molecular combination, but will need to be updated when analyzing a new combination. Also in some embodiments, the input structural data in storage 814 contains geometrical descriptors describing one or more initial poses for each molecular subset that will act as seeds for the configuration data transformation engine 816.

A configuration data transformation engine 816 accesses the data stored in the input descriptor data storage 806 to generate one or more configurations of the molecular combination and stores each configuration via a storage allocation means in a configuration data storage 818, which for one embodiment would feature specialized molecular graph data structures such as those discussed in regard to the molecular representation partitioning shown in Ahuja I. Note that the configuration data transformation engine 816 may both read and write to the configuration data storage 818. The four components of the input descriptor data storage 806 and the configuration data storage 818 constitute the descriptor data storage discussed previously in regard to FIG. 7 (i.e., item 720). In one embodiment the input descriptor data storage 806 and the configuration data storage 818 are implemented as banks of SRAM caches.

In one embodiment, the configuration data storage 818 is implemented as or includes one or more double-buffered caches so that downstream processes can be run on stored configurations while others are still being generated. Also in one embodiment, data corresponding to each molecular subset in a single configuration is read from or written to the data storage 818 in data blocks of fixed maximal size so as to ensure efficient pipeline operation. Moreover, data blocks from multiple different configurations may be read or written simultaneously in parallel in order to reduce latency.

It is contemplated that the configuration data transformation engine 816 may read back a subset of the configuration data in storage 818 involving one or more configurations in order to generate new further configurations as per a search or optimization strategy included as part of the transformation engine 816. In one embodiment, the configuration data transformation engine 816 also utilizes one or more random number generators in order to construct or transform configurations as per a stochastic search or optimization strategy.

An affinity calculator 820 comprises multiple components as identified by the shaded portion of FIG. 8. On component is a data path allocator 821 that manages the allocation of data to a plurality of data paths 822 connected to a bank of processing (or affinity) engines 826. The data path allocator 821 reads configuration data from the configuration data storage 818, and, in some embodiments, the data is accessed from the configuration data storage 818 in data blocks in a manner similar to that discussed in regard to data accesses made by the configuration data transformation engine 816.

In one embodiment, the data path allocator 821 distributes data to the affinity engines 826 in data blocks. A data block may involve both selection and rearrangement of all or a portion of the data associated with one or more configuration data blocks reads from storage 818. The structure of a data block (i.e., what data it contains and how it is arrange in memory) may depend on the nature of the calculation to be performed by its destination affinity engine(s). A data block may be submitted to more than one affinity engine either in sequence or in parallel. According to some embodiments data block may contain information relating to more than one molecular subset across more than one configuration. In other embodiments the data blocks may be so small that each data block includes only one value. Two data blocks may include common information, though possibly arranged differently to meet the needs of the intended affinity engines. Data blocks prepared for different components of an affinity calculator may be arranged or organized differently due to different data and bandwidth requirements across different affinity components. In some embodiments, one or more data blocks are transmitted to the affinity engines according to a data path schedule as prescribed by the data path allocation means. Here the term data path schedule refers to a temporal scheme for the transmission and routing of data blocks to the affinity engines. In one embodiment, the data path schedule may be analogous to a traffic schedule where instead the traffic is represented by data blocks, the roads are represented by the data paths, and the destinations are represented by the affinity engines. In one embodiment, the data path schedule may be synchronous in nature according to a preset master clock. In another embodiment, the data path schedule may be asynchronous in nature according to a handshaking protocol wherein an affinity engine can notify the data path allocation means that it is ready for the next input data block.

As an example consider the methotrexate ligand of FIG. 5 for which it was estimated that there are more than $6 \times 10^{23}$ possible configurations for the combination featured in FIGS. 4a-4c, provided the protein remains fixed and the flexibility of the methotrexate ligand is based on six rigid body and ten torsional degrees of freedom. While it is possible, though impractical, for the configuration data transformation engine 816 to generate all the $6 \times 10^{23}$ possible configurations in a brute force search, it is more likely that the configuration data transformation engine 816 will decide to generate a subset of the possible configuration space over the course of analysis of the molecular combination, though this may still involve millions and even billions of individual configurations.

The set of configurations to be assessed may be provided individually to the configuration data storage 818 or may be provided as a conglomerated representation featuring multiple configurations that will then be separated out by the data path allocator 821 into one or more parallelized streams each featuring a sequence of data blocks, however arranged, that are intended for downstream processing. For example, the configuration data transformation engine 816 may send data blocks representing a conglomeration of all configuration data from one hundred configurations at a time to the configuration data storage 818. However, continuing with the example, data path allocator 821 may then extract configuration data from storage 818 and form a collection of data blocks, each block comprising a one-hundred-atom subset from one molecular subset. As an alternate example, each data block may represent up to three distinct one-hundred-atom subsets from two molecular subsets obtained from ten different configurations already stored in the configuration data storage 818.

Typically, the data path allocator 821 will attempt to keep the plurality of data paths 822 as full as possible by sending data blocks to each affinity engine in parallel. The rate at which an individual data block is to be transmitted along a data path to its destination affinity engine will depend on the data bandwidth associated with its corresponding data path and on the processing performance of the destination affinity engine. The arrangement, size, and scheduling of one or more data blocks may be dynamically configurable and therefore may be adjusted for different molecular combinations featuring different molecular subsets, or even for different analyses of the same molecular combination such as may be related to different iterative cycles of the configuration modeler 702.

In some embodiments, the data path allocator 821 may cache one or more data blocks according to a storage allocation means in order to feed the destination affinity engines 826 according to a tight pipeline schedule with little or no pipeline stalls. In one embodiment, such a caching scheme may feature one or more dedicated double-buffered caches based on SRAM. In yet another variation in another embodiment some or all of the data caches may be implemented using register files in order to alleviate potential data path routing problems such as may be encountered in an ASIC implementation of the configuration modeler.

The data path allocator 821 also is connected to one or more dedicated affinity data storages 824 that include data specific to the operation of one or more affinity engines 826. For example, the affinity data storages 824 may contain data representation of one or more potential field functions, probe grid maps, occupancy 3-D grids, etc. The affinity data storages 824 may also contain various numerical constants, mathematical function lookup tables (e.g., polynomial, trigonometric, logarithmic, or special function lookup tables), or other affinity-specific parameters or tabulated functions. In some embodiments, the affinity data storages 824 may store large data constructs in DRAM (since standard file I/O may be very slow) whereas smaller data entities like lookup tables and parameters are stored in SRAM caches. In some embodiments, the data path allocator 821 may include one or more dedicated memory controllers to control read or write data accesses to the various described caches or connected storages.

The data paths 822 themselves are in charge of routing and carrying data blocks sent out by the data path allocator 821 to various intended affinity engines 826. In some embodiments, different data paths may have different data bandwidths depending on the needs of the destination affinity engines and on the size of the carried data blocks.

As previously discussed in regard to the affinity calculator 709 of FIG. 7, the bank of affinity engines 826 is a collection of processing engines, each engine dedicated to performing affinity calculations related to one or more affinity components. In FIG. 8, the bank of affinity engines 826 is comprised of N individual affinity engines denoted by 827 (first engine), 828 (second engine), and 829 (Nth engine) where the ellipsis represents the other (N–3) affinity engines arrayed between 828 and 829. In one embodiment, dedicated data paths to the data path allocator 821 connect each individual affinity engine. As each affinity engine finishes its calculations, the results are provided to an affinity component accumulator 830. In one embodiment, the bank of affinity engines 826 operate in parallel receiving streams of allocated data blocks in parallel sent down the collection of data paths 822 by data path allocator 821, which transmits as many data blocks as needed to complete the calculation of all affinity components of the affinity function for all assessed configurations.

In some embodiments, each affinity engine may also include one or more internal memory caches in order to appropriately cache one or more inbound data blocks from the data path allocator 821. In one embodiment, such internal input caches may be double-buffered for reads and writes and may be implemented in SRAM or register files or some combination thereof.

As also described earlier in regard to the affinity calculator 709 of FIG. 7, and depending on the embodiment, each affinity engine pictured in FIG. 8 may be devoted to computation of one or more related affinity components or may instead reflect groups of affinity engines sharing one or more common data paths and possibly one or more common internal input caches or portions thereof, thereby more efficiently making use of available data bandwidth. In some embodiments, each of the affinity engines 826 represents a processing pipeline comprising one or more processing stages wherein each stage performs a set of calculations on portions of input data blocks in a pipeline interval according to a tight pipeline schedule.

This concept is best illustrated in regard to FIG. 9a, shows a schematic overview of an affinity engine 900 devoted to computing two affinity components respectively associated with vdW and electrostatic interactions and both using a field-based computation strategy. In this example, the affinity engine has access to all necessary potential function data stored in probe grid maps in DRAM as indicated by arrow 902. Also in this example, the affinity engine also includes an internal input SRAM cache 904 holding a data block comprising a collection of atoms to be affected by the stored potential fields using the probe grid map approximation.

In this example, the processing of affinity engine 900 is split into two different pipelines 906 and 914, respectively for the vdW and electrostatic interactions. Each pipeline comprises one or more processing elements each corresponding to a part of the calculations (i.e., a pipeline stage). In this example there are seven stages for the vdW pipeline (labeled as stages 907 through 913) and four stages for the electrostatics pipeline (labeled as stages 915 through 918). In this case, all processing elements associated with a single stage in both pipelines compute their own portion of the calculations on blocks of ten atoms at a time, receiving inputs from a previous stage and outputting intermediate results to the next stage (except of course for the first and last stages). Moreover, both pipelines 906 and 914 will function in parallel.

In describing the operations of the two pipelines, suppose that initially only stages 907 and 915 are working in parallel on the first set of ten atoms to be processed. Assume that stage 907 finishes first and outputs data to stage 908, which then begins its own operation. Meanwhile 907 starts calculations on the next set of ten atoms. At some point stage 915 finishes the first set of calculations and ships data to stage 916, which then begins its own calculations while 915 starts in on the next set of ten atoms. As each stage finishes it sends data to the next stage in the pipeline and then moves on to its own calculations for the next data set of ten atoms. Once the last stage in each pipeline is completed, the final results of both pipelines 906 and 914 are sent to an appropriate storage or accumulator as indicated by arrows 919 and 920.

Assuming there are plenty of data blocks of ten atoms available to keep each pipeline running in a steady state, eventually all pipeline stages in both paths will be fully operational.

The typical goal is to design the pipeline in such a way that each processing unit is fully operational and busy at all times when running in a steady state. The time interval between initiation of the first stage in a pipeline on the first set of ten atoms and the output of the first set of results, also corresponding to the first set of ten atoms, from the last stage in the same pipeline is in fact the latency of the pipeline for that particular pipeline.

In the example of affinity engine 900 in FIG. 9a, in order to keep the pipelines flowing in a steady, fully operational state, the internal input SRAM cache 904 may be double-buffered, meaning that as data blocks of ten atoms are read from the first (read buffer) as part of the current data block, new data blocks of ten atoms corresponding to the next data block are being steadily built up in the second (write) buffer so that once the first data block is fully processed by the two pipelines 906 and 914, the second buffer is ready to go, the read and write designation of the two buffers is exchanged, and the initial stage in each pipeline begins calculations on data blocks of ten atoms from the new data block. There are many other standard embodiments of caching schemes that will produce similar efficiencies.

In some embodiments of an affinity engine, the included pipelines, such as 906 and 914 of FIG. 9*a*, may operate in parallel and each may include one or more dedicated processing units working in concert, where each dedicated processing unit in either pipeline may be physically implemented as any of the following compute devices: dedicated microprocessors, FPGAs, ASICs, hardware boards, DSPs, or any combination thereof.

As another example of pipeline stages within an affinity engine, consider FIG. 9*b* which depicts a bond-based affinity engine 950 that calculates an affinity component related to the intramolecular strain energy associated with bond angle changes according to a quadratic formulation, where $E_{bend} = C_1 \cdot K_\theta \cdot (\theta - \theta_0)^2 \cdot [1 - C_2 \cdot (\theta - \theta_0)^4]$, $C_1$ and $C_2$ are constants, $K_\theta$ and $\theta_0$ are physical descriptors assigned by a molecular-mechanics force field based on the types of covalent bonds involved, and $\theta$ is the angle defined by the two relevant bond vector. In FIG. 9*b*, a first pipeline stage 955 may be in charge of calculating the quantity $(\theta - \theta_0)$ for a given bond pair using a dedicated adder. A second pipeline stage 960 might involve a dedicated multiplier to form $(\theta - \theta_0)^2$ and a third stage 970 may construct $(\theta - \theta_0)^4$ based on the results of the second stage 960. At this point the pipeline may branch such that one stage 974 computes the term $C_1 \cdot K_\theta \cdot (\theta - \theta_0)^2$ while the other stage 978 simultaneously computes the term $[1 - C_2 \cdot (\theta - \theta_0)^4]$. The results from these two branches may then be recombined by a final stage 980 featuring a dedicated multiplier in order to form the final value for $E_{bend}$ for a given bond pair. While the dedicated multiplier of stage 960 is multiplying out $(\theta - \theta_0)^2$ for a current pair of bonds, the dedicated adder of stage 950 could be calculating $(\theta - \theta_0)$ for a following pair, and so on. The pipeline stages might be allocated according to computational capacity and power so that when one stage finishes, the next stage is ready to receive the new intermediate results. In this example, it is likely that stages featuring multiplies will require more computational muscle per clock cycle when compared to the first stage featuring only addition.

The embodiments of pipelining, already discussed in regard to an individual affinity engine in FIGS. 9*a* (or 9*b*), may be extended to apply to the configuration modeler for part or all of its components. For example, as the configuration data transformation engine 816 finishes generating one or more data blocks and sends them to the configuration data storage 818, the data path allocator 821 may prepare and transmit one or more data blocks down the data paths 822 with sufficient designed data bandwidth to the bank of affinity engines 826 while the configuration data transformation engine 816 works to generate the next configuration data block. Moreover, while the data path allocator 822 buffers and/or transmits the current data blocks, the bank of affinity engines 826 may be processing affinity components for the previous cycle of data blocks while simultaneously receiving the current data blocks into internal input memory caches. In some embodiments, both the configuration data and affinity data blocks may feature data from more than one molecular subset and even from more than configuration. There may be many multiple various embodiments featuring various pipeline strategies for the configuration modeler depicted in FIG. 8.

In some embodiments of an affinity engine, the processing resources for stages associated with each pipeline may be allocated such that the pipelines are synchronized thereby generating results in parallel for the same portion of data in substantially the same time as already defined with regard to parallel pipelines. As an example consider once again the affinity engine 900 depicted in FIG. 9*a* and assume that all stages in either data path feature the same number of computations. Since pipeline 906 contains seven stages vs. only four stages for pipeline 914, if stages in both pipeline feature processing units with similar processing performance and capacity, then pipeline 914 associated with an electrostatic field-based affinity component will complete calculations for a given data set of ten atoms sooner than its vdW field-based counterpart pipeline 906.

In one embodiment, the faster of the two pipelines, in this case 914, may wait an interval of time after completing calculation for the current data set before starting calculations for the next data set, in this case on the next set of ten input atoms to be processed, so that both processing pipelines initiate calculations for the next data set at (or very nearly) the same time. However, this would mean introduction of latency for the faster of the two pipelines and thus mean that one of the pipelines is not operating fully and therefore less efficiently than possible.

In alternative embodiments, multiple pipelines are synchronized (either nearly or perfectly) by balancing processing requirements across the each pipeline. In the case of FIG. 9*a*, this might mean devoting more and/or faster processing units to the otherwise slower pipeline. For example, in one embodiment, assuming equality of computational performance for all stages in both pipelines, the processing units on pipeline 906 may be over-clocked to run at 1.75 times the rate so that the seven pipeline stages of pipeline 906 generate a result at the same time as the four stages of pipeline 914 provided the input data set was received at the same time by both pipelines. As an additional example, in an alternative embodiment, the one or more processing units included in pipeline 906 may be designed to perform more calculations per unit time (e.g., clock cycle or equivalent) so that the two pipelines are synchronized. In embodiments featuring implementation on a chip or an FPGA this may mean devoting more dye area, more logic gates, more processing cells, etc. to processing units in the more compute intensive pipeline. Of course, alternative embodiments may involve slowing down various processing units in the less compute intensive pipeline. Such embodiments may be extended to more than two pipelines in a given affinity engine.

Once a portion or whole of the results relating to calculation of one or more affinity components on a data block are generated by individual affinity engines 827 through 829 in FIG. 8, the results are sent to an affinity accumulation means represented by an affinity component accumulator 830 in FIG. 8. The affinity accumulation means is responsible for composition of the component values to complete evaluation of an affinity function for one or more configurations. In one embodiment, the composition of component values is a linear combination involving numerical weights applied to each affinity function component.

As discussed previously in regard to the affinity calculator 709 of FIG. 7, in some embodiments (including the preferred) the parallel operation of affinity engines across the bank 826 are synchronized and thereby deliver results to the affinity component accumulator 840 at substantially the same time.

In one embodiment the affinity component accumulator 830 may receive affinity component results from each affinity engine in parallel and may operate in a manner such that the accumulated affinity function values corresponding to one or more synchronized blocks of data are generated by the accumulator 830 in substantially the same time. In yet other embodiments, the accumulator 830 may include one or more optional double-buffered input caches so that the accumulator 830 can be working in a pipelined fashion on component data associated with one molecular configuration while the affinity engines are working on the next portion of data associated with the next molecular configuration. In yet other embodiments, the affinity component accumulator 830 may be accumulating affinity functions for more than one molecular configuration in parallel.

To further illustrate various embodiments regarding synchronization of multiple pipelines by balancing processing requirements across each pipeline, one may view the individual affinity engines of FIG. 8 as analogs of the pipelines depicted in FIG. 10 where instead provisions are made to balance processing requirements across affinity engines as opposed to internal affinity engine pipelines so that each affinity engine may remain busy, or alternatively latencies are reduced, when processing molecular configurations or even combinations.

In FIG. 10, a data path allocation means represented by a data path allocator 1004 regulates the disbursement of data blocks containing relevant input data to each of two groups of affinity engines denoted by items 1006 and 1016. In this example, the first group of affinity engines 1006 comprises two separate engines for the pair-wise computation of intermolecular vdW (1010), and hydrogen bond (1012) interactions between molecular subsets. The second group of affinity engines 1016 comprises only one engine for the field-based computation of intermolecular electrostatic (1020) interactions based on a probe grid map approximation.

An accumulation means in this example comprises a set of individual intermediate accumulators 1014 and 1022 dedicated to each group of affinity engines as well as a final accumulator 1040 to construct the complete affinity function values. All of the affinity engines work in a pipeline with respect to the allocation and accumulation means such that as one data block is being processed the next data block is being transmitted to input caches appointed to each group of affinity engines.

In this example, a single data block 1002 sent to the first group of affinity engines 1006 comprises the relevant descriptor data for up to 100 atoms from each molecular subset for ten different configurations of the molecular combination (i.e., for two sets of 100×10 atoms, each set corresponding to one molecular subset). A single data block 1003 sent to the second group of affinity engines 1016 comprises the relevant descriptor data for up to 100 nonsource atoms from one molecular subset (wherein the nonsource atoms are under the influence of the electrostatic potential field-based one-source charges in the other molecular subset) for ten different configurations of the molecular combination.

For the sake of simplifying the current example depicted in FIG. 10 let us assume that the computational cost of operations performed by each engine within a group of affinity engines is the same (e.g., compute cost is same for vdw engine 1010 and hydrogen bond engine 1012). To complete calculations on data block 1002 the intermolecular vdw engine 1010 and the intermolecular hydrogen bond engine 1012 must each process 10×(100×100) pairs. In this example, let the operational cost for one pair in either engine 1010 or 1012 be Q, so then the total cost for either engine is $N_Q \times Q$, where $N_Q = 10^6$ is the number of pairs to be processed in data block 1002. Now to complete calculations on data block 1003 the field-based electrostatic engine 1020 must process 10×100 atoms. In this example, let the operational cost for one atom in engine 1020 be P, so then the total cost for the engine is $N_P \times P$, where $N_P = 10^3$ is the number of atoms to be processed in data block 1003.

In order to generate results for an input data block for the three groups of affinity engines in substantially same time (i.e., synchronization across the affinity engines) it is required that the quantities $N_Q \times Q$ and $N_P \times P$ are nearly identical, i.e., their relative ratio is nearly unity. Typically this will not be the case unless steps are taken to increase or decrease the speed of various engines and thereby balance the load across the engines. For example, if Q=40 clock cycles, P=200 clock cycles, $N_Q = 10^6$ and $N_P = 10^3$ then we see that the first group of affinity engines is some 200 times slower than the second group.

It may not be possible to reduce the time Q to generate an individual result for a pair of atoms in the vdW (910) and hydrogen bond (912) engines as this may be limited by the number of sequential adds and multiplies. On the other hand it may be fairly easy to increase P so as to slow down affinity engine 1020. For example, if P is dominated by the access time to retrieve electrostatic potential data from DRAM or equivalent storage, it may be possible to slow down the access time by a factor of B, where B>1 so that the field-based affinity engine 1020 operates at 1/B the original rate, i.e., each result for the second group of affinity engines requires B*P cycles to produce. However, if for the current numerical example B=10, then this still means that the first group of affinity engines 1006 is twenty times slower in aggregate than the second group.

Another alternative then is to reduce the total computing time of data block 1002 in the first group of affinity engines 1006 by making use of fine grained parallelism of processing pipelines dedicated to individual pair-wise computations. Let us assume that the individual time necessary to process one pair, Q, cannot be easily reduced. Instead, the vdW pair-wise affinity engine 1010 (and also the hydrogen bond engine 1012) may comprise A>1 different pipelines, each pipeline producing results for one pair in Q clock cycles. Thus in Q clock cycles A pairs are processed whereas only Q/(B×P) atoms are processed in affinity engine 1020 (note the factor of B was the aforementioned slow-down factor introduced into engine 1020 in this example) in Q cycles. If the ratio between $[(N_Q \times Q)/A]$ and $[(N_P \times B \times P)]$ is unity (or very close to unity) then the two affinity engines are considered to be synchronized, meaning the two engines generate results in substantially the same time for an input data block.

For our current example, if Q=40 clock cycles, P=200 clock cycles, $N_Q = 10^6$, and $N_P = 10^3$ then designing affinity engines 1010 and 1012 to each include A=20 distinct parallel pipelines will result in both groups of affinity engines producing results for each input data block in substantially the same time (i.e., synchronized). In a different example, where Q=25 clock cycles, P=80 clock cycles, $N_Q = 10^6$, and $N_P = 10^3$. If A=40 and B=12.5 then the two groups of affinity engines are once again synchronized.

Alternative embodiments may involve both the usage of slowing down individual pipeline steps and having more individual pipelines per engine. To illustrate this better, let us reexamine the previous example. Instead of A=40 and B=12.5 we could have instead let A=80 and additionally slow each pipeline step in the first group of affinity engines by a factor of two and still maintain synchronization. In other embodiments, the same methodology may be applied in order to synchronize additional groups of affinity engines, e.g., to balance a third group of engines with respect to the first and second groups. In some embodiments, the same methodology may be applied to individual affinity engines within a group of engines in order to synchronize results generation within the group. In one embodiment, similar methods are used to maintain synchronization across the set of accumulators dedicated to each affinity engine, or alternatively, groups of affinity engines.

In one embodiment, the synchronization of the affinity engines depicted in FIG. 10 in regard to components of the affinity calculator 709 may be perfectly synchronized, i.e., no synchronization lag. In another embodiment, the synchronization of the affinity engines depicted in FIG. 10 in regard to components of the affinity calculator 709 may be nearly synchronized such that results are generated from input data blocks in substantially the same time. In some embodiments, substantially the same time may equate to a constraint on the synchronization lag of less than or equal to one millisecond, since otherwise it is not generally feasible to expect the synchronization lag to be less than one millisecond for a computational platform or device calculating affinity functions for a variety of molecular subsets, unless provisions have been made in the architecture or design of the pipelines to ensure synchronization as such a high level of fidelity. In other embodiments, substantially the same time may equate to a constraint on the synchronization lag of less than or equal to ten clock cycles as relates to the fundamental period of time recognized by the computational platform or device. In yet other embodiments, substantially the same time may equate to a constraint on the synchronization lag of less than or equal to an integral number of the largest pipeline stage interval occurring in the multiple parallel pipelines. In further embodiments, the integral number may be as small as unity. In yet other embodiments, substantially the same time may equate to a constraint on the synchronization lag of less than or equal to 50% of the time taken by the slowest pipeline to complete output results generation from an input data block.

Returning to FIG. 8, in some embodiments, synchronization of affinity results generation across the plurality of affinity engines 826 in conjunction with the accumulation means represented by accumulator 830 may be enforced for individual input data blocks. In other embodiments, the synchronization of affinity results may be enforced over the course of a portion or whole of the sequence or stream of data blocks needed to complete the calculation of all or part of the affinity components associated with a single configuration. In yet other embodiments featuring the parallel affinity computation of data related to multiple configurations, the enforcement of results synchronization might be applied over a stream of data blocks needed to complete the calculation of all or part of the affinity components associated with the multiple corresponding configurations. In yet another embodiment, results are synchronized based on completion of calculations for all or part of the affinity components associated with a molecular combination. In other embodiments, the synchronization may be applied to the receiving of affinity component results for accumulation by the accumulation means from the bank of affinity engines. In some embodiments this may involve dynamic allocation of data bandwidths and processing resources and capacity as related to one or more calculation components, such as individual affinity engines, in order to maintain synchronization for different molecular combinations featuring different molecular subsets.

Once a portion or whole of the accumulated affinity function values for a data block are generated by accumulator 830 in FIG. 8, the results may be subjected to a results filter 840. The results filter 840 may apply various decision or selection criteria based on input affinity function values measures to determine whether or not a particular molecular configuration should be stored in the results database 710 of FIG. 7. In principle, a particular molecular configuration may demonstrate little or no binding affinity and thus the corresponding configuration may not be of interest in further analysis and as such it may be desirable to filter out such poor affinity configurations. In some embodiments, the results filter may apply selection criteria similar to one or more of the embodiments already discussed in regard to the configuration selector 712.

As previously discussed in regard to some embodiments, once configuration results are stored in results database 710, a configuration selector 712 may be used to select one or more configuration results records for resubmission to the configuration data modeler 702 as part of an iterative cycle. Examples of embodiments featuring such an iterative loop include, but are not limited to, embodiments of the configuration data modeler 702 that involve the use of one or more search and/or optimization techniques such as steepest descent, conjugate gradient, modified Newton's methods, Monte Carlo, simulated annealing, genetic or memetic algorithms, brute force sampling, pattern matching, etc.

In summarizing such embodiments involving iteration, the configurations records are input to the configuration data modeler 702 at the beginning of an iterative cycle and then subjected to one or more configuration transformations in order to generate one or more new configurations. A set of configurations (comprising possibly both old and new configurations) is then submitted to an affinity calculator 709 in order to generate affinity functions for each configuration. Decisions (e.g., filtering, selection, etc.) are then made with regard to the resultant configuration results records and a subset of the configurations assessed in the current iterative cycle are selected and resubmitted to the configuration data modeler 702 in order to initiate a new iterative cycle of computation. The process continues until certain terminating conditions are fulfilled. Examples of terminating conditions include, but are not limited to, reaching a predetermined number of configurations visited, achieving a predetermined number of iterations, or even achieving a number of configurations with affinity better than a certain threshold.

As already discussed above, the choice of search and/or optimization strategy dictates the nature of the configuration-sampling scheme or schedule (i.e., construction of new configurations) as well as the characteristics of the configuration selector 712. Modeling system 700 can be used to analyze a molecular combination wherein both molecular subsets may only move relative to one another as per a rigid body, i.e., six degrees of freedom regarding relative translation and orientation of the two molecular subsets. In this example, the six degrees of freedom represent an intermolecular separation distance, three Euler angles for the first molecular subset (i.e., roll, pitch, and yaw), and two Euler angles for the second molecular subset (i.e., pitch and yaw). In this example, the search strategy employed by the configuration modeler 702 is that of a brute force search that samples the six dimensional configuration space according to a regular sampling scheme.

For the present example, suppose that the pitch and yaw angles for either subset are sampled as a set of regularly spaced points on the surface of a unit sphere, the intermolecular separation distance is sampled by regularly spaced intervals on a line connecting the centers of each molecular subset, and the roll angle of the first molecular subset is sampled by regularly spaced intervals on the circumference of a circle. In this example, the brute force search strategy will visit and assess each state (or element) of the resultant Cartesian product of the aforementioned three sampling schemes. Assuming 50 radial sample points for the separation distance, 100 angular sample points for the roll angle of the second molecular subset, and 1000 sample points for the pair of pitch and yaw Euler angles for each molecular subset this amounts to a total of 5 billion configurations visited by the configuration modeler 702.

To prime the pump an input reference configuration is submitted to the configuration data transformation engine 818 of FIG. 8, which in turn, according to the sampling schedule, produces the first sampled configuration. This configuration is then submitted for analysis by the affinity calculator 709 comprising, in this example, three affinity engines. In this example, the first engine is dedicated to computations of intermolecular electrostatic interactions between the two molecular subsets according to a field based computation strategy (e.g., probe grid map approximation built from source charges in second molecular subset) for a Coulombic energy model. The second engine is dedicated to computations of intermolecular vdW interactions between the two molecular subsets according to a pair-wise computation strategy for a 12-6 Lennard Jones potential. The third engine is dedicated to computations of intermolecular hydrogen bond interactions between the two molecular subsets also according to a pair-wise computation strategy for a modified 12-10 Lennard Jones potential.

In this example, data blocks, comprising up to 100 atoms from each molecular subset are allocated according to molecular representation partitioning shown in Ahuja I and then submitted to the affinity engines. In the case of the pair-wise based engines (second and third), each engine receives two data blocks at time, one for each molecular subset, whereas the field-based first engine receives only one data block representing up to a 100 atoms of the first molecular subset under the influence of the electrostatic potential generated by the second molecular subset. The affinity engines operate in parallel to one another and are pipelined with respect to their internal calculations as well as with respect to their inputs received from the data path allocator 821 and their affinity component outputs to the accumulator 830. Furthermore, they are synchronized such that their affinity component results for each data block are completed and sent to the accumulator 830 in substantially the same time, wherein the synchronization is achieved by appropriate design of each affinity engine in order to load balance the computational and bandwidth capacity across the bank of engines.

In this example, the affinity function value is then accumulated in accumulator 830 and then subjected to a quantitative affinity threshold in a results filter 840. A passing value means that a configuration results record will be stored in the configuration results database 710. The entire computation cycle then begins a new iteration or computational cycle wherein the configuration data transformation engine produces yet another new sampled configuration, an affinity function value is computed, the affinity value thresholded, and possibly a results record is stored. The iterative process continues until all sampled configurations according to the aforementioned brute-force sampling schedule have been visited. The results database 710 may then be further analyzed in order to identify configurations with high affinity that may represent favorable binding modes between the two molecular subsets.

In an extension of this example, instead of operating on one configuration at a time the configuration data modeler corresponding to this example embodiment may process multiple configurations simultaneously. This is especially relevant for embodiments that feature a search optimization strategy such as a genetic algorithm wherein a population of molecular configurations is constructed in the configuration data transformation engine during each iteration via application of crossover and mutation operator, The population is then subsequently analyzed by the bank of affinity component engines in order to generate a fitness measure based on the accumulated affinity function and the configuration selector 712 applies various selection operators in order to drive the configuration data transformation engine for the next iteration. Obviously such example embodiments can be easily extended to include other arrangements and types of affinity engines corresponding to various interactions.

In summary, the modeling system 700 represents a method for efficiently computing the affinity function between two or more molecular subsets of a molecular configuration, possibly as part of an analysis of a molecular combination. Here the analysis of molecular combinations may include, but is not limited to, prediction of likelihood of formation of a potential molecular complex, or a proxy thereof, the estimation of the binding affinity or binding energy between molecular subsets in an environment, the prediction of the binding mode (or even additional alternative modes) for the molecular combination, or the rank prioritization of a collection of molecular subsets (e.g., ligands) based on predicted bioactivity with a target molecular subset, and would therefore also include usage associated with computational target-ligand docking and scoring.

The modeling system 700 comprises an input means for the assigning of one or more molecular descriptors associated with each sampled molecular configuration, a storage means for the digital storage of molecular descriptor data associated with each sampled molecular configuration, a plurality of calculation means representing one or more affinity processing engines, each engine dedicated to the calculation of one or more affinity components for a molecular configuration, a plurality of data paths for the transmission of molecular descriptor data to the plurality of calculation means connecting the storage means to the plurality of calculation means, a data path allocation means for the allocation of molecular descriptor data to the plurality of data paths, and finally an accumulation means that accumulates affinity function values based on input affinity component data generated by the plurality of calculation means.

According to various embodiments the input means may comprise an input molecular combination database (or equivalently separate target and ligand databases for analysis of target-ligand combinations), a plurality of input configuration records, and a configuration record converter for the conversion of input configuration records into various molecular representations. The storage means may comprise one or more storage components for various descriptor data including chemical, physical, geometric/structural, and environmental descriptors in one or more caches (i.e., SRAM, DRAM, register files, etc.) or on one or more storage media devices (hard drives, memory sticks, computer-recordable media, etc.). The storage means also may provide for storage of various data relevant to calculation of affinity functions including numerical parameters, constants, function lookup tables, or even the storage of grid maps or potential functions associated with one or more field-based affinity components.

The plurality of calculation means may comprise one or more affinity engines each dedicated to the calculation of one or more affinity components. According to various embodiments, the affinity engines may each include one or more processing pipelines that each receive data transmitted along a plurality of data paths and operate in parallel. In some embodiments, different affinity engines may be assigned to each unique affinity component, whereas in other embodiments, one or more affinity engines may compute multiple affinity components, typically based on similarity of processing requirements. In yet other embodiments, different affinity engines may be grouped or otherwise arranged together to take advantage of common data blocks in order to improve caching and/or to reduce data bandwidth. Typically, descriptor data is apportioned to each of the affinity engines as one or more data blocks and transmitted to each of the affinity engines according to a data path schedule as prescribed by the data path allocation means. In some embodiments, the data blocks represent one or more partitions of various molecular representations that are constructed and scheduled according to various architectural requirements involving memory storage, data bandwidth, and both routing and affinity processing requirements. Individual affinity component values (or results) are typically submitted to an accumulation means in a pipelined fashion, where the accumulation means comprises one or more accumulators dedicated to forming affinity function values for each sampled molecular configuration as per a prescribed affinity composition rule. In some embodiments the calculation means and the accumulation means may process multiple configurations in parallel and in further embodiments the input data blocks may comprise descriptor data associated with parts or all of one or more molecular subsets from one or more molecular configurations. In other embodiments, one or more affinity engines may be dedicated to the processing of each molecular subset, whether for the molecular subset in its entirety or for one or more specific portions.

In some embodiments, the affinity processing engines of the calculation means are synchronized such that the accumulation means receives, or is expected to receive, its inputs from each calculation means at substantially the same time. As previously discussed in the context of FIG. 10, the synchronization may be perfect or may instead be near. Moreover, the term substantially the same time implies a constraint on the amount of synchronization lag across the affinity engines. Several examples of embodiments regarding the magnitude of the constraint on synchronization lag were already discussed in the context of FIG. 10.

In further embodiments of modeling system 700 regarding analysis of molecular combinations involving the computation of affinity functions for molecular subsets for a plurality of molecular configurations (e.g., virtual screening, docking, scoring, etc.) the modeling system 700 may further include a configuration generation means for the construction and/or transformation of a plurality of molecular configurations based on one or more input reference configurations. In some embodiments, new configurations may be constructed by application of various geometrical operators characterized by sets of geometrical descriptors.

As already discussed, in some embodiments, the set of configurations generated via transformation during the course of an analysis of a molecular combination may be determined according to a schedule or sampling scheme specified by one or more search and/or optimization techniques used to drive the modeling processes of the configuration modeler 702. Examples of operators include the mutation (unary) and crossover (binary) operators used in relation to a genetic algorithm-based search or optimization strategy, the randomly generated (possibly according to a biased probability distribution) state operator used in relation to a Monte Carlo or simulated annealing-based search or optimization strategy, or deterministic application of various molecular transformations or structural perturbations corresponding to one or more conformational or rigid body degrees of freedom describing the pose of a molecular subset. The configuration generation means may construct new configurations in series (i.e., one at a time), data from which is submitted to the calculation means in a sequential manner. Alternatively, the configuration generation means may construct multiple new configurations in parallel at the same time and submit them in parallel to the calculation means.

In further embodiments of modeling system 700 regarding analysis of molecular combinations involving the computation of affinity functions for molecular subsets for a plurality of molecular configurations, the modeling system 700 may further include a results storage means for the digital storage of a plurality of corresponding configuration records, including one or more affinity function values, corresponding to a plurality of molecular configurations.

Additionally the modeling system 700 may also include a configuration selection means for the selection of one or more molecular configurations according to selection criteria applied to a plurality of configuration records stored in the results storage means. The configuration selection means may also utilize a configurations results processing means for the further analysis of a plurality of configuration records stored in the results database such that the selection criteria employed by the configuration selection means may make their decisions based on the results of the additional processing. Various embodiments of the selection criteria and the configuration results processing means are discussed earlier in the description.

In further embodiments of modeling system 700, the selected molecular configurations chosen by the configuration selection means may be resubmitted to the configuration generation means and new molecular configurations constructed, using the selected molecular configurations as input. The new molecular configurations may then be subjected to a new cycle of configuration modeling including affinity computations followed by further configuration selection, the iterative process repeating certain terminal conditions are achieved. Embodiments regarding the iterative operation of the configuration modeler in the context of an analysis of molecular combinations are also discussed earlier in the description.

A novel system for the analysis and modeling of molecular combinations has been described based on the efficient pipelined computation of an affinity function between two or more molecular subsets for various molecular configurations. The above description is illustrative and not restrictive. Many variations of the invention will become apparent to those of skill in the art upon review of this disclosure. The scope of the invention should, therefore, be determined not with reference to the above description, but instead should be determined with reference to the appended claims along with their full scope of equivalents.

What is claimed is:

1. A method for determining whether a biomolecule is a lead candidate by using a computational system to compute an affinity function between two or more molecular subsets of a molecular configuration of the biomolecule or target or both defined by a configuration dataset, the method comprising:
    assigning to each of the molecular subsets one or more molecular descriptors associated with the molecular configuration of the biomolecule or target or both, wherein each molecular descriptor represents one or more properties or elements of a molecular subset;
    storing, in a descriptor data storage, the assigned molecular descriptors as molecular descriptor data;
    allocating, with a data path allocator that is a circuit of the computational system, the molecular descriptor data to a plurality of data paths associated with a plurality of affinity engines, each being a separate circuit of the computational system;

for each data path:
  partitioning the molecular descriptor data allocated to the respective data path into a plurality of data blocks; and
  routing the data blocks to the respective data path according to a data path schedule that specifies a rate that the data blocks are sent in sequence along the respective data path and specifies a size of a respective data block,
  wherein the data path schedule takes into account the amount of processing needed for calculating an affinity component for all or part of the molecular descriptor data and the amount of processing power available from each affinity engine so as to reduce a synchronization lag between affinity engines;

transmitting the molecular descriptor data from the descriptor data storage to the plurality of affinity engines, wherein transmitting uses the plurality of data paths;

generating, with the plurality of affinity engines, affinity component results for the molecular configuration, wherein each affinity engine includes one or more processing pipelines, wherein each affinity engine generates results for only one affinity component, wherein each affinity component corresponds to a different type of interaction energy between the molecular subsets;

accumulating affinity function values based on affinity component results generated by the plurality of affinity engines and received by an affinity component accumulator; and determining whether a biomolecule is a lead candidate based on the accumulated affinity function values.

2. The method of claim 1, wherein the affinity engines are synchronized such that the affinity component accumulator receives, or is expected to receive, an input from each affinity engine with a synchronization lag that is less than a predetermined value.

3. The method of claim 2, wherein the predetermined value for the synchronization lag is less than or equal to one millisecond.

4. The method of claim 1, wherein the affinity engines are synchronized such that the affinity component accumulator receives, or is expected to receive, an input from each affinity engine at substantially the same time, wherein substantially the same time equates to a constraint on the synchronization lag of less than or equal to ten clock cycles of the computational system.

5. The method of claim 1, wherein the affinity engines are synchronized such that the affinity component accumulator receives, or is expected to receive, an input from each affinity engine at substantially the same time, wherein substantially the same time equates to a constraint on the synchronization lag of less than or equal to the largest pipeline stage interval across the affinity engines.

6. The method of claim 1, wherein the affinity engines are synchronized such that the affinity component accumulator receives, or is expected to receive, an input from each affinity engine at substantially the same time, wherein substantially the same time equates to a constraint on the synchronization lag of less than or equal to a user predetermined ratio of a time taken by the slowest pipeline of the affinity engines to completely process a user predetermined amount of input data.

7. The method of claim 6, wherein substantially the same time equates to a constraint on the synchronization lag of less than or equal to 50% of a time taken by the slowest pipeline of the affinity engines to completely process a user predetermined amount of input data.

8. The method of claim 1, wherein the molecular descriptors include one or more chemical descriptors associated with the molecular subsets.

9. The method of claim 1, wherein the molecular descriptors include one or more physical descriptors associated with the molecular subsets.

10. The method of claim 1, wherein the molecular descriptors include one or more geometrical descriptors associated with the molecular configuration.

11. The method of claim 1, wherein the molecular descriptors include one or more environmental descriptors associated with the molecular configuration.

12. The method of claim 1, wherein the two or more molecular subsets represent one or more portions of a molecule and its ambient environment wherein the molecule interacts with itself and with its ambient environment and wherein the affinity function is computed for various poses of the one molecule.

13. The method of claim 1, wherein the computational system is used as part of an analysis of a molecular combination involving the computation of a plurality of affinity functions for a plurality of molecular configurations.

14. The method of claim 13, further comprising constructing a plurality of molecular configurations based on one or more input reference configurations.

15. The method of claim 13, wherein the system computes an affinity function for multiple configurations in parallel.

16. The method of claim 13, further comprising storing a plurality of configuration records including one or more affinity function values, each configuration record corresponding to one of a plurality of molecular configurations.

17. The method of claim 16, further comprising selecting one or more molecular configurations according to selection criteria applied to a plurality of configuration records.

18. The method of claim 17, wherein selecting one or more molecular configurations according to the selection criteria comprises applying a decision threshold to the affinity function values of each configuration.

19. The method of claim 18, wherein the decision threshold is adaptively determined based on observed statistics of the affinity function values generated for a plurality of configurations.

20. The method of claim 17, wherein the configuration with the best affinity function value is chosen.

21. The method of claim 17, wherein the configuration records are ranked by their affinity function values and a plurality of top ranking configurations are selected.

22. The method of claim 17, wherein selecting one or more molecular configurations comprises:
  assigning a probability value or fitness value to each configuration based on a probability distribution or other function dependent on one or more affinity function values; and
  selecting configurations stochastically based on the probability values or fitness values.

23. The method of claim 17, wherein the selection of configuration records is based on both affinity function values and structural similarity to other configurations.

24. The method of claim 17, wherein as part of a feedback cycle, new molecular configurations are constructed using the selected molecular configurations as input.

25. The method of claim 24, wherein the new molecular configurations are subjected to another cycle of affinity function computations and configuration selection and the iterative process of subjecting the new molecular configurations to another cycle of affinity function computations and configuration selection is repeated until certain terminal conditions are achieved.

26. The method of claim 17, further comprising constructing new molecular configurations from one or more stored configurations, wherein the constructing is based on a set of instructions derived from the selecting process.

27. The method of claim 26, wherein the new molecular configurations are subjected to another cycle of affinity function computations and configuration selection and the iterative process of subjecting the new molecular configurations to another cycle of affinity function computations and configuration selection is repeated until certain terminal conditions are achieved.

28. The method of claim 1, wherein assigning one or more molecular descriptors associated with a molecular configuration comprises retrieving user predetermined numerical parameters from a molecular mechanics force field or other similar molecular parameter set.

29. The method of claim 1, wherein the data blocks are arranged such that data block boundaries coincide with partitions of a molecular representation.

30. The method of claim 1, wherein the data path schedule is synchronous in nature.

31. The method of claim 1, wherein the data path schedule is asynchronous in nature.

32. The method of claim 1, wherein the computational system is used as part of an analysis of a molecular combination involving the computation of a plurality of affinity functions for a plurality of molecular configurations and wherein the data path allocator submits data, from different configurations, across the plurality of data paths to the affinity engines.

33. The method of claim 1, wherein the affinity component accumulator comprises a plurality of intermediate accumulators such that a dedicated intermediate accumulator is provided for each affinity engine, an intennediate accumulator being an accumulator that generates intermediate accumulated values, and wherein the affinity function value for a configuration is generated from these intermediate accumulated values.

34. The method of claim 1, wherein each affinity engine is dedicated to affinity computations for parts or all of one molecular subset.

35. The method of claim 1, wherein the computational system comprises one or more of a general purpose programmable computer including software to implement the computational platform, dedicated hardware, firmware, or a combination thereof.

36. The method of claim 1, wherein the timing of sending data blocks is different for at least two data paths, and wherein the size of the data blocks are different for at least two data paths.

37. The method of claim 1, wherein each data path is associated with a respective affinity engine.

38. The method of claim 1, further comprising:
for each affinity component:
computing the amount of processing to calculate the respective affinity component for the given molecular configuration, wherein the computation uses a number of operations to calculate the respective affinity component, a cost per operation, and a number of pipelines in the corresponding affinity engine.

39. The method of claim 38, wherein computing the amount of processing to calculate the respective affinity component for the given molecular configuration uses the formula:
$(N \times Q)/A$, where N is the number of operations to calculate the respective affinity component, Q is the cost per operation, and A is the number of pipelines in the respective affinity engine.

40. The method of claim 1, further comprising:
for each affinity component:
computing the amount of processing to calculate the respective affinity component for the given molecular configuration, wherein the computation uses an amount of data allocated to the corresponding affinity engine, memory in the corresponding affinity engine, and bandwidth of the corresponding affinity engine.

41. A circuit for determining whether a biomolecule is a lead candidate by computing an affinity function between two or more molecular subsets of a molecular configuration of the biomolecule or target or both defined by a configuration dataset, the integrated circuit comprising:
a configuration data converter for assigning to each of the molecular subsets one or more molecular descriptors associated with the molecular configuration of the biomolecule or target or both, wherein each molecular descriptor represents one or more properties or elements of a molecular subset;
a descriptor data storage that is communicably coupled with the configuration data converter and that stores molecular descriptor data representing the one or more molecular descriptors;
a plurality of affinity engines that each generate one or more affinity components for the molecular configuration, wherein each affinity engine includes one or more processing pipelines, wherein each affinity engine generates results for only one affinity component, wherein each affinity component corresponds to a different type of interaction energy between the molecular subsets;
a plurality of data paths connecting the descriptor data storage to the affinity engines, wherein the data paths are capable of transmitting all or part of the molecular descriptor data from the descriptor data storage to the plurality of affinity engines;
a data path allocator that:
allocates the transmitted molecular descriptor data to the plurality of data paths, and
for each data path:
partitions the molecular descriptor data allocated to the respective data path into a plurality of data blocks; and
routes the data blocks to the respective data path according to a data path schedule that specifies a rate that the data blocks are sent in sequence along the respective data path and specifies a size of a respective data block,
wherein the data path schedule takes into account the amount of processing needed for calculating an affinity component for all or part of the molecular descriptor data and the amount of processing power available from each affinity engine so as to reduce a synchronization lag between affinity engines; and
an affinity component accumulator that accumulates affinity function values based on affinity component results generated by the plurality of affinity engines, wherein the accumulated affinity function values are used to determine whether the biomolecule is a lead candidate.

42. The circuit of claim 41, wherein the affinity engines are synchronized such that the affinity component accumulator receives, or is expected to receive, an input from each affinity engine with a synchronization lag that is less than a predetermined value.

43. The circuit of claim 41, wherein the integrated circuit is used for part of an analysis of a molecular combination involving the computation of a plurality of affinity functions for a plurality of molecular configurations, and
   wherein the data path allocator is configured to submit data across the plurality of data paths to the affinity engines according to one or more data blocks that may include portions of input data from different configurations.

44. The circuit of claim 41, wherein the affinity component accumulator comprises a plurality of intermediate accumulators such that a dedicated intermediate accumulator is provided for each affinity engine, an intermediate accumulator being an accumulator that generates intermediate accumulated values, wherein the affinity function value for a configuration is generated from these intermediate accumulated values.

45. The circuit of claim 41, wherein the timing of sending data blocks is different for at least two data paths, and wherein the size of the data blocks are different for at least two data paths.

46. The circuit of claim 41, wherein the one or more pipelines of each affinity engine include circuitry that is hardwired to compute the specific interaction energy of the respective affinity engine, and wherein at least two of the affinity engines have a different processing power.

* * * * *